(12) United States Patent
Close

(10) Patent No.: US 11,938,299 B2
(45) Date of Patent: *Mar. 26, 2024

(54) INFUSION AND BLOOD COLLECTION DEVICES

(71) Applicant: MEDTG, LLC, Brazil, IN (US)

(72) Inventor: Benjamin W. Close, Brazil, IN (US)

(73) Assignee: MEDTG, LLC, Brazil, IN (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/313,896

(22) Filed: May 8, 2023

(65) Prior Publication Data
US 2023/0270937 A1    Aug. 31, 2023

Related U.S. Application Data

(63) Continuation of application No. 17/104,899, filed on Nov. 25, 2020, now Pat. No. 11,642,458.
(Continued)

(51) Int. Cl.
*A61B 5/00* (2006.01)
*A61B 5/15* (2006.01)
*A61M 5/168* (2006.01)

(52) U.S. Cl.
CPC ... *A61M 5/16804* (2013.01); *A61B 5/150351* (2013.01); *A61B 5/150946* (2013.01);
(Continued)

(58) Field of Classification Search
CPC .......... A61M 5/16804; A61M 2250/00; A61M 39/06; A61M 2039/0258;
(Continued)

(56) References Cited

U.S. PATENT DOCUMENTS 3,490,441 A    1/1970 Curtis
3,610,226 A   10/1971 Albisser
(Continued)

FOREIGN PATENT DOCUMENTS

CN    101573154 A    11/2009
CN    101631498 A     1/2010
(Continued)

OTHER PUBLICATIONS

U.S. Appl. No. 18/298,280, filed Apr. 10, 2023, Thomas A. Hall, III.
(Continued)

*Primary Examiner* — May A Abouelela
(74) *Attorney, Agent, or Firm* — Innovation Law Office; Dennis S. Schell

(57) ABSTRACT

A device for the uninterrupted administration of fluid to an animal body during a draw of bodily fluid, e.g., blood, is disclosed. A first fluid channel is configured to selectively transport IV fluid to an animal body and to draw a bodily fluid from the body. A sealing member for sealing a bodily fluid draw port defines a concave surface on a first end. The sealing member concave surface forms an interior surface portion of the first fluid channel. A connection member is configured to connect to a catheter to the first fluid channel and defines a concave distal end. A second fluid channel continuously provides IV fluid to a lumen coaxially located within the catheter. The concave surface and the concave distal end are shaped to create fluid flow patterns that quickly and completely remove residual bodily fluid remaining after a draw of bodily fluid is completed.

20 Claims, 34 Drawing Sheets

Related U.S. Application Data

(60) Provisional application No. 62/940,596, filed on Nov. 26, 2019.

(52) U.S. Cl.
CPC .... *A61B 5/150992* (2013.01); *A61B 2503/40* (2013.01); *A61M 2250/00* (2013.01)

(58) Field of Classification Search
CPC .. A61M 2039/0276; A61M 2039/0282; A61M 2039/066; A61M 39/0247; A61B 5/150351; A61B 5/150946; A61B 5/150992; A61B 2503/40; A61B 5/15003; A61B 5/150221; A61B 5/154
See application file for complete search history.

(56) References Cited

U.S. PATENT DOCUMENTS

| | | | |
|---|---|---|---|
| 3,841,307 A | 10/1974 | Friedell | |
| 3,958,562 A | 5/1976 | Hakim et al. | |
| 3,983,864 A | 10/1976 | Sielaff et al. | |
| 4,014,333 A | 3/1977 | McIntyre | |
| 4,072,146 A | 2/1978 | Howes | |
| 4,098,275 A | 7/1978 | Consalvo | |
| 4,160,448 A | 7/1979 | Jackson | |
| RE31,873 E | 4/1985 | Howes | |
| 4,665,927 A | 5/1987 | Daily | |
| 4,822,343 A * | 4/1989 | Beiser | A61B 5/150496 604/243 |
| 4,865,583 A | 9/1989 | Tu | |
| 5,013,304 A | 5/1991 | Russell et al. | |
| 5,122,129 A | 6/1992 | Olson et al. | |
| 5,165,406 A | 11/1992 | Wong | |
| 5,193,545 A | 3/1993 | Marsoner et al. | |
| 5,250,066 A | 10/1993 | Lambert | |
| 5,290,246 A | 3/1994 | Yamamoto et al. | |
| 5,312,361 A | 5/1994 | Zadini et al. | |
| 5,364,374 A | 11/1994 | Morrison et al. | |
| 5,374,245 A | 12/1994 | Mahurkar | |
| 5,378,230 A | 1/1995 | Mahurkar | |
| 5,395,319 A | 3/1995 | Hirsch et al. | |
| 5,451,206 A | 9/1995 | Young | |
| 5,568,806 A | 10/1996 | Cheney, II et al. | |
| 5,607,401 A | 3/1997 | Humphrey | |
| 5,620,008 A * | 4/1997 | Shinar | A61B 5/15003 600/576 |
| 5,637,399 A | 6/1997 | Yoshikawa et al. | |
| 5,846,228 A | 12/1998 | Alexander | |
| 5,876,366 A | 3/1999 | Dykstra et al. | |
| 5,891,105 A | 4/1999 | Mahurkar | |
| 5,947,953 A | 9/1999 | Ash et al. | |
| 5,951,521 A | 9/1999 | Mastrototaro et al. | |
| 5,954,701 A | 9/1999 | Matalon | |
| 6,032,059 A | 2/2000 | Henning et al. | |
| 6,146,354 A | 11/2000 | Beil | |
| 6,190,371 B1 | 2/2001 | Maginot et al. | |
| 6,221,058 B1 | 4/2001 | Kao et al. | |
| 6,228,864 B1 | 5/2001 | Smith et al. | |
| 6,245,079 B1 | 6/2001 | Nobles et al. | |
| 6,569,117 B1 | 5/2003 | Ziv et al. | |
| 6,758,835 B2 | 7/2004 | Close et al. | |
| 7,335,182 B1 * | 2/2008 | Hilaire | A61M 39/06 604/27 |
| 8,348,844 B2 | 1/2013 | Kunjan et al. | |
| 8,364,231 B2 | 1/2013 | Kamath et al. | |
| 8,366,685 B2 | 2/2013 | Devgon | |
| 9,855,386 B2 | 1/2018 | Close et al. | |
| 10,383,605 B2 | 8/2019 | Niestroj-Pahl et al. | |
| 11,141,545 B2 * | 10/2021 | Anderson | A61M 15/08 |
| 11,623,038 B2 | 4/2023 | Hall, III et al. | |
| 11,642,458 B2 | 5/2023 | Close | |
| 2001/0001125 A1 | 5/2001 | Schulman et al. | |
| 2001/0003991 A1 | 6/2001 | Sato et al. | |
| 2001/0007932 A1 | 7/2001 | Kamen et al. | |
| 2001/0009994 A1 | 7/2001 | Small et al. | |
| 2001/0016715 A1 * | 8/2001 | Mayer | A61M 39/045 604/249 |
| 2001/0019019 A1 | 9/2001 | Nordman et al. | |
| 2001/0020591 A1 | 9/2001 | Hasegawa et al. | |
| 2001/0021429 A1 | 9/2001 | Nizuka et al. | |
| 2001/0025157 A1 | 9/2001 | Kriesell | |
| 2003/0149395 A1 | 8/2003 | Zawacki | |
| 2003/0208154 A1 | 11/2003 | Close et al. | |
| 2004/0210162 A1 | 10/2004 | Wyatt et al. | |
| 2004/0236286 A1 | 11/2004 | Klein | |
| 2005/0027233 A1 * | 2/2005 | Flaherty | A61B 5/150503 600/576 |
| 2006/0000432 A1 | 1/2006 | Yamamoto et al. | |
| 2006/0189926 A1 * | 8/2006 | Hall | A61B 5/14546 600/316 |
| 2007/0083091 A1 | 4/2007 | Sterling et al. | |
| 2007/0179436 A1 | 8/2007 | Braig et al. | |
| 2007/0219509 A1 | 9/2007 | Tashiro et al. | |
| 2008/0200837 A1 | 8/2008 | Frazier et al. | |
| 2008/0319346 A1 * | 12/2008 | Crawford | A61B 5/150656 600/576 |
| 2009/0048576 A1 | 2/2009 | Robinson et al. | |
| 2009/0124964 A1 | 5/2009 | Leach et al. | |
| 2009/0178459 A1 * | 7/2009 | Li | C12Q 1/001 73/1.02 |
| 2009/0259145 A1 * | 10/2009 | Bartfeld | B01L 3/5021 600/576 |
| 2011/0009720 A1 | 1/2011 | Kunjan et al. | |
| 2011/0160662 A1 * | 6/2011 | Stout | A61M 25/0606 604/122 |
| 2011/0319728 A1 * | 12/2011 | Petisce | A61B 5/6852 600/309 |
| 2012/0095369 A1 | 4/2012 | Teixeira et al. | |
| 2012/0191010 A1 | 7/2012 | Cabot | |
| 2012/0277627 A1 | 11/2012 | Devgon | |
| 2012/0277630 A1 | 11/2012 | Devgon | |
| 2013/0165868 A1 * | 6/2013 | Isaacson | A61M 25/0693 29/428 |
| 2013/0178760 A1 * | 7/2013 | Downie | A61B 5/154 600/573 |
| 2014/0046214 A1 | 2/2014 | Devgon et al. | |
| 2014/0188002 A1 | 7/2014 | Close et al. | |
| 2014/0207083 A1 * | 7/2014 | Pessin | A61M 39/0606 604/256 |
| 2014/0276215 A1 * | 9/2014 | Nelson | A61M 39/223 600/573 |
| 2014/0364766 A1 | 12/2014 | Devgon et al. | |
| 2015/0173663 A1 * | 6/2015 | Teoh | A61B 5/150274 600/576 |
| 2015/0201963 A1 * | 7/2015 | Snow | A61B 17/3421 604/167.03 |
| 2018/0140240 A1 * | 5/2018 | Bullington | A61B 5/150396 |
| 2018/0214682 A1 * | 8/2018 | Woehr | A61M 39/0613 |
| 2018/0304041 A1 * | 10/2018 | Leeflang | A61M 39/06 |
| 2019/0091462 A1 | 3/2019 | Bihlmaier et al. | |
| 2019/0125236 A1 * | 5/2019 | Hoan | A61M 5/1413 |
| 2019/0160275 A1 | 5/2019 | Funk et al. | |
| 2019/0262599 A1 * | 8/2019 | Nakagami | A61M 25/06 |
| 2020/0078564 A1 * | 3/2020 | Blanchard | A61M 25/0606 |
| 2020/0254195 A1 * | 8/2020 | Nakagami | A61M 25/0097 |
| 2020/0352498 A1 | 11/2020 | Schuster et al. | |
| 2021/0045688 A1 * | 2/2021 | Komada | A61D 1/00 |
| 2021/0113811 A1 | 4/2021 | Nakagami et al. | |
| 2021/0116041 A1 | 4/2021 | Mermelshtein et al. | |
| 2021/0138162 A1 * | 5/2021 | Nakagami | A61M 5/158 |
| 2021/0299344 A1 | 9/2021 | Urakabe | |
| 2021/0389215 A1 * | 12/2021 | Gao | G01N 1/10 |
| 2022/0257919 A1 * | 8/2022 | Damarati | A61M 39/24 |

FOREIGN PATENT DOCUMENTS

| | | |
|---|---|---|
| CN | 101678192 A | 3/2010 |
| RU | 2335302 C2 | 10/2008 |
| WO | 2008042625 A2 | 4/2008 |
| WO | 2012149109 A2 | 11/2012 |

(56) References Cited

FOREIGN PATENT DOCUMENTS

| WO | 2013130254 A1 | 9/2013 |
| WO | 2014106266 A1 | 7/2014 |
| WO | 2021108624 A1 | 6/2021 |

OTHER PUBLICATIONS

U.S. Appl. No. 18/313,896, filed May 8, 2023, Benjamin W. Close.
"Thread", www.merriam-webster.com/dictionary/thread, printed Mar. 16, 2016, 10 pages.
Examination Report for Appl. No. CA 2,896,716 dated Aug. 21, 2019.
Examination Report for Appl. No. IN 6068/DELNP/2015 (dated Jan. 9, 2020).
Office Action for Appl. No. CN 201380074068.8 (dated Aug. 18, 2016).
Office Action for Appl. No. CN 201380074068.8 (dated Jun. 28, 2017).
Office Action for Appl. No. EP 13867172.2 (dated Oct. 25, 2016).
Office Action for Appl. No. RU 2015129013 (dated Aug. 28, 2018).
Office Action for Appl. No. RU 2015129013 (dated Oct. 19, 2017).
Written Opinion of the International Searching Authority and International Search Report for PCT/US2013/078538, dated Mar. 27, 2014.
Written Opinion of the International Searching Authority for PCT/US2020/062316 dated Feb. 17, 2021.
Extended European Search Report for EP 20892843.2 dated Nov. 3, 2023.

\* cited by examiner

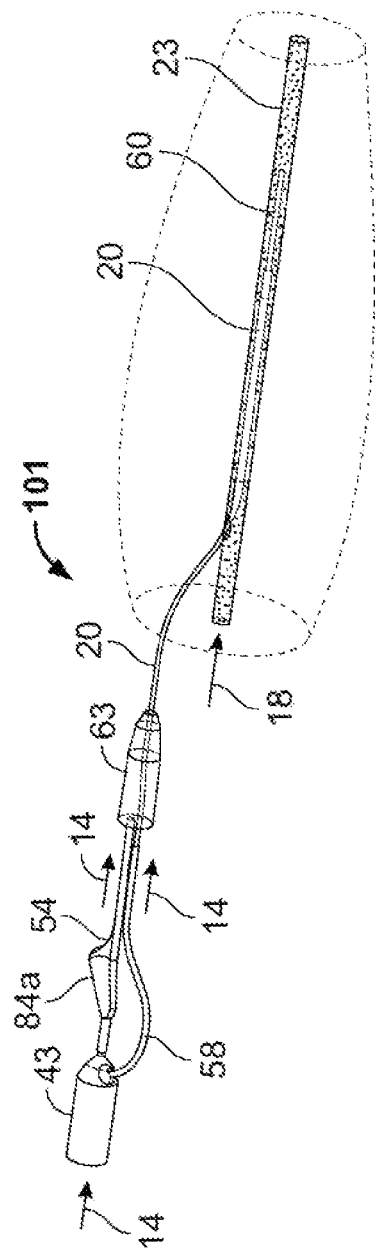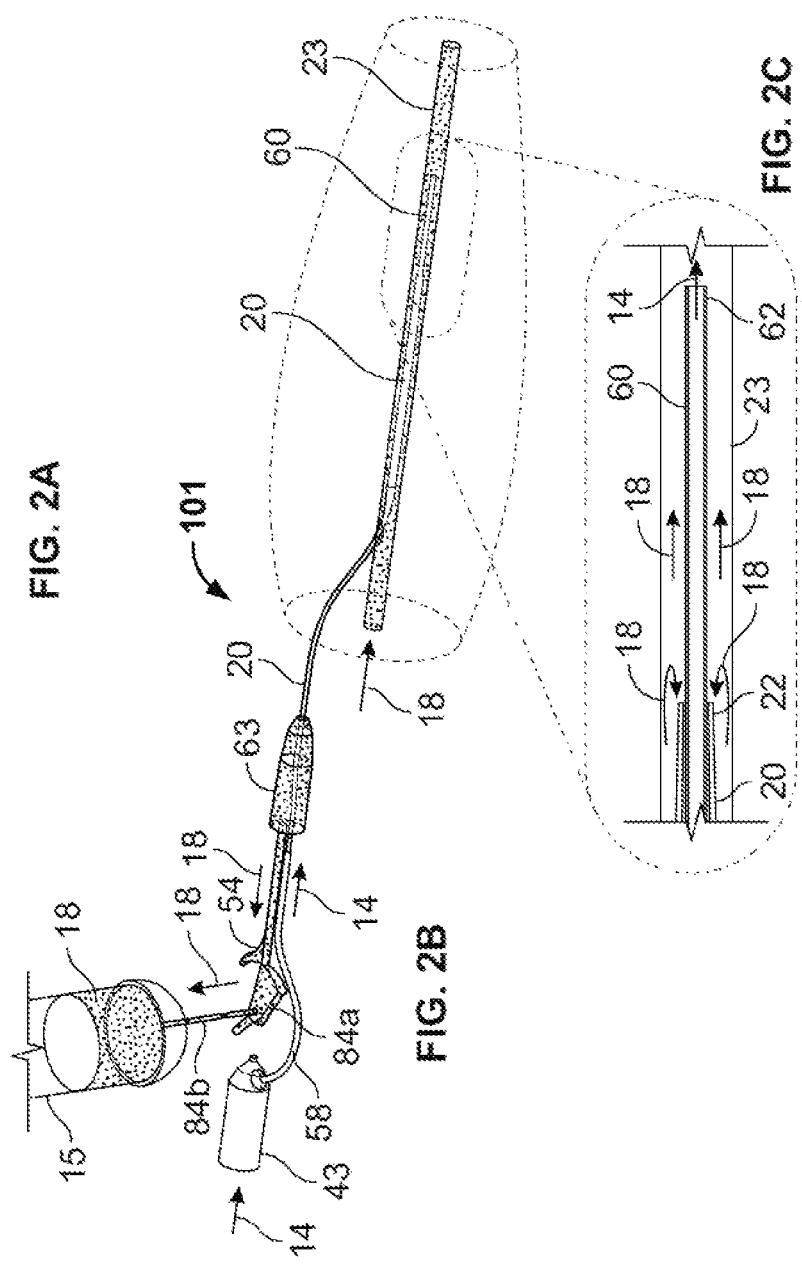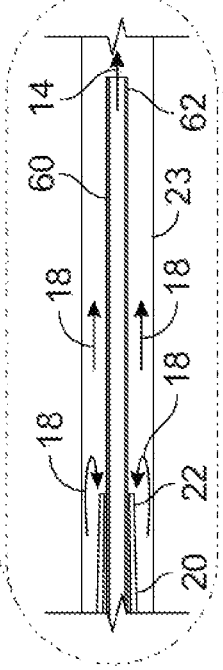
FIG. 2A
FIG. 2B
FIG. 2C

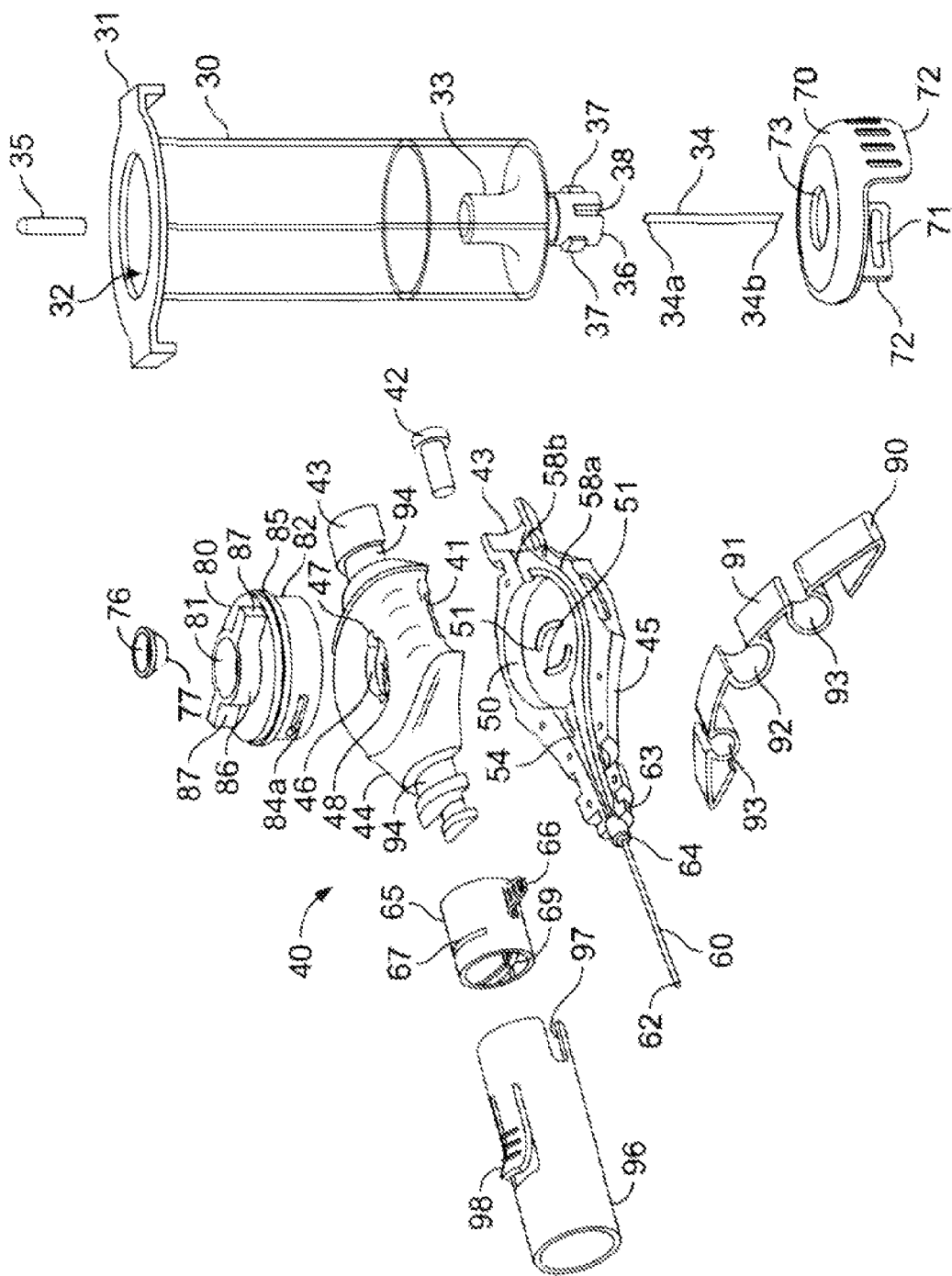

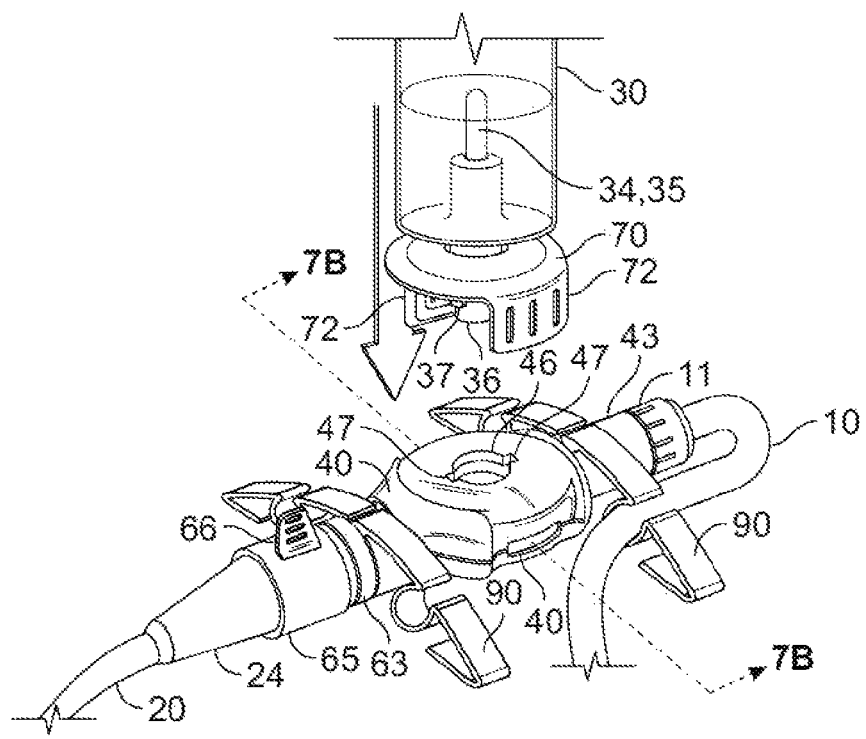
FIG. 7A
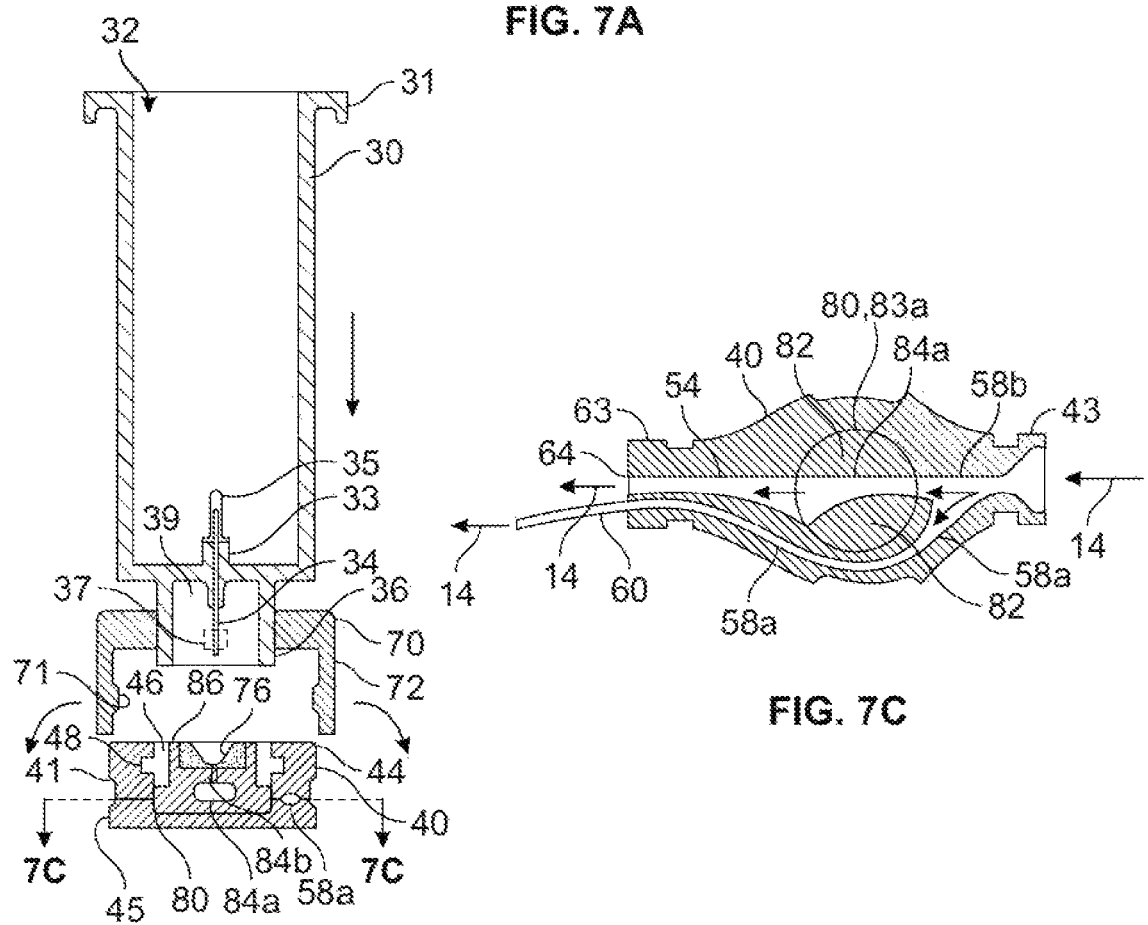
FIG. 7B
FIG. 7C

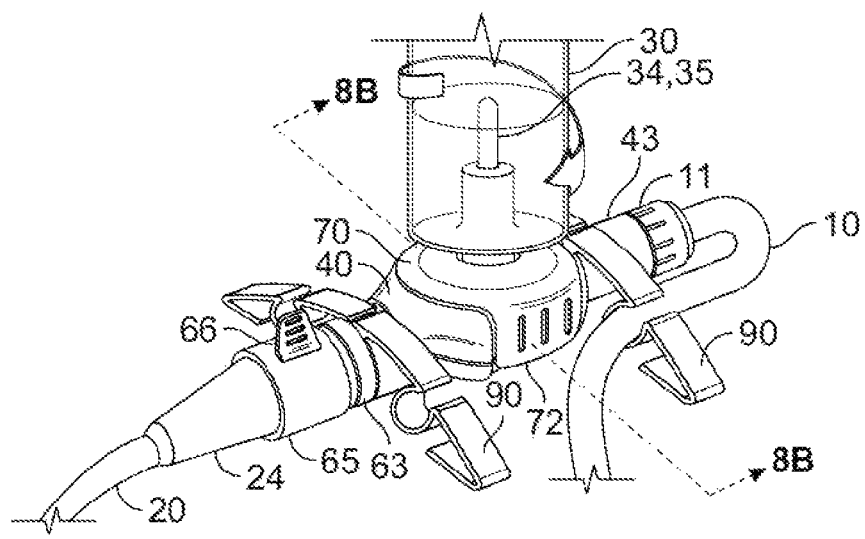
FIG. 8A
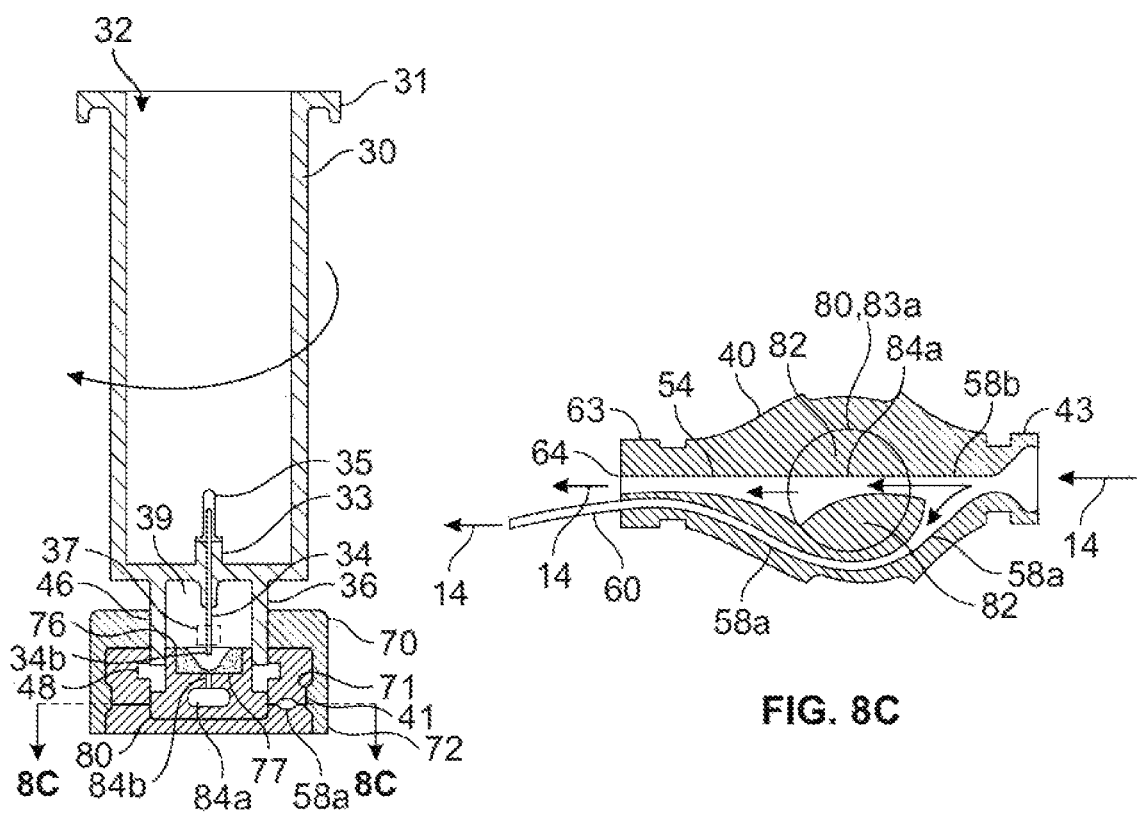
FIG. 8B
FIG. 8C

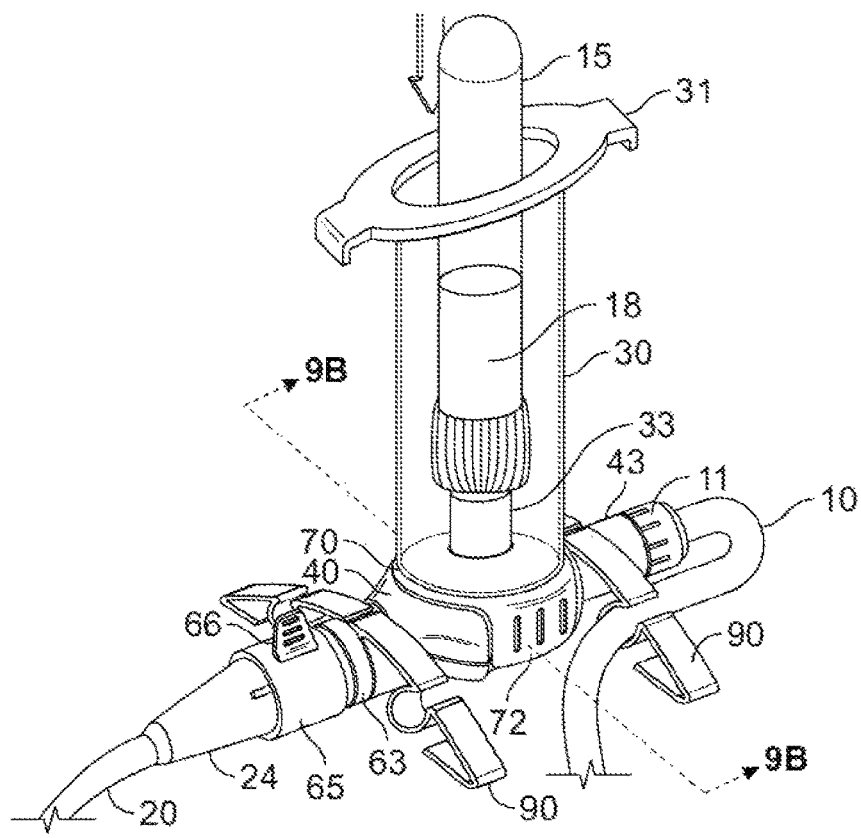
FIG. 9A
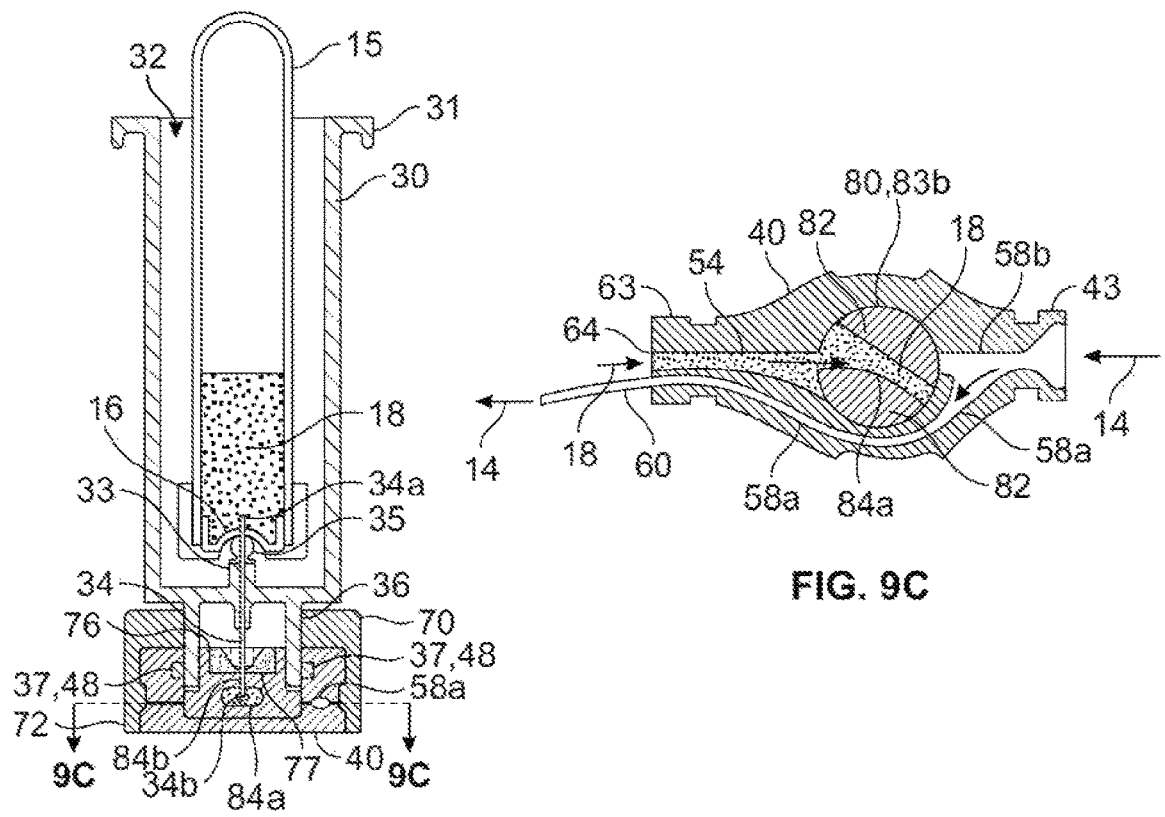
FIG. 9B
FIG. 9C

INFUSION AND BLOOD COLLECTION DEVICES

CROSS-REFERENCE TO RELATED APPLICATION

This is a continuation patent application of U.S. Nonprovisional patent application Ser. No. 17/104,899, filed Nov. 25, 2020, now U.S. Pat. No. 11,642,458, titled INFUSION AND BLOOD COLLECTION DEVICES AND METHODS, which is a nonprovisional patent application of U.S. Provisional Patent Application No. 62/940,596, filed Nov. 26, 2019, and titled INFUSION AND BLOOD COLLECTION DEVICES AND METHODS, all of which are incorporated herein by reference.

FIELD OF THE INVENTION

The present invention relates to an infusion and blood collection device. In particular, the present invention is directed to an infusion and blood collection device that allows clean blood collections via an angiocatheter previously installed to administer intravenous fluids. The present invention is also directed to a method of using the infusion and blood collection device to draw blood from a patient via a previously installed angiocatheter.

DESCRIPTION OF RELATED ART

U.S. Pat. No. 3,610,226 to Albisser discloses a double lumen cannula instrument for the withdrawal of blood over a prolonged period of time. The instrument includes an inner lumen for withdrawing blood and an outer lumen for introducing an anticoagulant diluent. The relative locations of the openings for the inner and outer lumen permit the mixing of the diluent with the withdrawn blood.

U.S. Pat. No. 5,374,245 to Mahurkar discloses an extruded reinforced multiple-lumen catheter for use in medical applications where fluids must flow simultaneously to and from a patient. Blood is withdrawn for a medical procedure (for example, dialysis) from the patient through one passageway and returned to the patient through another passageway spaced from the first passageway.

U.S. Pat. No. 5,607,401 to Humphrey discloses augmented polymeric hypodermic needles and lancets. The polymeric needles and lancets are stiffened by augmenting means, which includes a slidable guard or foam insert so that they are able to pierce the skin. Without the augmenting means, it is not possible for the polymeric hypodermic lancet to pierce the skin.

U.S. Pat. No. 5,637,399 to Yoshikawa et al. discloses an extruded synthetic resin needle that is reinforced with combustible fibers. The needle provides a single path administering or withdrawing fluids from a patient.

The prior art described above does not provide for a catheter assembly that is capable of prolonged insertion in the patient for both the simultaneous administering of intravenous fluids and the periodic withdrawal of blood without mixing the intravenous fluid with the withdrawn blood.

U.S. Pat. No. 6,758,835 to Close et al. discloses a micro-injection molded disposable needle assembly having more than one passageway formed therein to permit the simultaneous drawing and administering of fluids through separate passageways. The micro-injection molded disposable assembly includes one or more sensors disposed therein for measuring and monitoring one or more desired body or surrounding environmental conditions. It also discloses a method of forming the disposable needle from an elastomeric material using micro-injection molding.

The invention herein is partly an extension of the device and method disclosed in U.S. Pat. No. 6,758,835 to Close et al. Accordingly, the disclosure of U.S. Pat. No. 6,758,835 is incorporated herein by reference in its entirety.

The devices described in the above prior art focus primarily on the catheter portions of needle assemblies that are capable of prolonged insertion in patients for both the simultaneous administering of intravenous fluids and the withdrawal of blood without mixing the intravenous fluid with the withdrawn blood.

Unlike the above prior art, the invention herein does not focus primarily on the catheter portion of the needle assembly. Instead, it provides a device that may be inserted between a standard, previously installed intravenous (IV) catheter (for example, a peripheral venous catheter) and a standard IV infusion line, and permits the performing of clean blood collections without interrupting the administering of IV therapy to the patient. For example, IV infusion pumps are typically stopped for 30 seconds or more for any blood collection obtained from the peripheral catheter and the connection between the IV catheter and infusate line are disconnected in order to pull the blood sample through the IV catheter and avoid infusate mixing with the blood collection that can cause erroneous results. If the IV infusion pump is not stopped and a downstream valve (for example, a 2-, 3-, or 4-way stop cock valve) is used to stop the infusate administration, then a pump alarm is set off, requiring staff attention because the line is considered occluded. Such fluid infusion restriction alarms on IV infusion pumps are typically triggered when the fluid being infused increases to over 10 psi. Providing a device that avoids interruption of the IV therapy prevents stopping the IV infusion pump or triggering an infusion restriction alarm. Further, the device herein has the purpose of reducing the complexity of the flow transfer portion of commonly used infusates and blood collection devices. Thus, whereas in some of the above prior art the pressure is sensed and controlled actively to ensure a clean blood collection, in the instant invention, the pressure can be controlled passively, or alternatively or additionally, actively.

When a patient is admitted into a hospital, an emergency room, or some other medical facility, in the vast majority of cases the patient receives an IV catheter of one kind or another. In some instances, the IV catheter is put in place right away upon admission to administer a needed therapy to the patient. In other instances, the IV catheter is put in place simply for risk management reasons, so as to have the catheter ready in case the medical care providers need to quickly administer medications or fluids to the patient. The cannula portion of the IV catheter is placed into a blood vessel, typically in the forearm, hand, or another location in the patient's body (that is, any animal body, for example, a human, canine, feline, equine, etc.), and the connection portion of the IV Catheter to allow IV infusion is typically secured to the outside of the patient's body with any of a variety of available tapes, bands, straps, or other means.

The typical hospital stay for a patient, on average, is around three days, during which it is reported that two or more sets of laboratory tests per day may be carried out on average. This means that at least twice a day a medical technician would have to subject the patient to a blood collection, which is then sent to the laboratory for testing and/or analysis. Usually if the patient already has a catheter strapped in place in one arm via which medications or fluids are being administered, the medical technician would have to use the patient's other arm or another part of the patient's body to perform blood collections. This means that, during a patient's 3-day average hospital stay, there are at least six occasions for the patient to be repeatedly stuck with a needle, which translates into at least six occasions for potential infections to start, hematomas, missed sticks, and skin irritation from tapes and other means. Furthermore, especially in situations involving pediatric patients, hemophiliac patients, HIV patients, patients with dementia and/or similar conditions, and/or other agitated patients who may suffer from fear of needle pricks, or having other elevated risks relating to additional needle insertions, the patient may be subjected to trauma on at least six occasions during their hospital stay, making the blood collection process difficult or otherwise risky.

Moreover, in some situations, the medical technician may use a catheter already installed into the patient's body to draw blood for testing. In those situations, the technician typically has to temporarily discontinue administration of medications or fluids, and perform a lengthy, drawn-out series of flushing steps to guard against incidental contamination of the blood sample with residual IV solutions, medications or fluids, and ensure that the blood sample is clean. Without such flushing steps, a blood sample may, for example, be diluted with a residual IV solution, leading to erroneous test results. Likewise, for example, contamination of the blood sample with a residual IV solution that contains sodium and/or potassium compounds, would result in false test data showing higher concentrations of these compounds.

SUMMARY

As will become apparent in the following disclosure, it is believed that the device and method of the invention described herein provide the advantage of alleviating and solving all of the foregoing blood-draw problems and issues. The device herein takes advantage of an already installed IV catheter port in a patient's body and provides a simple procedure to perform clean drawing of blood without interrupting the administration of IV therapies after initial installation of the catheter. The device optionally includes passive control of the blood collection volume flow rate to prevent contamination of the collected blood draw with the IV therapy fluid being simultaneously infused through the catheter. The device herein is simply installed by inserting it into the IV catheter line already installed into the patient and makes the procedural steps of drawing blood samples almost automatic. Furthermore, the device herein has the advantage of using the vacuum within a standard blood collection container, such as a Vacutainer® (trademark of Becton, Dickinson and Company, of Franklin Lakes, New Jersey) or Vacuette® (trademark of Greiner Bio One, of Monroe, North Carolina) tube, as the driving mechanism for drawing the blood sample from the patient.

In an illustrative embodiment of the device (with distal/proximal references to the device, not the patient's body), a medical tube (for example, a microlumen) is inserted coaxially through and protrudes distally out from the distal end of another medical tube (for example, a catheter) which is inserted into a patient. The microlumen and catheter are in fluid communication with a diverter valve and valve housing. The valve housing is supplied with IV therapy fluid from an infusion line and provides selective operation in an infusion/non-collection mode and an infusion/collection mode. In the infusion/non-collection mode, IV therapy fluid is provided to both the microlumen and the catheter. In the infusion/collection mode, a blood collection component, for example, a vacuum collection tube holder coupled to the collection body, receives blood from the catheter and the microlumen simultaneously continues to provide IV therapy fluid to the patient.

The protrusion length and blood collection flow rate are of significant importance to the invention herein, in order to prevent mixing, and thus contamination, of the drawn blood with the IV fluids in the infusion/collection mode. For example, the difference in pressures between a vacuum blood collection tube and a typical patent's vein pressure is approximately 2 orders of magnitude difference. For example, the tube vacuum can be as much as about 700 mmHg of vacuum and the vein pressure can be about 7 mmHg. Thus, the mixing of collected blood with IV fluids at the point of collection in the vein is prevented by a combination of 1) the device limiting the flow rate of blood collection drawn from the vein and into the catheter and 2) the distal end of the microlumen used to simultaneously infuse infusate into the vein is sufficiently distal in the vein of the distal end of the IV catheter where blood is drawn from the vein.

While the illustrative embodiment of the instant invention is directed to an angiocatheter (that is, an IV catheter), it is to be understood that, as contemplated herein, the invention may be applicable to other catheters known in the art as well, such as peripherally inserted cardiac catheters, central catheter, and the like.

It is an object of the present invention to provide an infusion and blood collection device that allows clean blood collections from a patient via a previously installed catheter, such as a Peripheral Venous Catheter, otherwise known as an angiocatheter, without interrupting the administration of intravenous therapies after the initial installation.

It is another object of the present invention to provide an infusion and blood collection device that allows clean blood collections from a patient via a previously installed catheter, without having to resort to repeatedly sticking a patient with a needle at another location of their body away from the already installed catheter.

It is another object of the present invention to provide an infusion and blood collection device that allows clean blood collections from a patient via a previously installed catheter, without exposing the patient to a higher risk of infection from repeated and multiple needle pricks.

It is another object of the present invention to provide an infusion and blood collection device that allows clean blood collections from a patient via a previously installed catheter, wherein the patient is a pediatric patient, a hemophiliac patient, a HIV patient, a patient with dementia and/or a similar condition, and/or any patient who may be agitated or suffer from fear of needle pricks, or having other elevated risks relating to additional needle insertions.

It is another object of the present invention to provide an infusion and blood collection device that allows clean blood collections from a patient via a previously installed catheter, without the need to temporarily discontinue administration of medications or fluids, and performing a lengthy, drawn-out series of flushing steps to guard against incidental contamination of the blood sample with residual IV solutions, medications or fluids.

It is another object of the present invention to provide an infusion and blood collection device that allows clean blood collections from a patient via a previously installed catheter, in such a manner so as to reduce the time and patient care demands of hospital staff.

The present invention relates to a blood-draw device and method that is used in conjunction with a pre-installed peripheral venous catheter/IV infusion line in a patient. An advantage of the device and method is being able to draw blood from the previously installed catheter without the need to interrupt IV flow.

Another advantage of the device and method is the reduction in the number of venipunctures that have to be performed on a patient. This provides numerous potential advantages such as reduction in potential infection causing events, reduction in patient anxiety, reduction in time and patient care demands on the hospital staff, and reduction in disposal of bio-hazardous blood collection needle sets.

Another advantage is having the blood collection access port of the device covered so as to prevent tampering with the port and bacterial transfers from the outside environment, which may either contaminate or damage the port, which in turn may lead to bodily injury.

One illustrative embodiment of an infusion and blood collection device for use with a patient catheter and an IV infusion line providing IV therapy fluid to the patient comprises a blood collection component having a draw inlet; a housing having an actuator and an IV infusion inlet coupled to the IV infusion line, the actuator enabling at least an infusion/non-collection mode of operation and an infusion/collection mode of operation for the device; a microlumen collocated with the patient catheter, the microlumen in fluid communication with the IV infusion inlet; a blood collection channel in fluid communication with the catheter, the blood collection channel directly accessible by the draw inlet of the blood collection component; and wherein in the infusion/non-collection mode the actuator fluidly couples the blood collection channel with the IV infusion inlet, and in the infusion/collection mode the actuator fluidly isolates the blood collection channel from the IV infusion inlet.

The blood collection channel can be self-flushing with IV therapy fluid in the infusion/non-collection mode. The device can further comprise a passive restriction device limiting the volume flow rate of blood drawn by the catheter in the infusion/collection mode, thereby preventing mixing of the blood draw with IV therapy fluid provided through the microlumen. The blood collection component can be releasably attachable to the housing. The actuator can be actuated to the infusion/collection mode by engagement of the blood collection component with the housing and the actuator is actuated to the infusion/non-collection mode by disengagement of the blood collection component with the housing. The engagement can include axial and rotational movement of the blood collection component relative to the housing, the axial movement placing the draw inlet in fluid communication with the blood collection component and the rotation movement operating the actuator.

The draw inlet can include a needle positionable to extend into the blood collection channel in the infusion/collection mode. The blood collection component can fluidly couple a vacuum blood collection tube to the blood collection channel. The actuator can include a rotary valve. The rotary valve can be a two-way valve having two open ports and a third selective port, the valve defines at least a portion of the blood collection channel. The draw inlet of the blood collection component can be extendable through the third selective port into the portion of the blood collection channel defined by the rotary valve. The microlumen can extend past the distal end of the catheter such that a distal end of the microlumen is located distally beyond the distal end of the catheter. The microlumen can be threaded coaxially through the catheter. The patient catheter can include a fluid catheter connector. The housing can include a fluid head connector for coupling to the catheter connector. The microlumen can exit the housing from within the head connector. The blood collection channel can be in fluid communication with the head connector.

Another illustrative embodiment of an infusion and blood collection device for use with a patient catheter and an IV infusion line providing IV therapy fluid to the patient, comprises a blood collection component; a housing having an actuator and an IV infusion inlet coupled to the IV infusion line, the actuator enabling at least an infusion/non-collection mode of operation and an infusion/collection mode of operation for the device; a microlumen collocated with the patient catheter, the microlumen in fluid communication with the IV infusion inlet; a blood collection channel in fluid communication with the catheter; and a passive restriction device limiting the volume flow rate of blood drawn by the catheter in the infusion/collection mode, thereby preventing mixing of the blood draw with IV therapy fluid provided through the microlumen; and wherein in the infusion/non-collection mode the actuator fluidly couples the blood collection channel with the IV infusion inlet, and in the infusion/collection mode the actuator fluidly isolates the blood collection channel from the IV infusion inlet.

The passive restriction device can be a thin, elongate tube fluidly coupling the blood collection component and blood collection channel. The microlumen can be positioned coaxially within the catheter and the distal end of the microlumen extend distally beyond the distal end of the catheter. The blood collection component can fluidly couple a vacuum blood collection tube to the blood collection channel. The blood collection component can be releasably attachable to the housing. The actuator can be actuated to the infusion/collection mode by engagement of the blood collection component with the housing and the actuator can be actuated to the infusion/non-collection mode by disengagement of the blood collection component with the housing. The engagement can include axial and rotational movement of the blood collection component relative to the housing, the axial movement placing the elongate tube in fluid communication with the blood collection component and the rotation movement operating the actuator.

Yet another illustrative embodiment of an infusion and blood collection device for use with a patient catheter and an IV infusion line providing IV therapy fluid to the patient, comprises a housing having an actuator and an IV infusion inlet coupled to the IV infusion line, the actuator enabling at least an infusion/non-collection mode of operation and an infusion/collection mode of operation for the device; a microlumen positionable coaxially through the patient catheter, the distal end of the microlumen extending distally beyond the distal end of the catheter the microlumen, and the microlumen in fluid communication with the IV infusion inlet; a blood collection channel in fluid communication with the catheter; and a blood collection tube holder releasably attachable to the housing and having a draw needle, the draw needle selectively in fluid communication with the blood collection channel in the infusion/collection mode, and the draw needle providing a restriction limiting the volume flow rate of blood drawn by the catheter in the infusion/collection mode, thereby preventing mixing of the blood draw with IV therapy fluid provided through the microlumen; and wherein in the infusion/non-collection mode the actuator fluidly couples the blood collection channel with the IV infusion inlet, and in the infusion/collection mode the actuator fluidly isolates the blood collection channel from the IV infusion inlet.

BRIEF DESCRIPTION OF THE DRAWINGS

The detailed description particularly refers to the accompanying figures in which:

FIG. 2A is a schematic diagram of the fluid system of the device of FIG. 1 in an infusion/non-collection mode of operation;

FIGS. 2B and 2C is a schematic diagram of the fluid system of the device of FIG. 1 in an infusion/collection mode of operation.;

FIG. 3 is a perspective exploded view of the valve housing portion of the device of FIG. 1;

FIG. 4 is a perspective exploded view of the blood collection tube holder portion of the device of FIG. 1;

FIG. 7A is perspective assembly view of the device of FIG. 1 placed with an IV infusion line and a Peripheral Venous Catheter, the device in an infusion/non-collection mode and the tube holder being prepared to be coupled with the valve housing;

FIG. 7B is a cross-sectional view of the valve housing and separated tube holder taken along sectional cutting plane line 7B-7B, shown in FIG. 7A, and with the device in the infusion/non-collection mode;

FIG. 7C is a cross-sectional view of the valve housing taken along sectional cutting plane line 7C-7C, shown in FIG. 7B, and with the device in the infusion/non-collection mode;

FIG. 8A is perspective assembly view of the device of FIG. 1, the device in an infusion/non-collection mode and the tube holder being coupled with the valve housing and not yet rotated;

FIG. 8B is a cross-sectional view of the valve housing and coupled tube holder taken along sectional cutting plane line 8B-8B shown in FIG. 8A, and with the device in the infusion/non-collection mode;

FIG. 8C is a cross-sectional view of the valve housing taken along sectional cutting plane line 8C-8C shown in FIG. 8B, and with the device in the infusion/non-collection mode;

FIG. 9A is perspective assembly view of the device of FIG. 1, the device actuated to the infusion/collection mode and the tube holder being coupled with the valve housing and rotated, and a blood collection tube coupled with the tube holder;

FIG. 9B is a cross-sectional view of the valve housing and coupled tube holder and collection tube taken along sectional cutting plane line 9B-9B, shown in FIG. 9A, and with the device in the infusion/collection mode;

FIG. 9C is a cross-sectional view of the valve housing taken along sectional cutting plane line 9C-9C, shown in FIG. 9B, and with the device in the infusion/collection mode;

DETAILED DESCRIPTION OF THE ILLUSTRATIVE EMBODIMENTS

Figure 1:
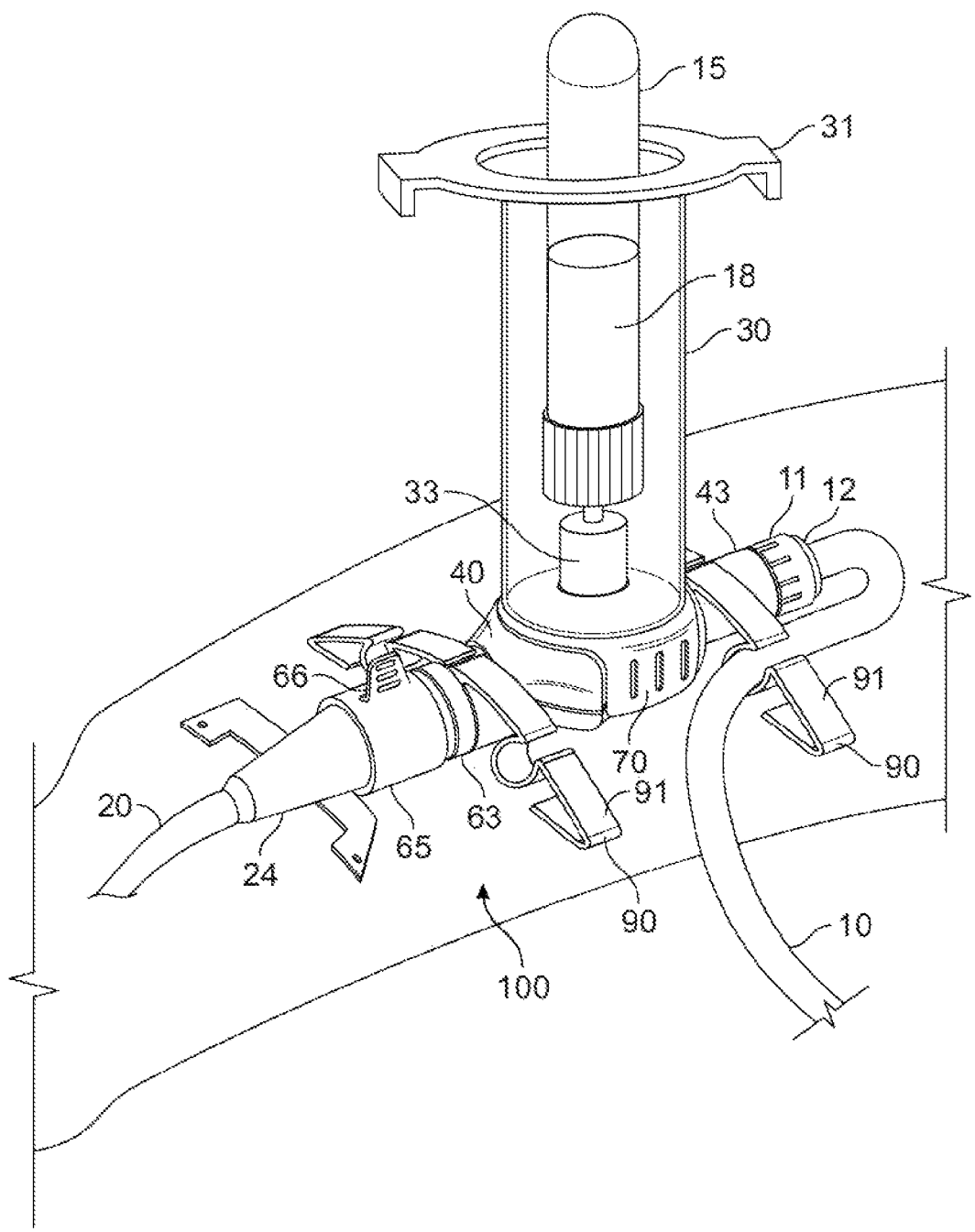
FIG. 1 is a perspective assembly view of a first illustrative embodiment of an infusion and blood collection device as used with an IV infusion line and a Peripheral Venous Catheter.
Figure 5:
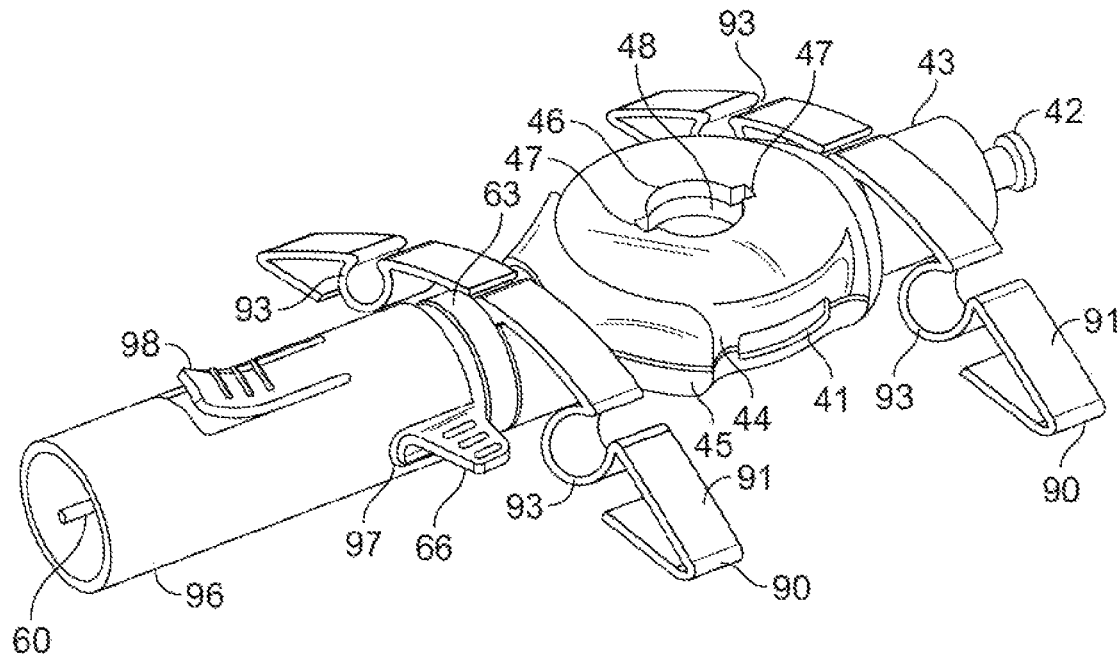
FIG. 5 is a top perspective assembly view of the device of FIG. 1 before use.

For the purposes of promoting an understanding of the principles of the disclosure, reference will now be made to one or more embodiments, which may or may not be illustrated in the drawings, and specific language will be used to describe the same. It will nevertheless be understood that no limitation of the scope of the disclosure is thereby intended; any alterations and further modifications of the described or illustrated embodiments and any further applications of the principles of the disclosure as illustrated herein are contemplated as would normally occur to one skilled in the art to which the disclosure relates. At least one embodiment of the disclosure is shown in great detail, although it will be apparent to those skilled in the relevant art that some features or some combinations of features may not be shown for the sake of clarity.

Any reference to "invention" within this document is a reference to an embodiment of a family of inventions, with no single embodiment including features that are necessarily included in all embodiments, unless otherwise stated. Furthermore, although there may be references to benefits or advantages provided by some embodiments, other embodiments may not include those same benefits or advantages, or may include different benefits or advantages. Any benefits or advantages described herein are not to be construed as limiting to any of the claims.

Likewise, there may be discussion with regards to "objects" associated with some embodiments of the present invention, it is understood that yet other embodiments may not be associated with those same objects, or may include yet different objects. Any advantages, objects, or similar words used herein are not to be construed as limiting to any of the claims. The usage of words indicating preference, such as "preferably," refers to features and aspects that are present in at least one embodiment, but which are optional for some embodiments.

Specific quantities (spatial dimensions, temperatures, pressures, times, force, resistance, current, voltage, concentrations, wavelengths, frequencies, heat transfer coefficients, dimensionless parameters, etc.) may be used explicitly or implicitly herein, such specific quantities are presented as examples only and are approximate values unless otherwise indicated. Discussions pertaining to specific compositions of matter, if present, are presented as examples only and do not limit the applicability of other compositions of matter, especially other compositions of matter with similar properties, unless otherwise indicated.

Referring to FIGS. 1-10 in the Drawings section, these figures show a first illustrative embodiment of an infusion and blood collection device, system and/or methods 100 of the invention herein, The device 100 is illustratively shown as used, coupled between a standard IV infusion line 10 and a standard catheter 20, for example, a peripheral venous catheter, placed in a vein of a patient's arm or hand. An example of such a standard catheter 20 is the shielded IV catheter product number 381534, also known as the BD Insyte Autoguard Winged 20-gauge catheter, available from Becton, Dickson and Company (BD), of Sandy, Utah.

It is understood that in a typical situation requiring venous catheterization of a patient in, for example, an emergency room or hospital, the IV infusion line 10 and the catheter 20 would be connected directly together via a releasable fluid connector, typically a Luer Lock type connector having a male portion (not shown) at a proximate end 24 of the catheter 20, and a female connector 11 portion at the proximate end 12 of the IV infusion line. The IV infusion line 10 is typically connected on the opposite, distal end to an IV therapy bag (not shown) and/or infusion pump (not shown), and a distal end 22 of the catheter 20 is inserted into a patient blood vessel, for example, in the patient's arm or hand as shown in FIGS. 1 and 2A-2C, for example, using a sharp insertion needle introducer (not shown), the needle of which is extended through and extends beyond the distal end 22 of the catheter 20, and is extracted from the catheter after placement of the distal end into a patient's vein 23. An example of such an introducer is product number 384010, also known as the BD Introsyte Autoguard Shielded Introducer, available from Becton, Dickson and Company (BD), of Sandy, Utah. After placement of the catheter 20, the infusion and blood collection device 100 of the present invention is simply installed in between the IV infusion line 10 and the catheter 20, coupled via the connectors 11 and 65, as is discussed below.

Figure 6:
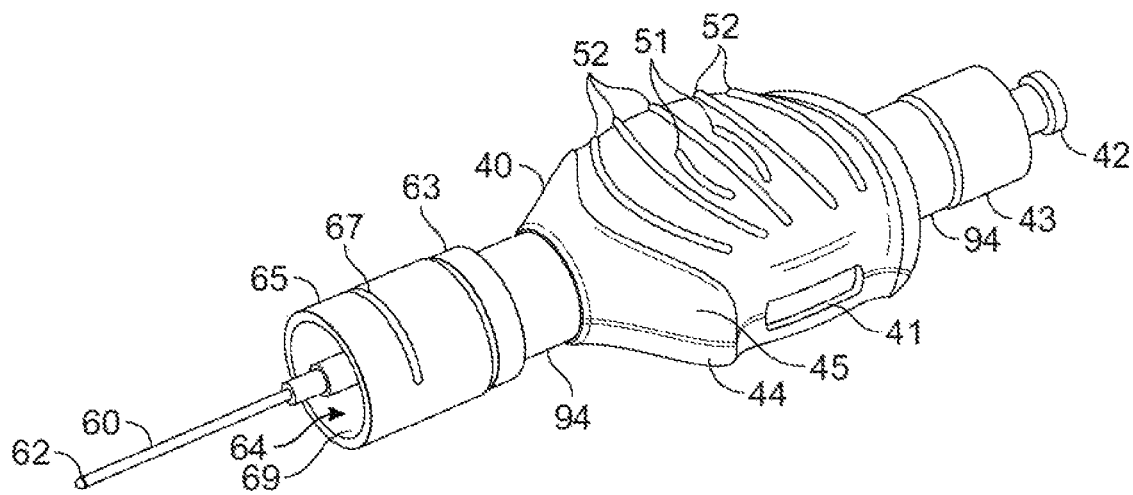
FIG. 6 is a bottom perspective assembly view of the device of FIG. 1 before use and with the protective cap removed from overtop the microlumen.

The illustrative embodiment of the infusion and blood collection device 100 of the present invention comprises the following main components, depicted in FIGS. 1, 3 and 6: a collection tube holder 30 for receiving a standard vacuum collection tube 15, a valve housing 40 enclosing a valve 80 and including an intravenous infusion (IV) inlet 43 and a catheter head 63, a shroud 70 for coupling the tube holder 30 to the valve housing 40, and optional retaining supports 90 for securing an IV infusion line 10 and the valve housing 40 to a patient's arm.

Materials from which the tube holder 30, valve housing 40, shroud 70, valve 80, and retaining supports 90 can be formed, include, for example, medical grade plastics and structural polymer material such as ABS, Polyurethane, Polycarbonate, PBT, PEI, PEEK, Polypropylene, PET, and the like. For example, tube holder 30, valve housing 40, and shroud 70 can be formed from Polycarbonate and valve 80 can be formed from Polypropylene.

The intravenous infusion inlet 43 includes a separate or integrally formed male connector 42 for fluid coupling with the female connector 11, for example a Luer Lock fitting, of IV infusion line 10. The catheter head 63 includes a female connector 65, for example a Luer Lock fitting, for fluid coupling with the catheter 20. The catheter head 63 also includes an intravenous infusion microlumen 60, which is fluidly coupled to IV infusion channel 58, and a blood collection channel 54, the outlet 64 of which is fluidly coupled to catheter 20 (FIGS. 6 and 7C).

FIGS. 2A-2C illustrate schematic diagrams of an illustrative fluid system 101 of the device 100 according to the present invention. With reference to the device 100, a blood collection channel 54 and an infusion channel 58 extend between IV inlet 43 and catheter head 63. As described above, the catheter head 63 is coupled to an IV catheter 20, which is earlier placed in a peripheral vein 23 of a patient, and the catheter head 63 also includes the microlumen 60. Upon coupling of the catheter head 63 with the connector 24 of the catheter 20, the microlumen 60 is inserted coaxially within the interior of the catheter 20. For reasons more fully described below, the relative lengths of the catheter 20 and the microlumen 60 are such that a distal end 62 of the microlumen 60 protrudes from and extends distally beyond the distal end 22 of the catheter 20, thus extending axially farther along and within the patient's vein 23, as shown in FIG. 2C. The microlumen 60 is in fluid communication with the infusion channel 58. The catheter 20, or more specifically for the device 100, the radial space between the outside surface of the microlumen 60 and the interior surface of the catheter 20, is in fluid communication with the blood collection channel 54 via outlet 64 (FIGS. 6 and 7C). A microlumen 60 having at least a minimum amount of rigidity while remaining flexible enough to remain safely within the catheter 20 and vein 23 has been found to be advantageous in threading the microlumen 60 into the connector 24 and catheter 20. For example, a microlumen formed from unbraided and uncoated polyimide has been found to possess acceptable properties. As another example, a microlumen formed from unbraided and coated polyimide, such as product code 165-III available from Microlumen of Oldsmar, Florida, has been found to possess acceptable properties. And as yet another example, a microlumen formed from braided and coated (or uncoated) polyimide may also possess acceptable properties.

Advantageously, the device 100 provides selective operation in an infusion/non-collection mode and an infusion/collection mode. As shown in FIG. 2A, in the infusion/non-collection mode, IV fluid 14 (that is, any fluid entering a body) is provided simultaneously from IV inlet 43 to each of the infusion channel 58, including the microlumen 20, and the blood collection channel 54, including catheter 20, of the fluid system 101. In the infusion/non-collection mode of operation, IV fluid 14 flows into the fluid system at the IV inlet 43 and simultaneously exits within the vein 23 at the respective distal ends 22 and 62 of the catheter 20 and microlumen 60.

In contrast and as shown in FIGS. 2B and 2C, in the infusion/collection mode of operation, the blood collection channel 54 of the device 100 is closed off from the IV inlet 43 and thus from the supply of IV fluid 14. The fluid isolation of the IV inlet 43 from the blood channel 54 can be implemented by any one of various mechanical or electro-mechanical actuators known in the art. For example, in the illustrative first embodiment of the device 100, a three port (including one selectively sealed draw port 81) two-way rotary valve 80 (FIG. 3) rotates from a non-collection valve position 83a in which the valve passage 84a (FIGS. 2A and 7C) is fluidly coupled to both the IV inlet 43 and the blood channel 54, to a collection valve position 83b in which the valve passage 84a (FIGS. 2B and 9C) is fluidly isolated from the IV inlet 43 but remains fluidly coupled to the blood channel 54. The valve passage 84a thus forms a portion of the blood collection channel 54 in valve position 83b. As used herein, an "actuator," an example of which being a "valve," refers to a device that affects fluid flow, such as starting, stopping, or otherwise regulating the flow of fluid.

As shown in FIG. 2B, once the blood collection channel 54 is closed off from the IV fluid 14, a vacuum blood collection tube is fluidly coupled with the blood collection channel 54 via an outlet, for example, a needle channel 84b. The vacuum of the collection tube 15 draws blood 18 into the catheter 20, or more specifically from the space between the catheter 20 and microlumen 60 as shown in FIG. 2C, through the blood collection channel 54 and into the collection tube 15. The collection of blood 18 occurs simultaneous with and without interruption of the infusion of IV therapy fluid 14 through the infusion channel 58, exiting into the vein 23 of the patient at the distal end 62 of the microlumen 60.

As blood 18 is drawn from the vein 23 into the catheter 20, the fluid entering the collection tube 15 initially will be IV fluid 14, and then a mixture of IV fluid 14 and blood 18, and then only blood 18. Thus, the first collection tube 15 filled from the blood collection channel 54 is discarded and a subsequently filled blood collection tube 15 that contains only blood 18 and no IV fluid 14 are retained. After a sufficient sample of blood 18 is obtained from the device 100, the collection tube 15 is fluidly uncoupled from the blood collection channel 54, and if desired, subsequent collection tubes 15 are coupled, filled, and uncoupled, and then the rotary valve 80 is returned to the non-collection valve position 83*a*, fluidly recoupling the blood collection channel 54 with the therapy fluid 14 from the IV inlet 43, thereby again providing the infusion/non-collection mode of FIG. 2A in which IV fluid 14 is simultaneously provided to each of the catheter 20 and the microlumen 60.

Referring to FIG. 2C, the distal end 62 of the microlumen 60 is shown protruding distally from within the distal end 22 of the catheter 20. The length of the distal portion 62 of the microlumen 60 that protrudes from the distal end 22 of the catheter 20 is illustratively around 10 mm, but it can vary depending on various fluid dynamic features of the device 100, including the type and model of catheter 20 and microlumen 62 used, and the desired blood collection flow rate. The protrusion length and blood collection flow rate are of significant importance to the invention herein, in order to prevent mixing at distal end 22, and thus contamination, of the drawn blood 18 with the IV fluids 14, as will become apparent from the discussion below. For example, a typical IV catheter 20 is 18 or 20 gauge, and a microlumen 60 providing the desired functionality when axially inserted within the catheter 20 is about 24 to 25 gauge.

Referring to FIG. 3, an exploded perspective view of the valve housing 40 is illustrated. Valve housing 40 includes a housing top 44 and a housing bottom 45 that together define a valve cavity 50, IV infusion channel portions 58*a* and 58*b*, and a blood collection channel 54. The valve housing 40 provides continuous fluid communication through infusion channel 58*a*, thus continuously providing IV fluid 14 presented at IV inlet 43 to each of the outlet 64 and the microlumen 60. The valve cavity 50 sealingly houses the rotary valve 80, which provides IV fluid 14 to blood collection channel 54 selectively in the non-collection mode of operation. For example, the valve member 82 may include a sealing ridge or other feature 85 that prevents seepage of fluids and the valve member 82 and/or valve cavity 50 may be coated with a sealing and/or lubricating material prior to assembly, for example silicone spray or gel, or may include an elastomeric sealing layer.

The rotary valve 80 includes a valve member 82 that defines a valve passage 84*a* having openings connecting to opposite sides of the valve housing (FIGS. 3 and 7C). The valve member 82 further defines a draw port 81 that is fluidly plugged by and retains septum 76 (FIG. 3) and tube holder engagement features 86 and 87 that will be described further below.

The draw port 81 at a bottom 77 of the septum 76 is fluidly coupled to the valve passage 84*a* by needle passage 84*b* (FIG. 7B). Referring to FIGS. 7B and 7C, when the valve 80 is enclosed within the assembled housing top 44 and housing bottom 45 and the valve 80 is in a non-collection position 83*a* (FIG. 7C) the valve passage 84*a* of the valve 80 fluidly couples the infusion channel portion 58*b* to the blood collection channel 54, supplying IV fluid 14 to the catheter head 63 and catheter 20. Referring to FIG. 9C, when the valve 80 is rotated to a collection position 83*b* the valve passage 84*a* of valve 80 is fluidly isolated from the infusion channel portion 58*b* yet remains in fluid communication with the blood collection channel 54, thus providing a path for blood 18 entering the distal end 22 of the catheter 20 to be supplied to the valve passages 84*a*, the needle channel 84*b* and the bottom 77 of the septum 76.

Referring to FIG. 4, the collection tube holder 30 provides an adaptor to couple a blood collection tube 15 to the valve housing 40, and also functions to actuate the valve 80 between the non-collection position 83*a* (FIG. 8C) for the infusion/non-collection mode of operation and collection position 83*b* (FIG. 9C) for the infusion/collection mode of operation. The tube holder 30 includes an insertion and rotation handle 31, a central tube receptacle 32, a tube stop 33 at the base of the receptacle, a draw port interface 36, and a draw needle 34. Referring to FIG. 7B, the draw needle 34 extends through the tube stop 33 and has a top end 34*a* extending above the tube stop 33 and upwardly into the tube receptacle 32. The draw needle 34 also extends downwardly below the tube stop 33 and within the central area 39 enclosed by the draw port interface 36. The draw port interface 36 functions in part to encircle and prevent injury from the sharp lower end 34*b* of the needle 34.

The tube holder interface 36 is configured to fit within an opening 46 in the valve housing 40 and engage with the valve 80 and housing 40 upon coupling the tube holder 30 and shroud 70 to the valve housing 40. In the first illustrative embodiment of the device 100, the engagement of the tube holder 30 with the valve housing 40 and the valve 80 provides axial positioning of the draw needle 34 and rotation of the valve 80. More specifically, the engagement axially extends the draw needle 34 through the septum bottom 77 and the needle channel 84*b* and into the valve passage 84*a*, as shown in FIG. 9B. Additionally, the engagement rotates the valve 80 and valve housing 40 from the infusion/non-collection valve position 83*a* to the infusion/collection valve position 83*b*. Optionally, mechanical features can be provided with the tube holder 30, housing 40, and/or the valve 80 so that mechanical detents or other sensory feedback is provided that indicated the range of limits of full rotation and/or axial translation to ensure proper use and operation.

Referring to FIGS. 3, 4 and 7B, the tube holder interface 36 defines various engagement features, including axial draw tabs 37, rotational slots 38, and a central area 39. The valve housing 40 defines various engagement features, including the opening 46, draw tab receivers 47, and draw ramps 48. The valve 80 defines various engagement features, including receiver 86 and rotational cogs 37. The function and interaction of the various engagement features will be described further below in the operation of the device 100.

The series of FIGS. 7A-7C, 8A-8C, 9A-9C, and 10A-10C illustrate the various steps and stages of the infusion/non-collection mode of operation, preparing the device 100 for a blood draw, drawing blood into collection tube(s) 15 in the infusion/collection mode of operation, and returning the device 100 to the infusion/non-collection mode of operation.

Referring to FIG. 7A, in the following illustrative use of the illustrative device 100, the installation of the infusion and blood collection device 100 for intravenous therapy of a patient is described. Prior to installation of the device 100, following standard techniques well-known in the art, the peripheral venous catheter 20 is typically inserted into a vein of the patient and the IV therapy tube 10 is connected via a Luer-type or other connection 11. To install the infusion and blood collection device 100 in-line with the catheter 20 so that clean blood samples can be periodically drawn from the patient via the catheter 20, the IV therapy fluid flow 14 through IV infusion line 10 is stopped, and the peripheral venous catheter 20 is disconnected from the IV infusion line 10. The valve housing 40 of the device is connected to the IV infusion line 10 by connecting the connector 11 to the inlet port 43 and the fluid flow 14 through the IV infusion line 10 is then restarted, and the IV fluid 14 (or for example, heparin) flowing into inlet port 43 fills both the blood collection channel 54 and the infusion channel 58 in the housing 40 until the IV fluid 14 flows from the catheter head 63, thus pushing all air from the channels 54 and 58. The protective cap 96 (FIG. 5) can be removed from the catheter head 63, exposing the microlumen 60, for example, by actuating release 98.

The catheter head 63 can then be attached to the catheter 20 (which, for example, has remained in the patient) by inserting the microlumen 60 all the way through the catheter 20 and tightening the Luer-type or other connector 65 onto the male catheter connector 63, thus allowing the IV therapy fluid 14 to infuse into the patient from both the catheter 20 and the microlumen 60. Advantageously, the valve housing 40 can be grasped from above and held in the palm while the release 98 is actuated, the microlumen 60 guided, and the connector 65 rotated by wing 66 all with the free thumb and/or forefinger of the hand holding the valve housing 40, freeing the other hand to apply pressure to the vein 23 to prevent blood flow through the catheter 20 from the uncoupling of the IV line connector 11 until the coupling of the device 100 connector 65. With the optionally retaining supports 90 coupled at clips 92 to valve housing receivers 94 (FIG. 3) as shown in FIG. 1, medical tape can be applied over surface 91 and around the patient's arm to hold the valve housing 40 in place. Advantageously, the valve housing 40 can include ridges or other protrusions defined by the housing bottom 45 to limit skin contact or risk of skin breakdown. Additionally, to allow drainage of any liquids entering the opening 46 when the tube holder 30 is not in place, and minimize the possibility of microbial growth, drainage channels 51 extending downward from within the opening 46 can be defined through the housing 40.

Alternatively and advantageously, the device 100 can also be installed in-line with the catheter 20 upon the catheter 20 first being placed and before an IV infusion line 10 is connected to the catheter 20. For example, as described above, the device 100 can be connected to the IV infusion line 10 and flushed of air with the IV fluid 14. Then, with the device 100 prepared, the peripheral venous catheter 20 can be placed into a vein of the patient and the catheter head 63 attached to the catheter 20 as described above.

Referring now to FIGS. 7A-7C, the device 100 is shown in the infusion/non-collection mode of operation after installation in-line with IV line 10 and the catheter 20. Specifically, the tube holder 30 and shroud 70 are uncoupled from the valve housing 40 and the rotary valve 80 is in the infusion/non-collection rotational position 83a (FIG. 7C) in which IV fluid 14 provided at the inlet 43 is simultaneously provided to each of the blood collection channel 54 and the infusion channel 58a, and thus simultaneously flows in the patient's vein 23 from each of catheter 20 and microlumen 60.

To prepare the device 100 for the infusion/collection mode of operation, an alcohol or other sterilizing swab is used to clean the septum 76 and the area within the opening 46 to remove any contaminates. Next the tube holder 30, without a blood collection tube 15 attached, is coupled to the valve housing 40. Specifically, the axial draw tabs 37 are rotationally aligned with the draw tab receivers 47 and the tube holder 30 is moved vertically downwards in the direction shown in FIGS. 7A and 7B, engaging the tabs 37 through the receivers 47 and into draw ramps 48 and engaging the side flanges 72 around the valve housing 40. The shroud 70 and the tube holder 30 is releasably retained to the valve housing 40 by the engagement of protrusions 71 into recesses 41 located on each side of the valve housing 40. Additionally, and as shown in FIGS. 8B and 8C, in this position, the lower end 34b of the draw needle 34 has not penetrated the septum 76 and the rotary valve 80 remains in the infusion/non-collection rotational position 83a. As shown in FIG. 8A, the flanges 72 can define friction elements such as ridges to facilitate holding the device 100 securely during the subsequent below steps.

To complete the axial translation of the lower end 34b of the draw needle 34 through the septum 76 and into the valve passage 84a, the tube holder 30 is rotated clockwise relative to the valve housing 40 as shown in FIG. 8A. Referring now to FIGS. 9B and 9C, showing the device 100 with rotation complete, rotation of the tube holder 30 rotates the draw tabs 37 within the draw ramps 48 of the housing 40. The draw ramps 48 spiral downward so that the rotation results in the tube holder interface 36 translating axially downward farther into the valve housing 40 to the position shown in FIG. 9B in which the lower end 34b of the draw needle 34 pierces the septum 76 and extends into the valve passage 84a. Additionally, rotation of the interface 36 with the tube holder 30 rotates the valve 80 since the cogs 87 are engaged within slots 38 of the interface 36. This rotation rotates the valve 80 to the infusion/collection position 83b shown in FIG. 9C, in which valve passage 84a (FIGS. 2B and 9C) is fluidly isolated from IV inlet 43 but remains fluidly coupled to the blood channel 54. Mechanical stops (not shown), for example, the ends of the draw ramps 48 contacted by the draw tabs 37 prevent over rotation of the valve 80 in the clockwise and counterclockwise directions.

Optionally, an initial length of the draw ramps 48 defined in the valve housing 40 and engaged by the draw tabs 37 can extend circumferentially without downward axially displacement in order to provide for some or all of the rotation of the valve 80 before subsequent axial translation of the interface 36 and needle 34, thus ensuring that the fluid connection between the lower needle end 34b and the valve passage 84a is not made until the valve passage 84a is closed off from the infusion channel portion 58b and thus from the supply of the IV fluid 14.

As shown in FIGS. 9A and 9B, once the blood collection channel 54 is closed off from the IV fluid 14, a vacuum blood collection tube 15 is fluidly coupled with the blood collection channel 54 via needle channel 84b and valve passage 84a. More specifically, in pushing a collection tube downward into tube receptacle 32 and against the tube stop 33 of the tube holder 30, the septum 16 of the collection tube 15 pushes the elastomeric needle cover 35 downward, exposing the upper needle end 34a allowing it to pierce the collection tube septum 16. The vacuum of the collection tube 15 draws blood 18 into the catheter 20, as shown in FIG. 2C, through the blood collection channel 54, valve passage 84a, needle 34, and into the collection tube 15.

Advantageously, the collection of blood 18 occurs simultaneous with and without interruption of infusion of IV therapy fluid 14 through infusion channel 58, exiting into the vein 23 of the patient at the distal end 62 of the microlumen 60. The collection tube 15 is uncoupled from the tube holder 30, and if desired, subsequent collection tubes 15 are coupled, filled, and uncoupled. With the lack of a vacuum, a passive fluid flow restriction provided by needle 34, and the elastomeric cover 35 again covering the upper end 34a of the needle 34, blood 18 will cease to flow through needle 34 with no collection tube 15 in place. For example, the flow restriction can be provided by the selected ID of the needle 34 as discussed further below, by crimping the needle 34 to a specific desired cross-sectional area, or by other mechanically passive means known in the art to limit flow.

Figure 10A:
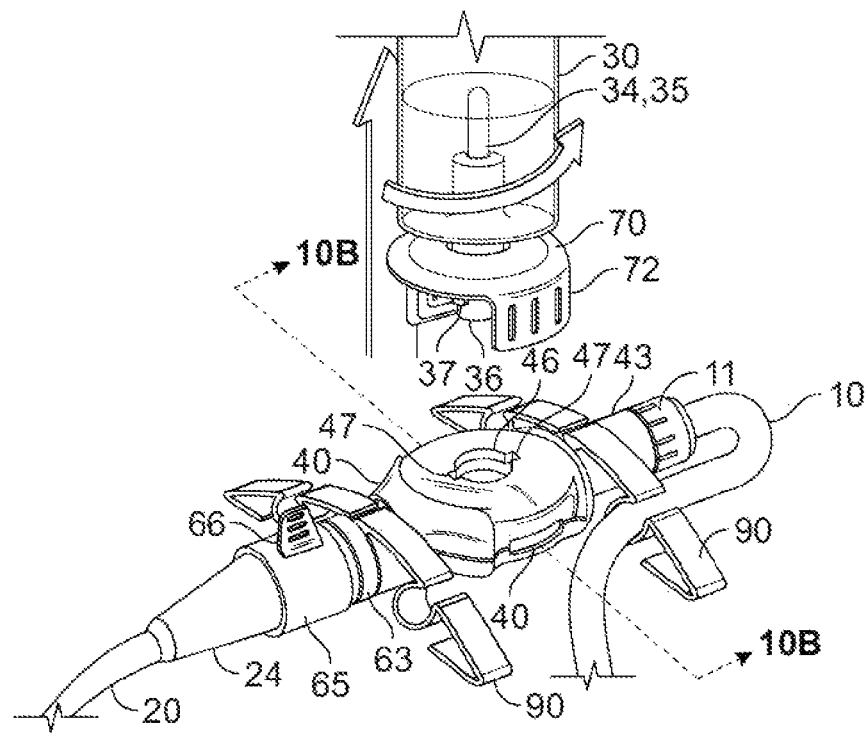
FIG. 10A is perspective assembly view of the device of FIG. 1, the device returned to the infusion/non-collection mode and the tube holder reverse-rotated and being uncoupled from the valve housing.
Figure 10B:
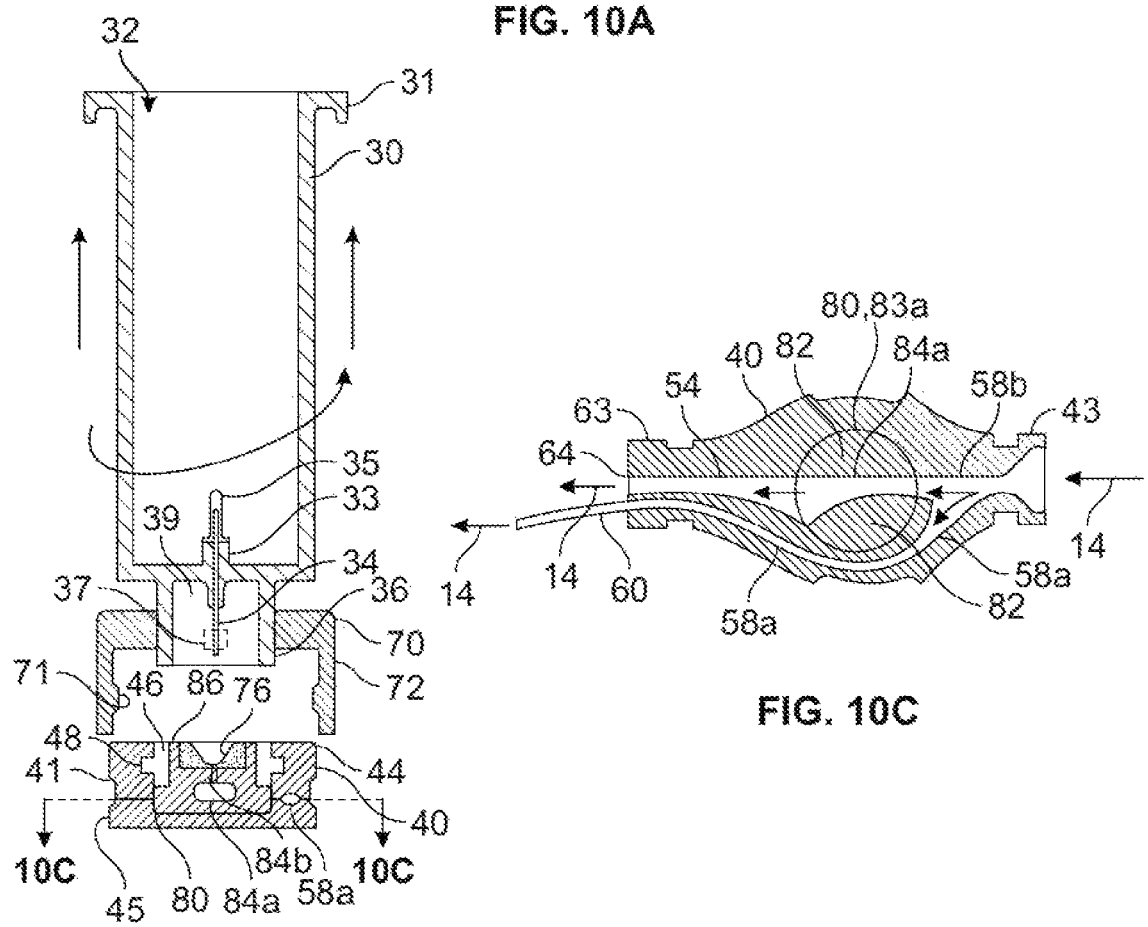
FIG. 10B is a cross-sectional view of the valve housing and coupled tube holder taken along sectional cutting plane line 10B-10B, shown in FIG. 10A, and with the device in the infusion/non-collection mode.
Figure 10C:
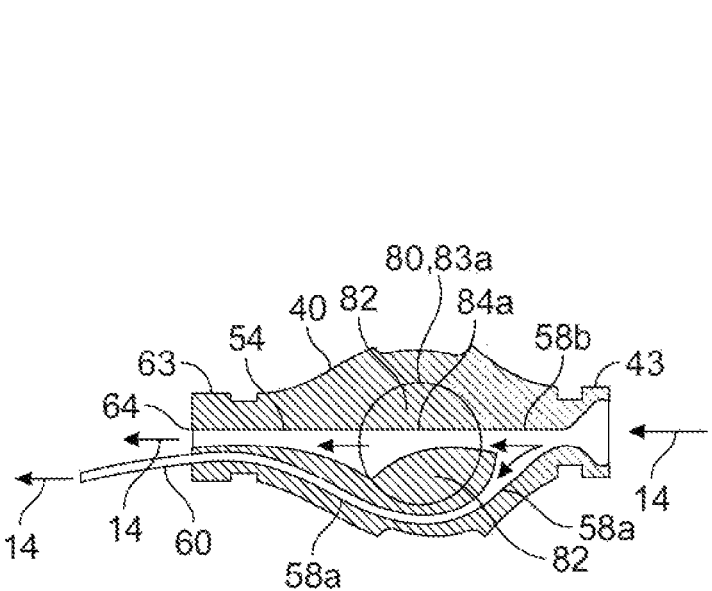
FIG. 10C is a cross-sectional view of the valve housing taken along sectional cutting plane line 10C-10C, shown in FIG. 10B, and with the device in the infusion/non-collection mode.

To return the device 100 to the infusion/non-collection mode of operation, as shown in FIGS. 10B and 10C, tube holder 30 is rotated counter-clockwise and the shroud 70 and tube holder 30 are separated from the valve housing 40, as shown in FIG. 10A. Rotating the tube holder 30 counter-clockwise returns the rotary valve 80 to the non-collection valve position 83a, fluidly recoupling the blood collection channel 54 with the therapy fluid 14 from the IV inlet 43.

Rotating the tube holder 30 counterclockwise also axially translates the interface 36 and needle 34 upwardly as the draw tabs 37 are spiraled upward within draw ramps 48. When the draw tabs 37 are again aligned with 47, the rotation is complete and interface 36 can be fully withdrawn from the opening 46 and the flanges 72 withdrawn from over the valve housing 40, as shown in FIG. 10B. Advantageously, the septum 76 is self-sealing, so that when the needle 34 is withdrawn and the IV fluid 14 flows through the valve passage 84a without escaping at the septum 76.

Again in the infusion/non-collection mode of operation shown in FIG. 10C, IV fluid 14 is again simultaneously provided to each of the catheter 20 and the microlumen 60, flushing the blood collection channel 54 of the blood 18 earlier drawn into it, and providing for continuing use of the device 100. Thus, advantageously, the blood collection channel 54, including the valve passage 84a, are self-flushing in that the return to the infusion/non-collection mode flushes any remaining blood through the catheter 20 with the flow of IV fluid 14, thus preventing any coagulation and potential blockage or other hazards of blood 18 associated with the device 100. Because the draw needle 34 associated with the tube holder 30 is not flushed, it is discarded and a new tube holder 30 is utilized when another blood draw from the patient is desired.

One aspect of the first embodiment of the invention herein relates to one of the novel features of the infusion and blood collection device 100 and method, which is the ability to perform clean blood collections while simultaneously providing the patient with IV therapy infusion, without interrupting the IV fluid flow. In one aspect, the device 100 is designed so as to prevent contamination of the blood 18 being drawn with the IV fluids 14. The ability of the device 100 to provide this function is due in part to two features of the device: 1) a protrusion of the tip of the microlumen 60 in the vein 23, an optimum minimum distance beyond the tip of the catheter 20 (see FIG. 2C); 2) a related restriction in the flow in the blood 18 being collected when the rotary valve 80 is rotated to the collection position 83b.

In an illustrative embodiment of these foregoing features, for example, the distal tip 62 of microlumen 60 extends 10 mm beyond the distal tip 22 of the catheter 20, paired with a restriction in the blood collection channel 54 to reduce the blood collection flow rate to 30 ml/min or less, provides sufficient protection against the IV fluids 14 flowing out from the distal tip 62 of the microlumen 60 being drawn toward and mixed in with the blood 18 being drawn into the distal tip 22 of the catheter 20 for collection in the collection tube 15.

As contemplated herein, it is to be understood that both the length of the protrusion of the tip of the microlumen relative to the tip of the catheter, and the degree of restriction of blood flow 18, may vary upward or downward depending on various factors such as, for example, the particular gauge of catheters 20 and 60 being used, the vacuum pressure in the particular collection tube 15, the venous or arterial location of the catheter 20 in the patient, and the rate of infusion of IV therapy fluid 14 out the microlumen 60. Thus, for example, with a protrusion length shorter than 10 mm, the flow rate would correspondingly have to be further restricted and decreased, and with a protrusion length longer than 10 mm, the flow rate may be increased correspondingly.

In regard to the restriction of blood flow 18 to reduce the blood collection flow rate to the point that the IV fluid flow is not reversed in the vein and drawn into the blood collection catheter, this restriction can be accomplished in various ways known in the art and at various locations along the path of the flow of the blood 18 between the distal end 22 of catheter 20 and the blood collection tube 15, either active restriction device, passive restriction device, or a combination of active and passive restriction devices. In the above illustrative embodiment of the device 100, the restriction in flow rate is made passively via the choice of the gauge of the penetration needle 34 that penetrates the end of the collection tube, thus a needle is selected having a sufficiently narrow internal diameter to provide the required limit to blood flow rate. In the illustrative device 100 with the distal end 62 of the microlumen 60 extending 10 mm beyond the distal end 22 of catheter 20, a restriction limiting the flow rate to about 30 ml/minute provides the desired lack of contamination of the blood sample collected. This desired restriction is passively provided by using a penetration needle 34 having a gauge of about 24, e.g., having an ID of about 0.3 mm (0.012 in). For example, such a needle 34 can be cut from a length of stainless steel 304 hypodermic round tubing stock, for example, part number B00137QIWS, available from Amazon.com, LLC, of Seattle, Washington The volume flow rate (Q) of the blood 18 is driven by the change in pressure ($\Delta P$) for the blood 18 between the patient and the collection tube 15, and most notably in the illustrative embodiment of the device 110, at the point of passive restriction in the blood flow 18, the draw needle 34. In order to specify a needle gauge that will limit the volume flow rate (Q) to the desired magnitude, for example, about 30 ml/min or less for the illustrative embodiment, the fluid dynamic principles for laminar flow with an applied force and no-slip boundary condition between a desired blood volume flow rate (Q) and a pressure gradient ($\Delta P$) can be used. This relationship is represented in the Hagen-Poiseuille equation which is $Q = \pi a 4 \Delta P / 8 \rho \mu L$, where a, L, $\rho$, $\mu$ are in this example, the interior radius and length of the needle 136, and the density and viscosity of the blood, respectively.

Figure 11:
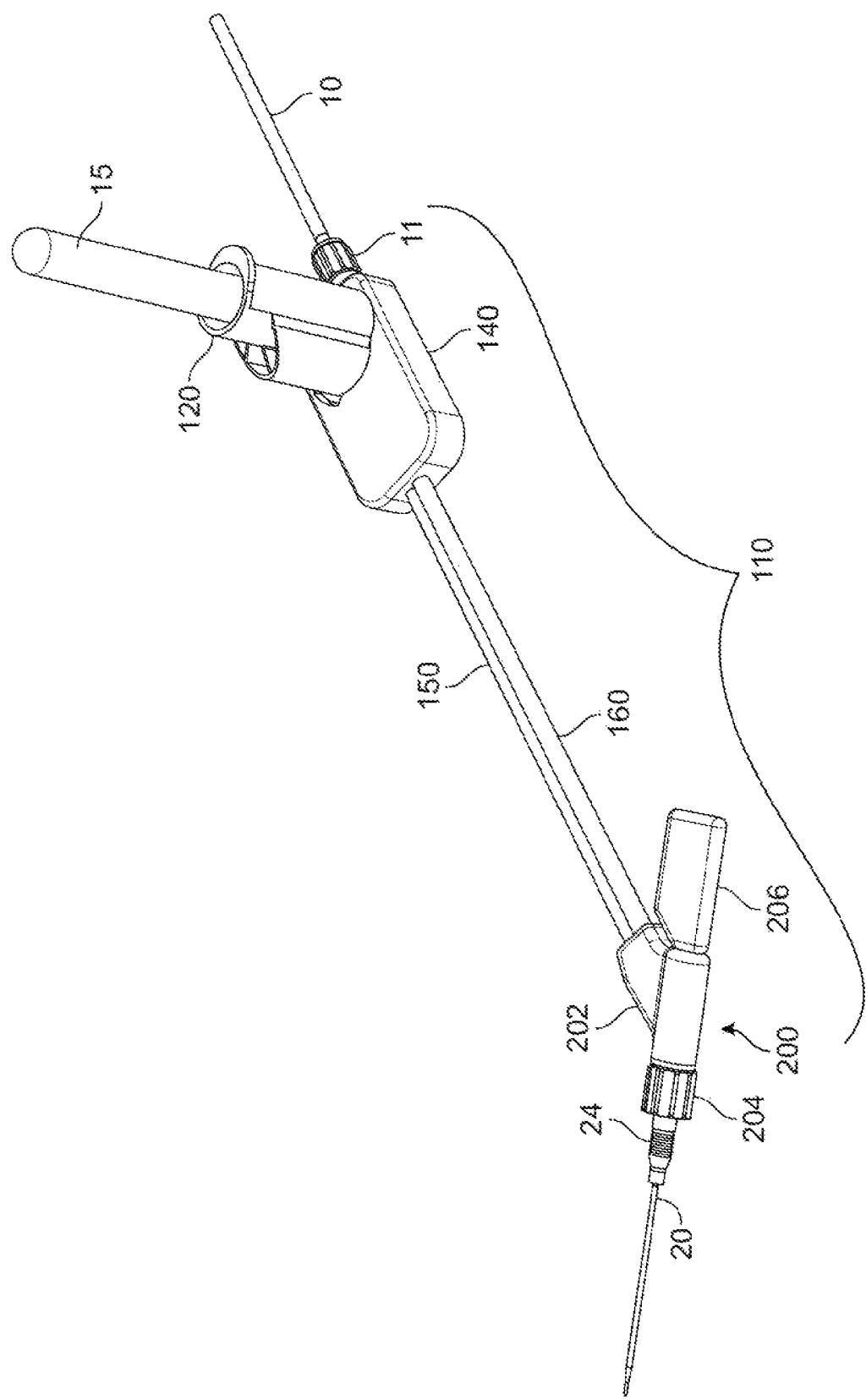
FIG. 11 is a perspective assembly view of a second illustrative embodiment of an infusion and blood collection device of the invention herein, illustratively shown installed between an IV infusion line and a Peripheral Venous Catheter.
Figure 13:
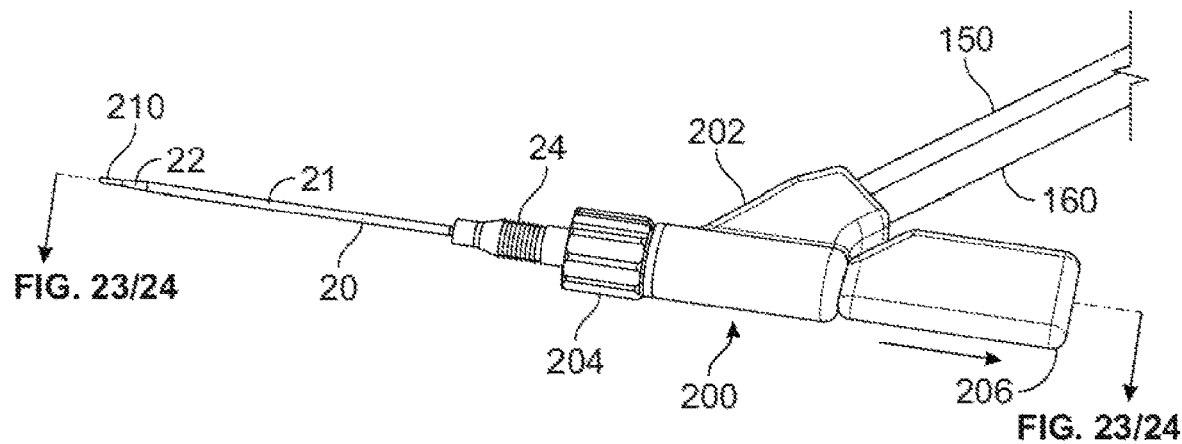
FIG. 13 is a perspective view of the catheter head assembly of the second embodiment of the device of FIG. 11.

Referring to FIGS. 11 and 13 in the Drawings section, these figures show a perspective view of a second illustrative embodiment of an illustrative infusion and blood collection device 110 of the invention herein, illustratively installed between a standard IV infusion line 10 and a standard catheter 20, for example, a peripheral venous catheter. An example of such a standard catheter 20 is the shielded IV catheter product number 381703, also known as the BD Angiocath Autoguard 20 gauge, available from Becton, Dickson and Company (BD), of Sandy, Utah.

The illustrative embodiment of the infusion and blood collection device 110 of the present invention comprises the following main components, depicted in FIG. 11. A collection tube holder 120 for receiving a standard vacuum collection tube 15, a transfer valve and collection body 140, an intravenous infusion inlet 143 (FIG. 12) for fluid coupling with the IV infusion line 10, a blood collection lumen 150, an intravenous infusion lumen 160, and a catheter head assembly 200 for fluid coupling with the catheter 20. The blood collection lumen 150 and intravenous infusion lumen 160 couple the catheter head assembly 200 to the transfer valve and collection body 140.

Figure 12:
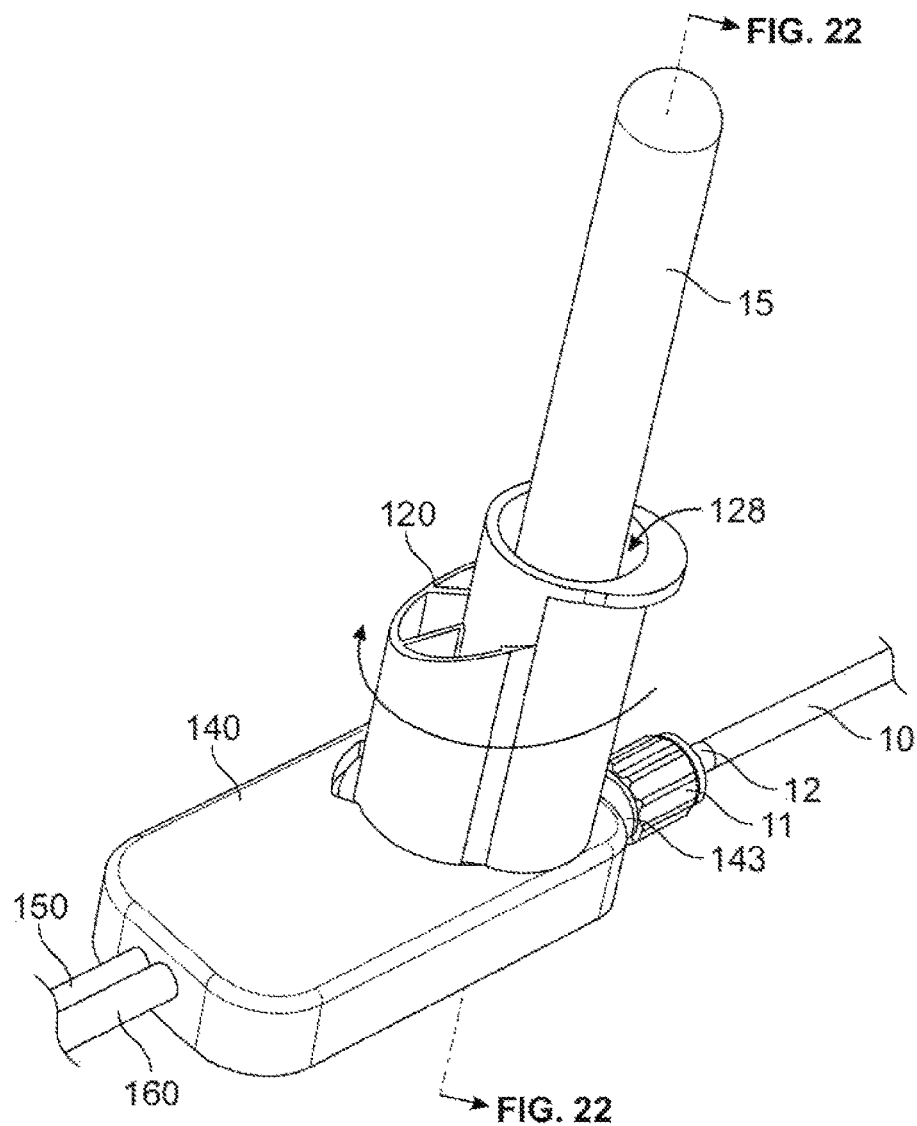
FIG. 12 is a perspective view of the transfer and collection assembly of the second embodiment of the device of FIG. 11.

FIG. 12 illustrates the tube holder 120, vacuum collection tube 15, and transfer valve and collection body 140, assembled together, and FIG. 13 illustrates the catheter head assembly 200, including a catheter head body 202. The distal end of the catheter head body 202 includes a connector 204 for coupling the connector 83 (FIG. 23) at the proximate end 24 of a standard venous catheter 20. Additionally, catheter head assembly 200 comprises an attached, microlumen 210 that passes coaxially through the interior of catheter 20.

Figure 23:
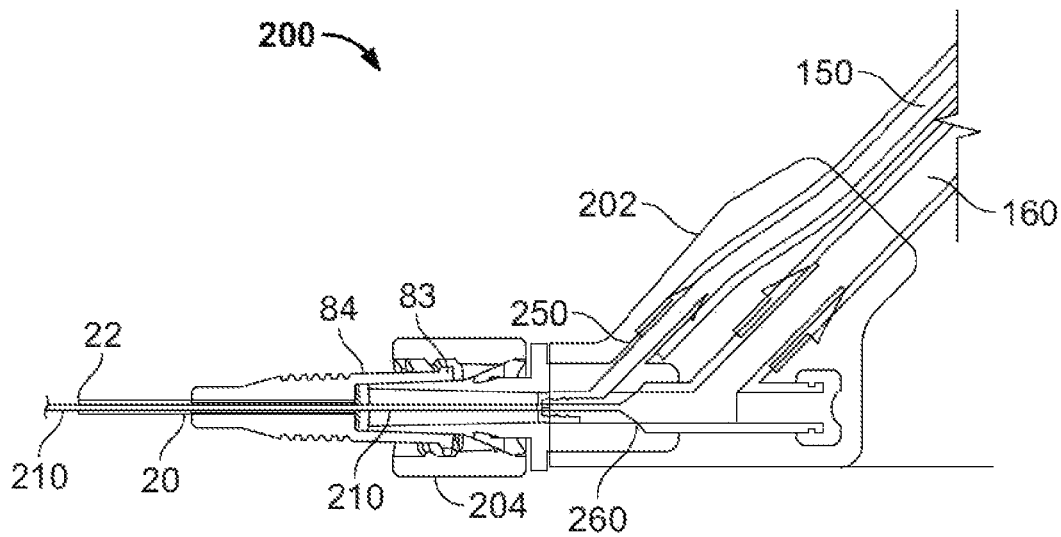
FIG. 23 is a cross-sectional view of the catheter Head assembly of FIG. 13 taken along sectional cutting plane line 23-23.

The catheter head body 202 provides fluid coupling between the microlumen 210 and blood collection lumen 150 and between the catheter 20 and the intravenous infusion lumen 160. FIG. 23 is a cross-sectional side view of catheter head assembly 200 and illustrates the internal passageways 250 and 260 defined by body 202. Blood collection passageway 250 retains and is in fluid communication with the blood collection lumen 150 and with the catheter 20, or more specifically, the open space between the interior of the catheter 20 and exterior of the microlumen 210. Infusion passageway 260 retains and is in fluid communication with intravenous infusion lumen 160 and the microlumen 210.

A blood collection channel is defined in part by the passage defined by the space between the catheter 20 and microlumen 210, the passageway 250, and the lumen 150. An infusion channel is defined in part by the microlumen 210, the passageway 260, and the lumen 160. As will be discussed in greater detail below, the blood collection channel 152 is used to provide infusion flow to the patient when the device 110 is in an infusion/non-collection mode, and, as discussed below, for reverse flow of blood 18 from the patient to the collection tube 15, when the device 110 is in an infusion/collection mode. On the other hand, the infusion channel 162 is used in either mode only for one-way infusion flow to the patient, as is discussed below.

Figure 24:
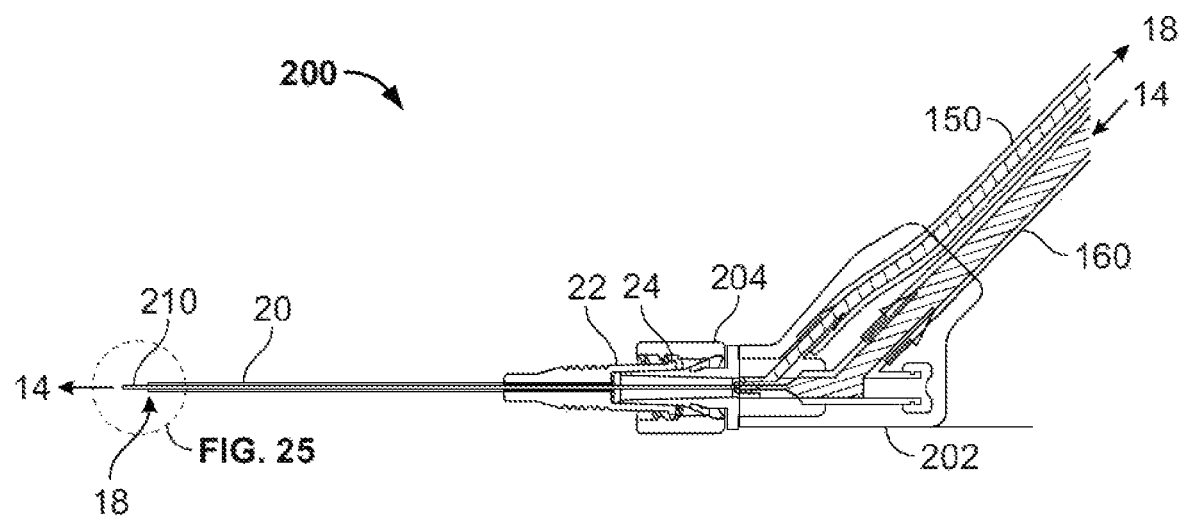
FIG. 24 is a cross-sectional view of the catheter Head assembly FIG. 13 taken along sectional cutting plane line 24-24 and showing IV flow in the IV channel and blood flow in the blood collection channel inside the assembly.
Figure 25:
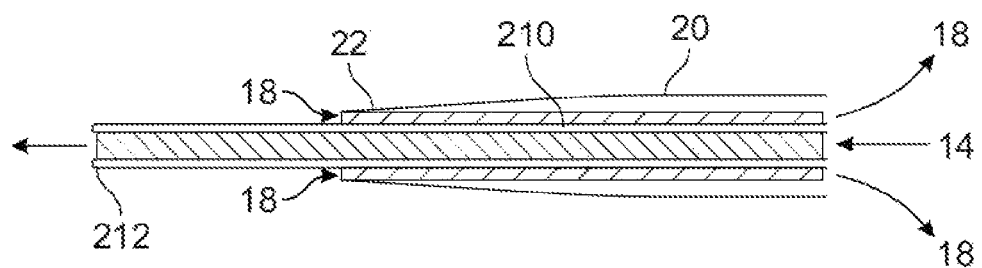
FIG. 25 is an enlarged partial cross-sectional view of the tip of the catheter and microlumen of FIG. 24 showing the microlumen tip protruding beyond the tip of the catheter.

In FIGS. 23-25, the distal end 212 of the microlumen 210 is shown protruding distally out from the distal end 22 of the catheter 20. FIG. 25 is an enlarged, partial view of the distal tip portion 22 of catheter 20, and more clearly illustrates the protruding distal portion 212 of the microlumen 210. The length of the distal portion 212 of the microlumen 210 that protrudes from the distal end 22 of the catheter 20 is illustratively around 10 mm, but it can vary depending on the type and model of catheter used and the desired blood collection flow rate. The protrusion length and blood collection flow rate are of significant importance to the invention herein, in order to prevent mixing, and thus contamination, of the drawn blood 18 with the IV fluids 14, as will become apparent from the discussion below. For example, a commonly used catheter 20 is 18 or 20 gauge which allows a flow rate of about 65-100 mL/min., though the flow rate will vary as the internal diameter is varied. A microlumen 210 providing the desired functionality when axially inserted within catheter 20 is about 25 to 26 gauge.

FIGS. 11 and 13 also illustrate the catheter head assembly 200, including a microlumen stabilizer pull handle 206 (omitted from the views illustrated in FIGS. 23 and 24). Pull handle 206 is connected to a wire or pin (not shown) that is inserted through the interior of microlumen 210, providing rigidity to the microlumen 210 and catheter 20 for insertion of the respective distal ends 212 and 22 into the patient. After successful patient insertion, the pull handle 206 is actuated proximately along its axis, thereby extracting the wire or pin (not shown) from the interior of microlumen 210, reducing rigidity. It is understood that the technique of catheter insertion can follow the standard technique for catheter insertion that is well-known in the art.

Figure 14:
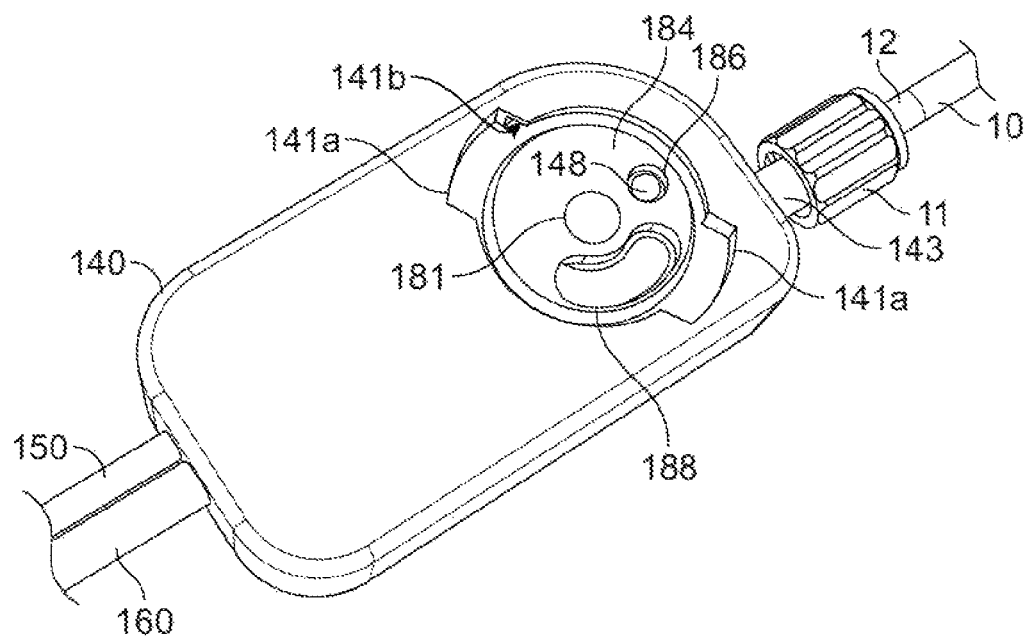
FIG. 14 is a top perspective view of the transfer valve and collection body of the second embodiment of the device of FIG. 11.
Figure 15:
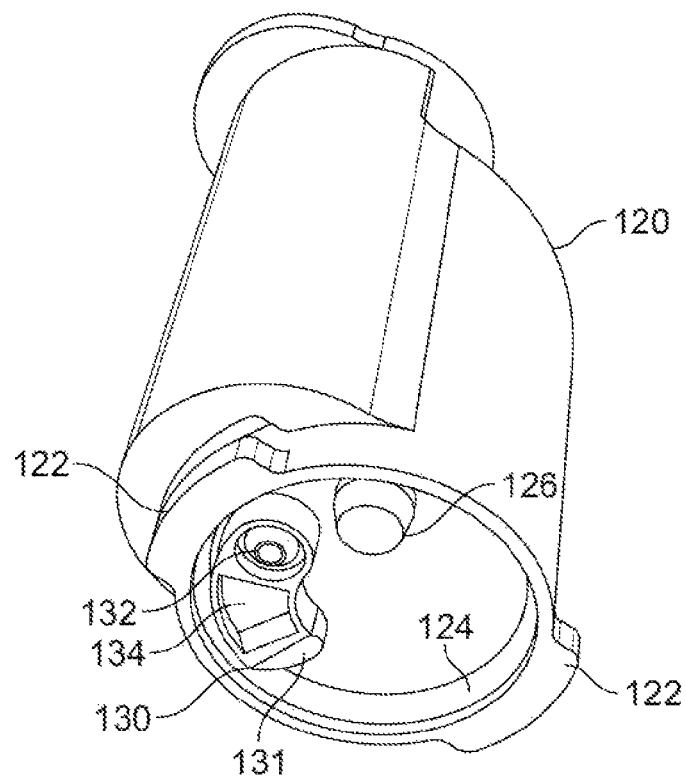
FIG. 15 is bottom perspective view of the collection tube holder of the second embodiment of the device of FIG. 11.

Reference is made again to FIG. 12, which illustrates a close-up perspective view of the assembled tube holder 120, vacuum collection tube 15, and transfer valve and collection body 140. FIGS. 14 and 15 illustrate the transfer valve and collection body 140 and the tube holder 120, respectively, disassembled from one another. A perspective view of the bottom side of the tube holder 120 is shown in FIG. 15. Transfer valve and collection body 140 encloses a transfer valve housing 142 (see FIG. 16 below), including a valve assembly 180 (partially shown in FIG. 19, and discussed in greater detail below), and a locking interface having keyed openings 141a and retention flanges 141b for locating and retaining the tube holder 120 relative to the valve assembly 180. Specifically, the retention wings 122 (FIG. 15) protruding radially from actuator receiver 124 on a bottom of the tube holder 120 are received through the keyed openings 141a, and upon the tube holder 120 being rotated relative to the transfer valve and collection body 140, the retention wings 122 rotate under the retention flanges 141b to retain the tube holder 120 firmly to the transfer valve and collection body 140.

Referring to FIGS. 14, 19, 22, 27, and 29, the valve assembly 180 includes a rotary valve 182, a valve actuator 184, an elastomeric valve layer 190, and a portion of the housing top 144. The actuator 184 is spaced apart from and rotationally fixed with the rotary valve 182 by a central shaft 181. The elastomeric valve layer 190 and portion of housing top 144 are fixed relative to the housing 140, and therefore do not rotate with the rotary valve 182, actuator 184, and shaft 181. Actuator 184 (FIGS. 14 and 16) defines an opening comprising a latch boss receiver 186 that engagingly receives latch boss 148 (FIG. 17), and further defines an elongated, arcuate opening comprising a draw port interface receiver 188 that engagingly receives the draw port interface 130 (FIG. 15) of the tube holder 120.

The tube holder 120 also comprises a latch actuation key 126 and an elongated, arcuate draw port interface 130, both located within the actuator receiver 124. The draw port interface 130 is positioned and sized to fit precisely into draw port interface receiver 188 upon mounting the tube holder 120 to the transfer valve and collection body 140. Likewise, latch actuation key 126 is positioned and sized to fit precisely into the latch boss receiver 186 upon mounting the tube holder 120 to the transfer valve and collection body 140. Draw port interface 130 further comprises a recessed alcohol or other disinfectant swab 134 and a needleless draw nozzle 132.

Figure 16:
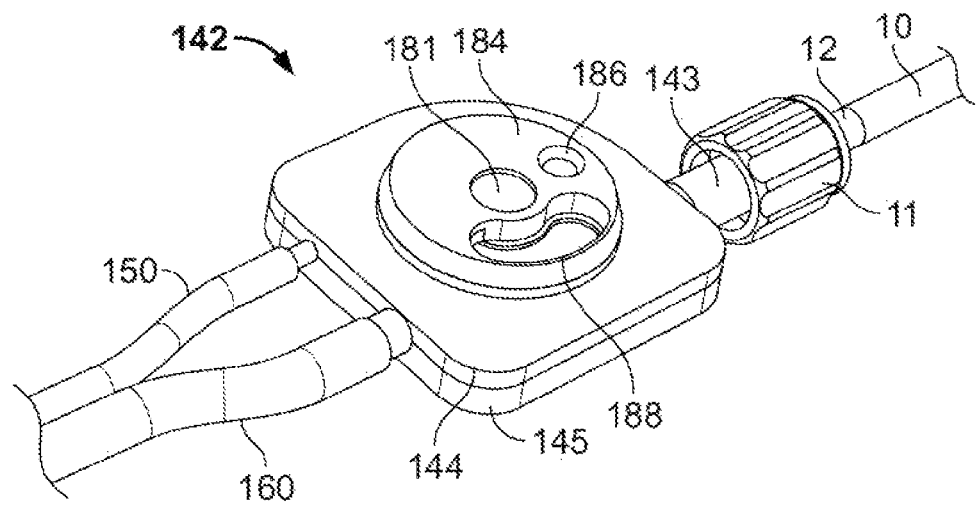
FIG. 16 is a top perspective view of the transfer valve housing of the second embodiment of the device of FIG. 11.
Figure 17:
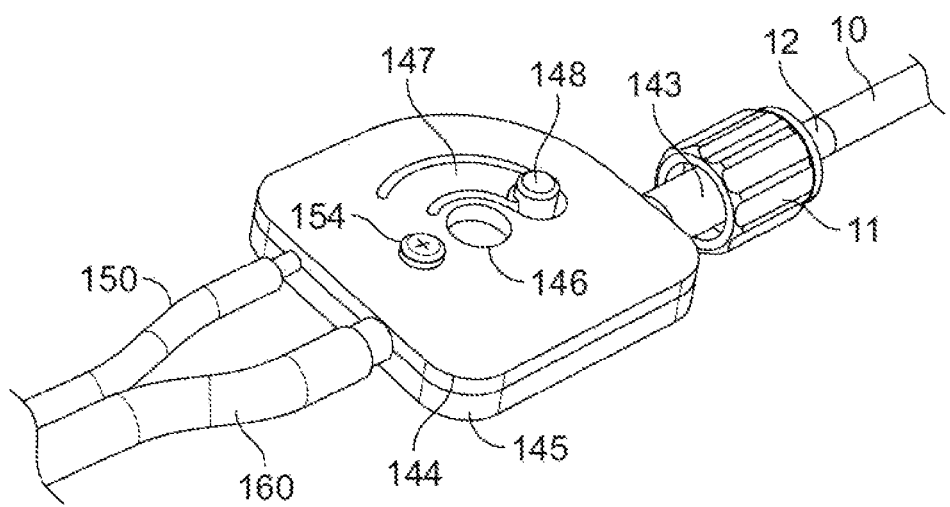
FIG. 17 is a top perspective view of the transfer valve housing of FIG. 16 with the rotary valve actuator removed.

Referring now to FIG. 16, this figure shows a top perspective view of the transfer valve housing 142 as it would appear if removed from the transfer valve and collection body 140. Transfer valve housing 142 includes a housing top 144 and a housing bottom 145. Transfer valve housing 142 also houses a valve assembly 180 comprising an valve actuator 184 and a rotary valve 182 (not shown in FIG. 16)

rigidly held together with a shaft 181, and the housing top 144 and an elastomeric valve layer 190 there between (the valve assembly 180 is discussed in greater detail in connection with FIG. 19 below). Materials from which the housing 142, tube holder 120, actuator 184, and valve 182 can be formed, include, for example, structural polymer material such as ABS, Polyurethane, Polycarbonate, PBT, PEI, PEEK, Polypropylene, PET, and the like. Materials from which the elastomeric layer 190 can be formed, include, for example, thermoplastic urethane, thermoplastic vulcanizate, PEBA, TPE, RTV Silicone, and the like.

The housing top 144 includes an opening 146 for receiving the valve assembly central shaft 181 there through and a curved latch cantilever 147 at the distal tip of which is located a latch boss 148. The latch boss 148 cooperates with the latch boss receiver 186 of the valve actuator 184 to rotationally lock the valve assembly 180 relative to the housing 142 and elastomeric valve layer 190. The housing top 144 also includes a needleless draw port 154 from which a blood collection flow 18 is provided to the tube holder 120 during a particular operating mode described further below.

Figure 19:
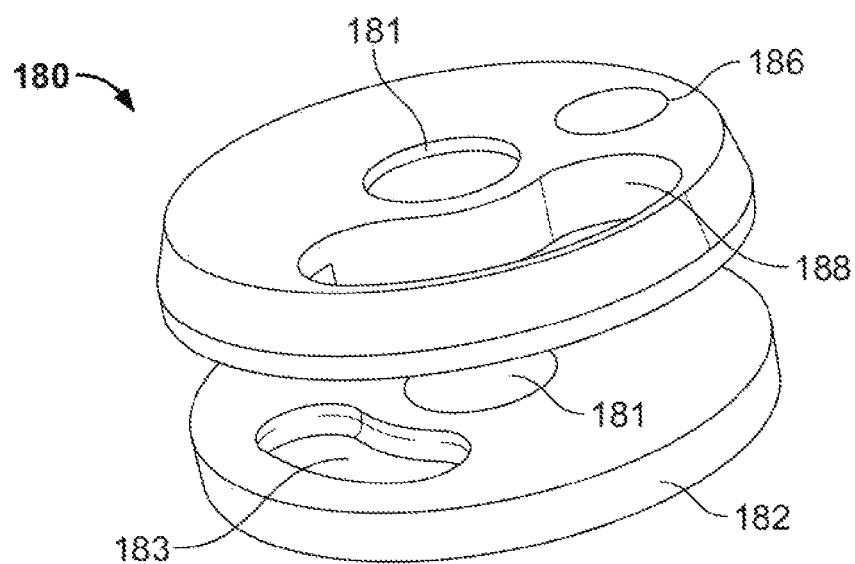
FIG. 19 is a perspective view of the rotary valve and actuator of the transfer valve housing of FIG. 17.
Figure 22:
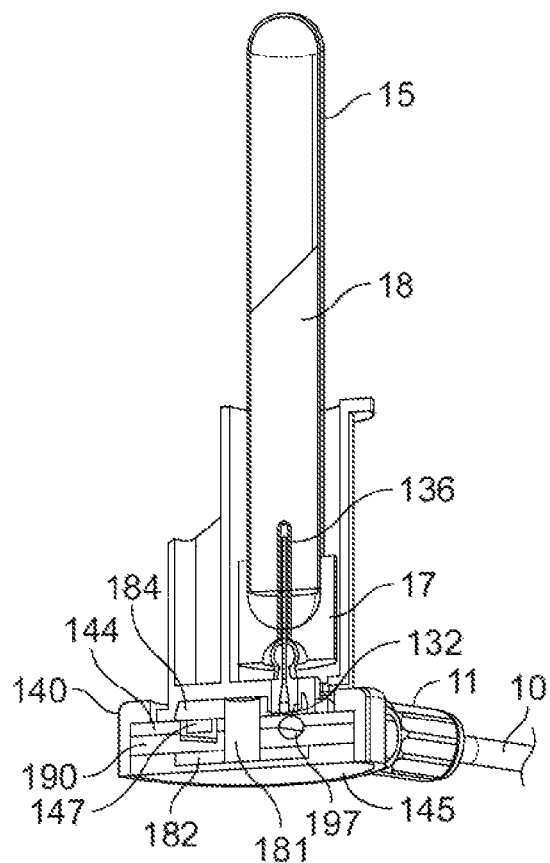
FIG. 22 is a cross-sectional view of the transfer valve housing and tube holder of FIG. 12 taken along sectional cutting plane line 22-22.
Figure 27:
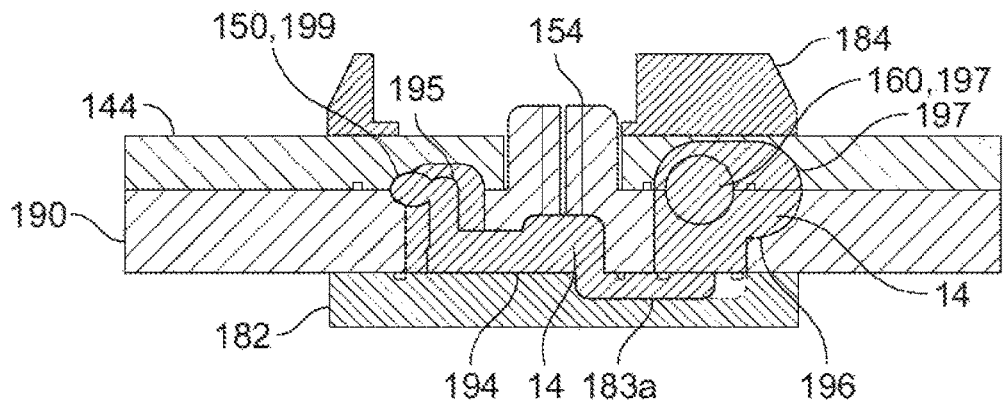
FIG. 27 is semi-transparent cross-sectional view of the transfer valve housing of FIG. 26 taken along sectional cutting plane line 27-27 and showing the infusion/non-collection mode.
Figure 29:
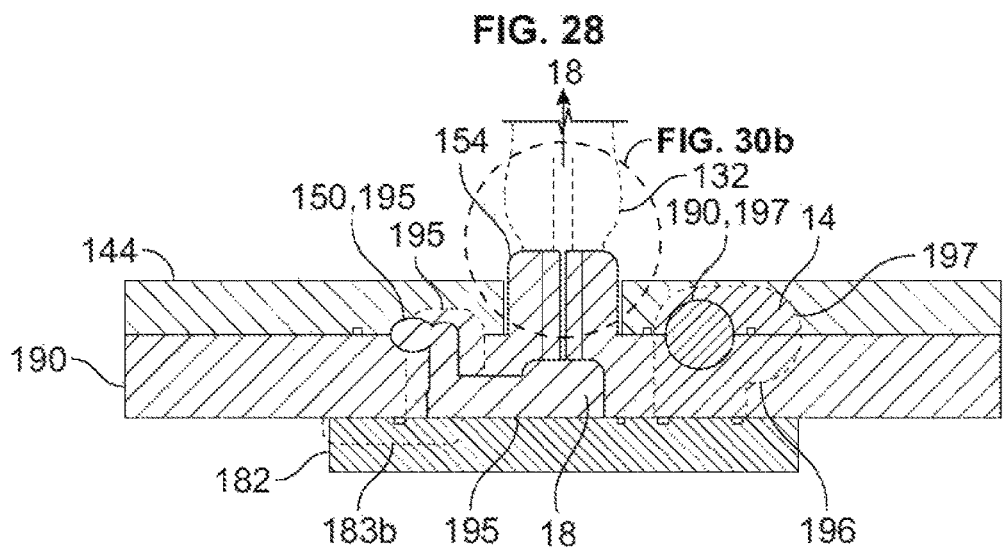
FIG. 29 is semi-transparent cross-sectional view of the transfer valve housing of FIG. 28 taken along sectional cutting plane line 29-29 and showing the infusion/collection mode.

Referring now to FIG. 19, this figure shows the valve assembly 180 with its valve actuator 184, rotary valve 182, and shaft 181. As discussed above, valve actuator 184 defines the latch boss receiver 186 and the draw port interface receiver 188 for the draw port. Rotary valve 182 is shown in FIG. 19 to define transfer channel 183. The valve 182 and actuator 184 are spaced apart to fit precisely on opposite sides of the housing top 144 and elastomeric valve layer 190, as is best illustrated in FIGS. 22, 27, and 29, with the housing top 144 located between the actuator 184 and the elastomeric valve layer 190, the elastomeric valve layer 190 located between the housing top 144 and the rotary valve 182, and the rotary valve 182 located between the elastomeric valve layer 190 and the housing bottom 145. The precise sizing and positioning of the various features on the valve 182, elastomeric valve layer 190, actuator 184, and the features of the housing top 144 is of substantive importance, as discussed above and below.

Figure 18:
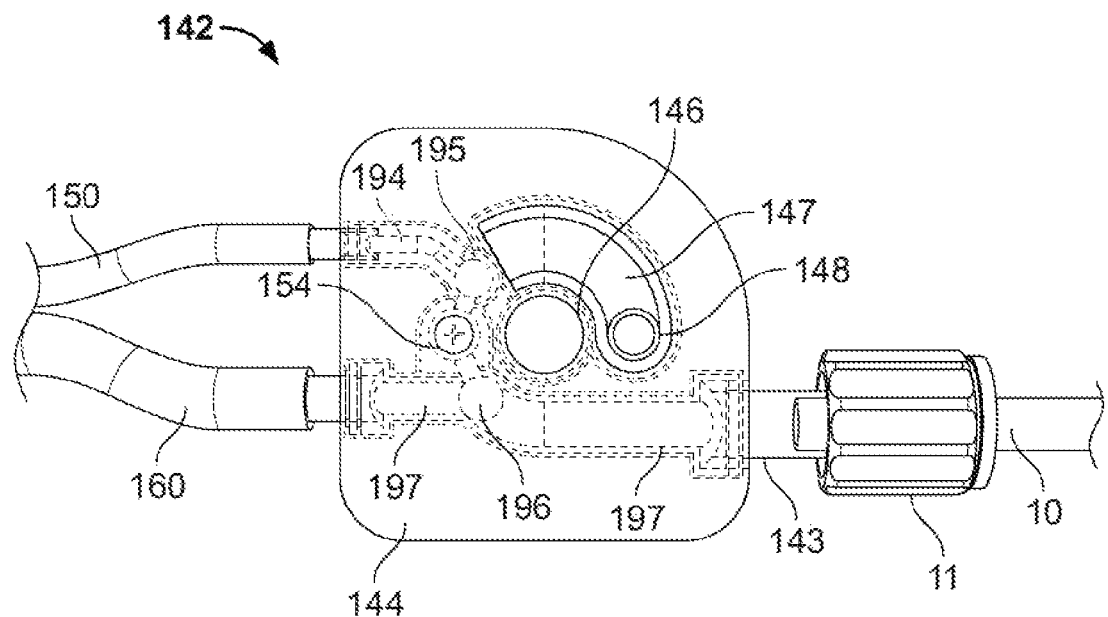
FIG. 18 is a semi-transparent top view of the transfer valve housing of FIG. 17 showing the infusion and collection channels in the device.

FIG. 18 and various subsequent FIGS. shows a semi-transparent view of the transfer valve housing 142, including fluid passageways defined by portions of the housing top 144, elastomeric valve layer 190, rotary valve 182. These fluid passageways are selectively in fluid communication with the incoming IV infusion line 10 via inlet 143, the infusion lumen 160, the blood collection lumen 150, and the needless draw port 154. Specifically, and referring to FIGS. 21 and 28, the blood collection channel 152, described in part above, is further defined by a blood collection passageway 194, including blood collection transfer orifice 195, and draw port 154. The blood collection lumen 150, passageway 194, transfer orifice 195, and draw port 154 are always in fluid communication for both operating modes, namely the infusion/non-collection mode illustrated in FIGS. 26-27, and the infusion/collection mode illustrated in FIG. 28-29. Additionally, the infusion channel 162, described in part above, is further defined by the infusion passageway 197, including the infusion transfer orifice 196. The infusion lumen 160, passageway 197, transfer orifice 196, inlet 143, and IV infusion line 10 are likewise always in fluid communication for both operating modes.

In contrast, selective fluid communication is provided depending on the rotational location of the valve assembly 180 and tube holder 120 relative to the transfer valve housing 142. Before mounting of the tube holder 120 to the transfer valve and collection body 140, the rotary valve 182 and valve actuator 184 are in their counterclockwise most position, shown in FIGS. 16 and 26-28. This relative position provides the infusion/non-collection mode of operation, in which the transfer channel 183 defined by the rotary valve 182 is in a rotational position 183a, shown best in FIG. 27, but also shown in FIGS. 20 and 26, which provides unrestricted fluid communication between the infusion transfer orifice 196 and the blood collection orifice 195, the function of which will be further described below.

Figure 21:
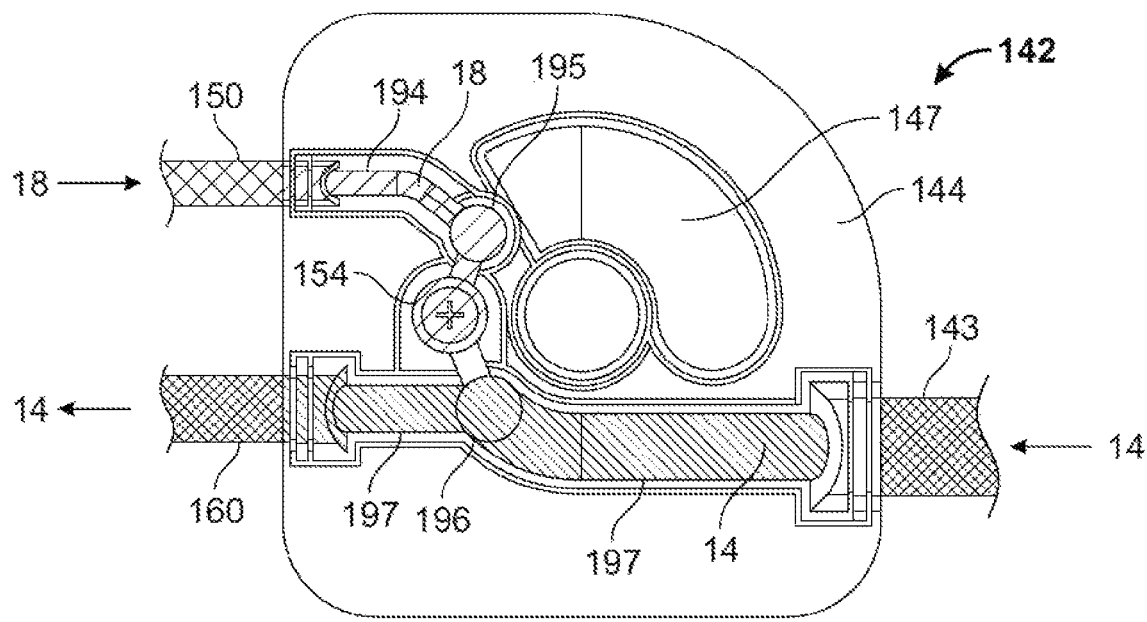
FIG. 21 is a semi-transparent top view of the transfer valve housing of FIG. 17 in the infusion/collection mode and showing IV flow in the IV channel and blood flow in the blood collection channel.
Figure 28:
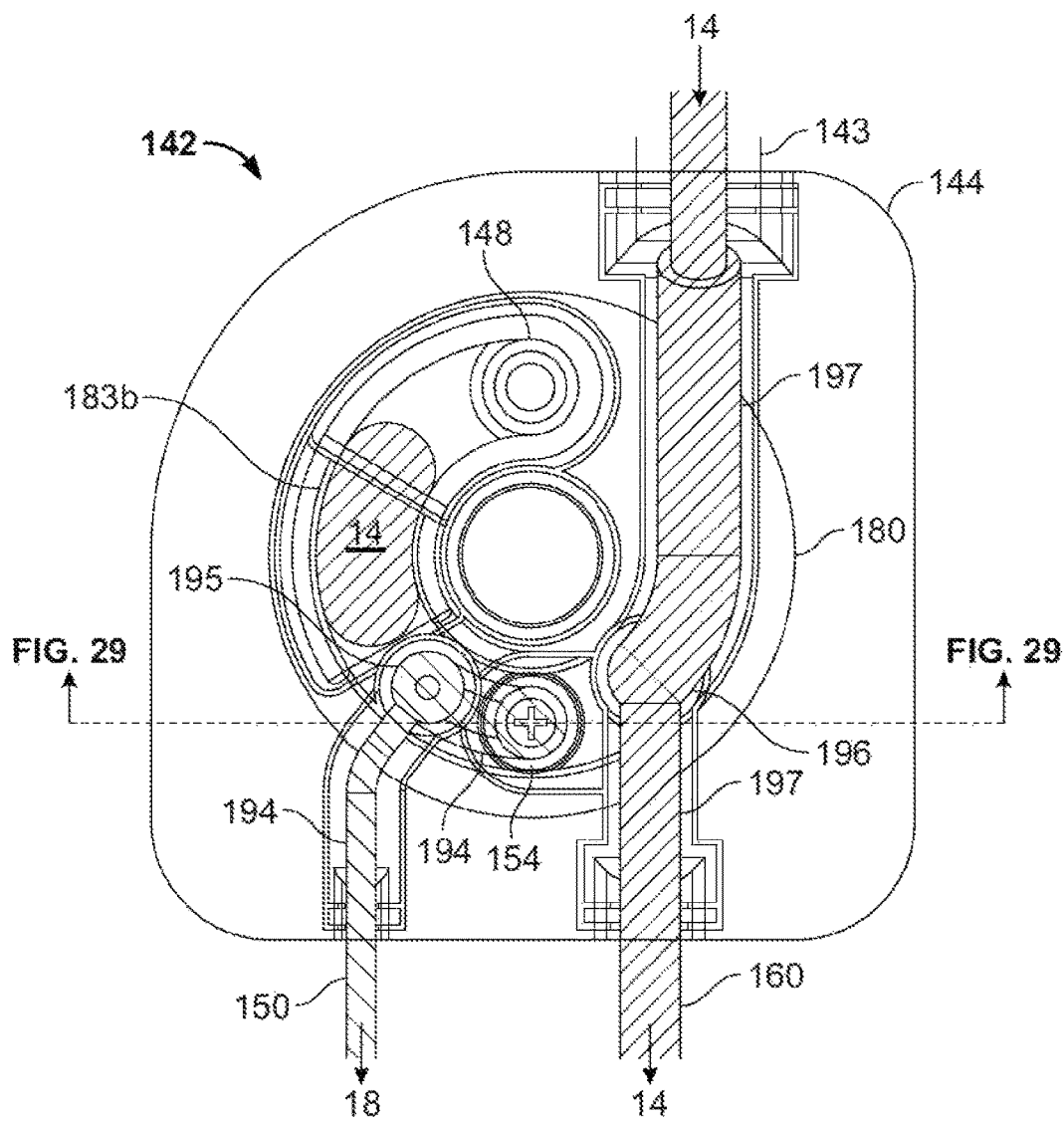
FIG. 28 is a transparent top view of the transfer valve housing of FIG. 16 in the infusion/collection mode and showing IV flow in the IV channel and blood flow in the blood collection channel.

Upon mounting tube holder 120 to the transfer valve and collection body 140, including full available clockwise rotation of the tube holder 120, valve actuator 184, and rotary valve 182, the infusion/collection mode of operation is provided, in which the transfer channel 183 is located in the rotation position 183b, shown in FIGS. 21 and 28-29, which provides fluid isolation between the infusion transfer orifice 196 and the blood collection orifice 195, and thus, fluid isolation through all of the blood collection channel 152 and the infusion channel 162. Additionally, in the infusion/collection mode of operation, the needleless draw nozzle 132 is in fluid communication with the needleless draw port 154, and thus the blood collection channel 152 is further defined in this operating mode by the needleless draw nozzle 132 and tube penetration needle 136.

Selection between the infusion/non-collection mode and the infusion/collection mode is provided by the mounting and clockwise rotation, and the counter-clockwise rotation and unmounting of the tube holder 120 with the transfer valve and collection body 140, including the associated function of various interoperative structures resulting from the mounting and rotation.

Upon the tube holder 120 being mounted to the transfer valve and collection body 140, the valve actuator 184 is received into the actuator receiver 124 (FIG. 15), and the latch actuation key 126 extends downward into the latch boss receiver 186, from the side opposite that from which the boss 148 of cantilever 147 upwardly extends into the latch boss receiver 186, pressing the boss 148 downward and clear of the latch boss receiver 186. Furthermore, when the tube holder 120 is mounted to the transfer valve and collection body 140 the draw port interface 130 fits precisely into draw port interface receiver 188. To mount the tube holder 120 to the transfer valve and collection body 140, the two are brought together, fitting the matching and retention features as described above, and the holder 120 is rotated so as to engage the tube holder retention wings 122 under the retention flanges 141b.

Figure 20:
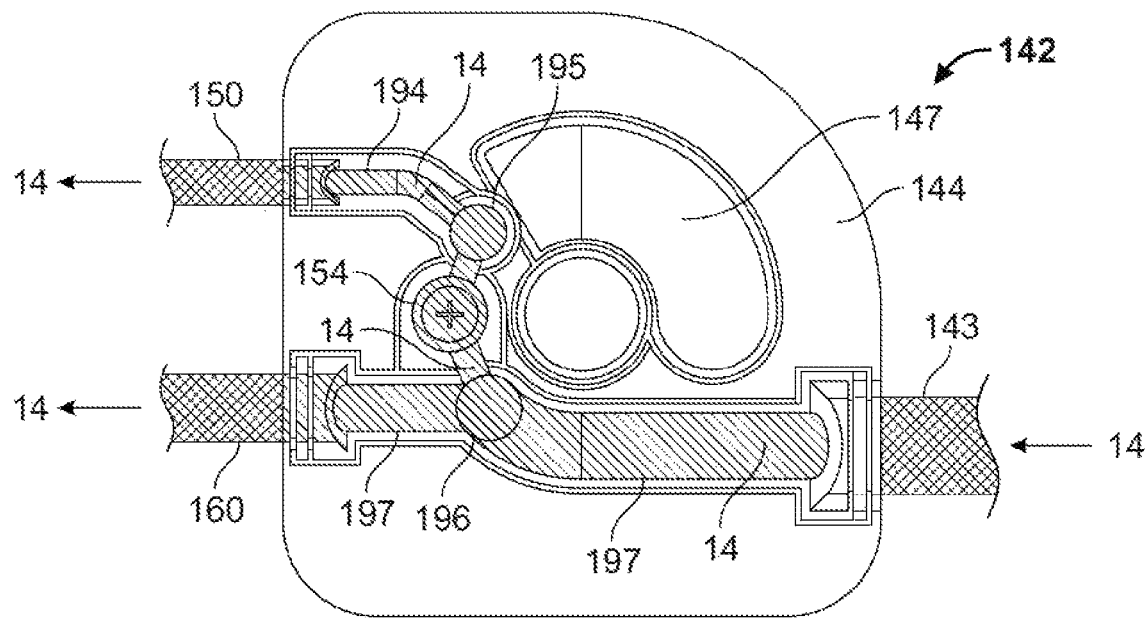
FIG. 20 is a semi-transparent top view of the transfer valve housing of FIG. 17 in the infusion/non-collection mode and showing IV flow in all channels.

FIG. 22 shows a cross-sectional cut-off view of the tube holder 120 and the transfer valve and collection body 140 assembled together. FIG. 22 also shows the collection tube penetration needle 136 that is coupled to the tube holder 120, projecting upwardly into the center of tube receptacle 128, and in fluid communication with the needleless draw nozzle 132. FIG. 22 also illustrates the collection tube penetration needle 136 penetrating the cover 17 portion of the collection tube 15 that is inserted axially into the tube receptacle 128 so that a blood sample 18 can be collected therein. The figure shows the assembly in the normal, non-blood-collection mode, wherein the needleless draw nozzle 132 does not overlap the needleless draw port 154. In this infusion/non-collection mode, the valve assembly 180 functions to provide the IV fluid 14 flowing into inlet 143 from IV infusion line 10 into both channels 152 and 162, and thus both lumens 150 and 160, as shown in FIG. 20, and continues on in both channels through both the catheter 20 and microlumen 210 and into the patient's vein.

In the following illustrative use of the illustrative device 110, the installation of the infusion and blood collection device 110 during intravenous therapy of a patient is described. Prior to installation of the device 110, following standard techniques well-known in the art, the peripheral venous catheter 20 is typically inserted into a vein of the patient and the IV therapy tube 10 is connected via a Luer-type or other connection 11. To install the infusion and blood collection device 110 in preparation for drawing clean blood samples from the patient via the catheter 20, the IV therapy fluid flow 14 through IV infusion line 10 is stopped, and the peripheral venous catheter 20 is disconnected from the IV infusion line 10. The transfer valve and collection body 140 of the device is connected to the IV infusion line 10 by connecting the connector 11 to the inlet port 143.

Figure 26:
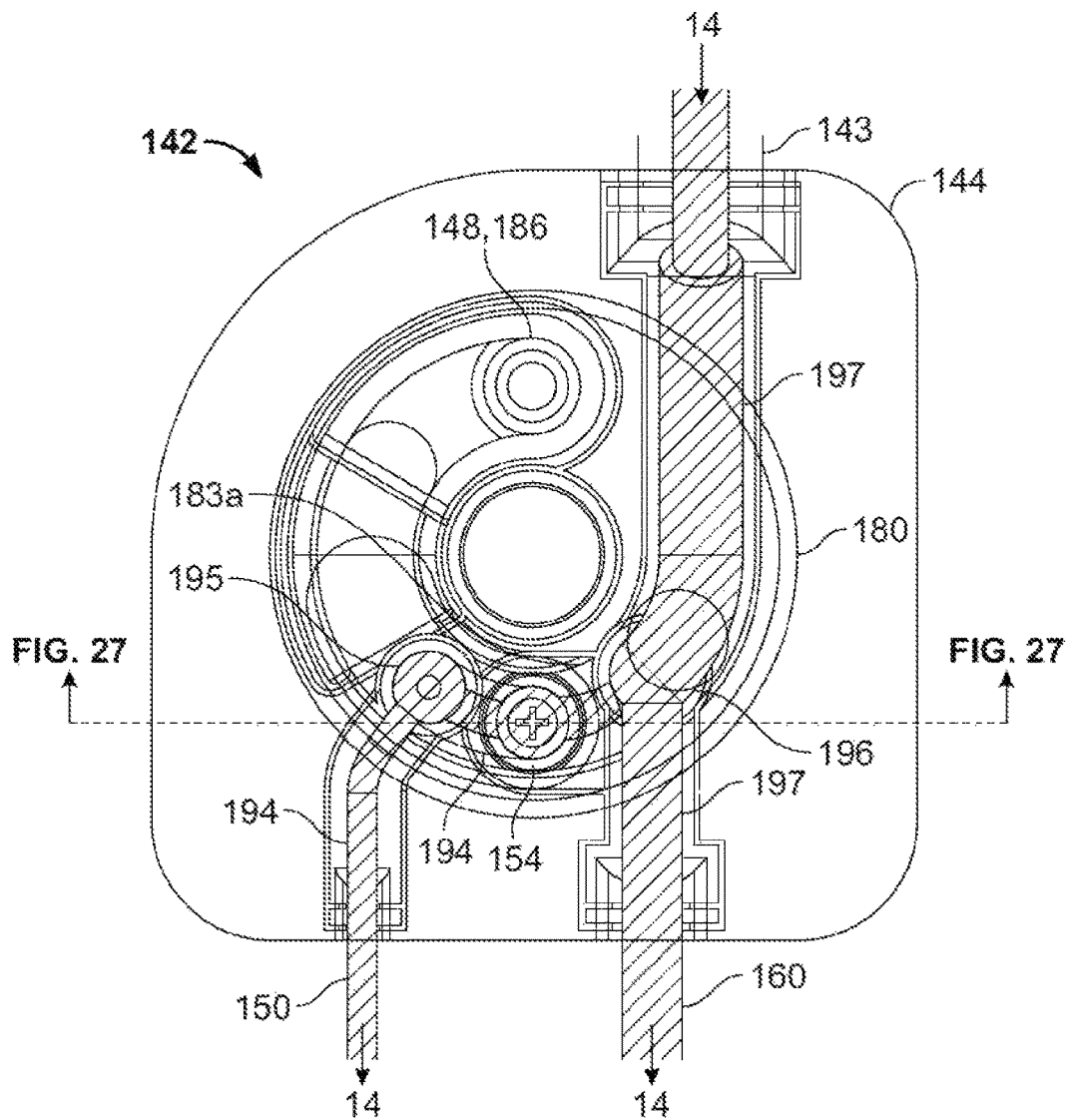
FIG. 26 is a transparent top view of the transfer valve housing of FIG. 16 in the infusion/non-collection mode and showing IV flow in all channels.

Referring to FIGS. 26-27, illustrating use of the device 110 in the infusion/non-collection mode of operation, the fluid flow 14 through the IV infusion line 10 is then restarted, and the IV fluid 14 (or for example, heparin) flowing into inlet port 143 fills both the blood collection channel 152 and the infusion channel 162 in the housing 142, lumens 150 and 160, passageways 250 and 260 defined by the catheter head body 202, until the IV fluid 14 flows from the catheter head assembly 200, thus pushing all air from the channels 152 and 162.

The catheter head assembly 200 can then be attached to the catheter 20 (which, for example, has remained in the patient) by inserting the microlumen 210 all the way through the catheter 20 and tightening the Luer-type or other connector 204 onto the male connector 83, as shown in FIG. 23. The microlumen stabilizer pull handle 206 is then pulled, retracting the wire or pin from the interior of the microlumen 210, and with the IV therapy resumed, thus allowing the IV therapy fluid 14 to infuse into the patient from both the catheter 20 and the microlumen 210 (not precisely illustrated).

The infusion/non-collection transfer channel position 183a functions to provide IV fluid flow 14 from the IV infusion line 10 through both the blood collection line/channel 150/152 and the IV infusion line/channel 160/162. Referring to FIGS. 20 and 26, the IV fluid 14 flows from the IV infusion line 10 through to the infusion conduit 197, where it is free to flow into infusion orifice 196 and flow out through the two pathways: the infusion line 160 and also through the transfer channel 183, through the blood collection orifice 195, into blood collection conduit 194 and out the blood collection line 150. Before the tube holder 120 is coupled to transfer valve and infusion body 140 the transfer channel 183 on the valve assembly 180 is in the infusion/non-collection position 183a and the blood collection port 154 is closed off from fluid 14 escaping the port.

Figures 30A, 30B:
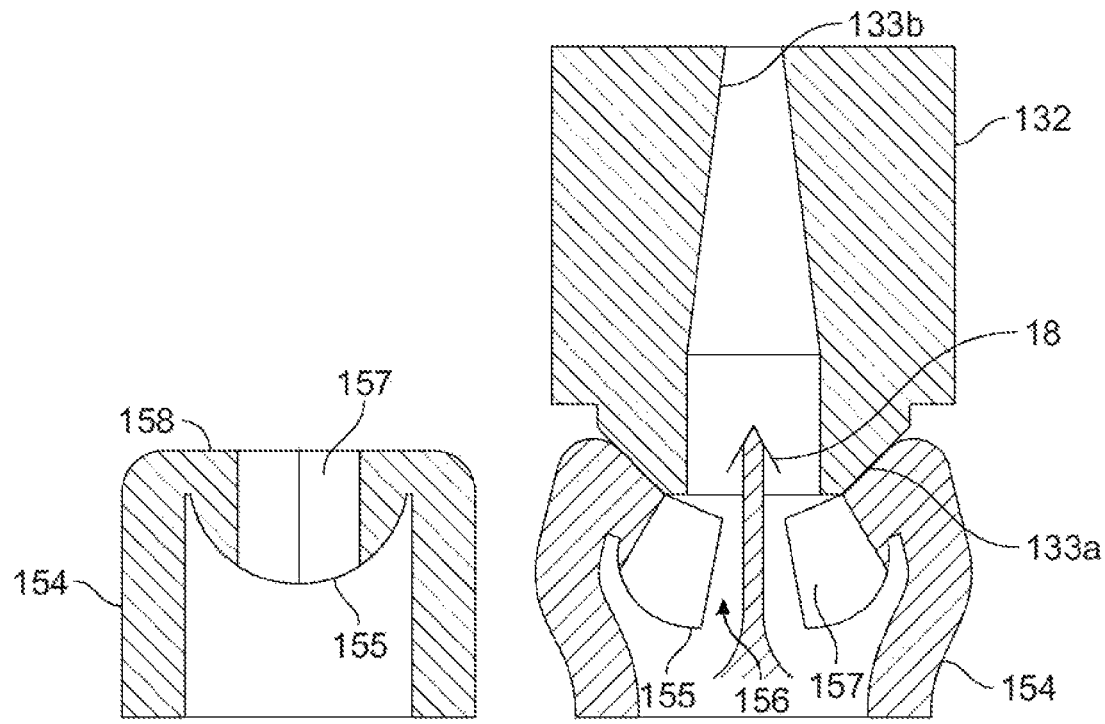
FIG. 30A is a cross-sectional view of the needleless draw port of the device of FIG. 11, taken along sectional cutting plane line 30A-30A shown in FIG. 31A, and with the device in the infusion/non-collection mode.
FIG. 30B is a cross-sectional view of the needleless draw port cooperating with the needleless draw nozzle of the device of FIG. 11, taken along sectional cutting plane line 30A-30A shown in FIG. 31A, and with the device in the infusion/collection mode.

More specifically, and referring to FIGS. 30A and 30B, the blood collection port 154 can be sealed by the design of an elastomeric central portion 155 having slits 157 and that is bulbous downward toward the source of internal pressure of the fluid 14, and wherein the internal pressure of the fluid 14 cooperates with the geometry of the central portion 155 to more tightly seal the port 154, preventing an opening 156 (FIGS. 30B and 31B) from forming between the slits 157. Alternatively, or additionally, the bottom surface of valve actuator 184 against which the top surface 158 of the central portion 155 rests when the device 110 is in the infusion/non-collection mode can act to seal or to further seal the port 154, preventing an opening 156 (FIGS. 30B and 31B) from forming between the slits 157.

In the following illustrative use of the illustrative device 110, the use of the infusion and blood collection device 110 to draw blood 18 from the patient and into a collection tube 15 without interrupting the IV therapy of the patient is described. The device 110 is installed between IV therapy infusion line 10 and patient catheter 20 and flushed off all air as described above. A tube holder 120, disassembled from the transfer valve and collection body 140, is held in one hand, and a heat sealed tab (not shown) sealing over the blood draw port interface 130 is pulled away from the tube holder 120, exposing the interface 130, including the alcohol swab 134 and the previously sterilized draw nozzle 132.

Next, the retention wings 122 of the tube holder 120 are aligned to the keyed openings 141a of the transfer valve and collection body 140. This also aligns the draw port interface 130 with the interface receiver 188, and also aligns the latch boss receiver 186 with the latch actuation key 126. The tube holder 120 is pressed firmly into position, so that the valve actuator 184 is received into the actuator receiver 124, which presses the latch actuation key 126 into the latch boss receiver 186, deflecting the latch boss 148 (including cantilever 147) downward so that it is flush with the top surface of the housing top 144, and thus axially out from the latch boss receiver 186 so that the valve actuator 184 (including the rotary valve 182 and elastomeric valve layer 190) may rotate. In this position the draw port interface 130 is also seated within the interface receiver 188 of the valve actuator 184, thus rotating the valve actuator 184 and rotary valve 182 as the tube holder 120 is rotated clockwise relative to the housing 140.

With the latch boss 148 disengaged from the latch boss receiver 186, the tube holder 120 can be rotated clockwise relative to the transfer valve and collection body 140, rotating the retention wings 122 under the retention flanges 141b until the wings 122 reach a rotational stop (not shown), retaining the tube holder 120 in place on the transfer valve and collection body 140.

During the clockwise rotation of the tube holder 120 relative to the transfer valve and collection body 140, several critical events occur: (1) The needleless draw port 154 located on the face of the housing top 144 is drawn under the ramp 131 portion of the draw port interface 130, and across the alcohol swab 134, thus wiping and cleaning the needleless draw port 154. (2) The needleless nozzle 154 is moved into axial alignment with the needleless draw port 132, cooperating to open and seal upon the draw port 132, thus allowing collected blood 18 to flow therebetween. (3) The transfer channel 183 on the rotary valve 182 of the valve assembly 180 is rotated from the infusion/non-collection mode rotational position 183a shown in FIGS. 26-27 (connecting the blood collection channel 152 and the IV infusion channel 162), and to the infusion/collection mode rotational position 183b shown in FIGS. 28-29, isolating the blood collection channel 152 from the IV infusion channel 162.

This can be clearly seen by comparing FIGS. 20 and 21 or 26 and 28, showing the flow pattern of the IV fluid 14 through the transfer valve and collection body 140 with the transfer channel 183 connecting channels 152 and 162 in the non-collection rotational position 183a, with FIGS. 21 and 29, showing the flow pattern of the IV fluid 14 and blood 18 through the transfer valve and collection body 140 with the transfer channel 183 moved into the collection position 183b, which isolates the channels 152 and 162. As can be seen in FIGS. 21, 24, and 28-29, with the transfer channel 183 in the blood collection position 183b, IV therapy fluid 14 infusion through the infusion channel 162 and out microlumen 210 continues without being inhibited, as shown in FIG. 25.

More specifically, and referring to FIGS. 30A and 30B, the blood collection port 154 can be sealed by the design of an elastomeric central portion 155 having slits 157 and that is bulbous downward toward the source of internal pressure of the fluid 14, and wherein the internal pressure of the fluid 14 cooperates with the geometry of the central portion 155 to more tightly seal the port 154, preventing an opening 156 (FIGS. 30B and 31B) from forming between the slits 157. Alternatively, or additionally, the bottom surface of valve actuator 184 against which the top surface 158 of the central portion 155 rests when the device 110 is in the infusion/non-collection mode can act to seal or to further seal the port 154, preventing an opening 156 (FIGS. 30B and 31B) from forming between the slits 157.

The next step in this illustrative use entails placing the collection tube 15 into the tube receptacle 128 of the tube holder 120 and pressing downward into the position shown in FIG. 22, allowing the penetration needle 136 to pierce the collection tube cover 32 and the vacuum in the tube 30 to pull blood 18 via the blood collection channel 152, namely, through the collection tube penetration needle 136, the needleless nozzle 132, the needleless draw port 154 which the nozzle 132 seals, the passageway 194, the transfer orifice 195, the draw channel lumen 150, the passageway 250 defined by the catheter head body 202, and between the catheter 20 and the microlumen 210, as shown in FIGS. 24-25 and 28-29.

Figures 31A, 31B:
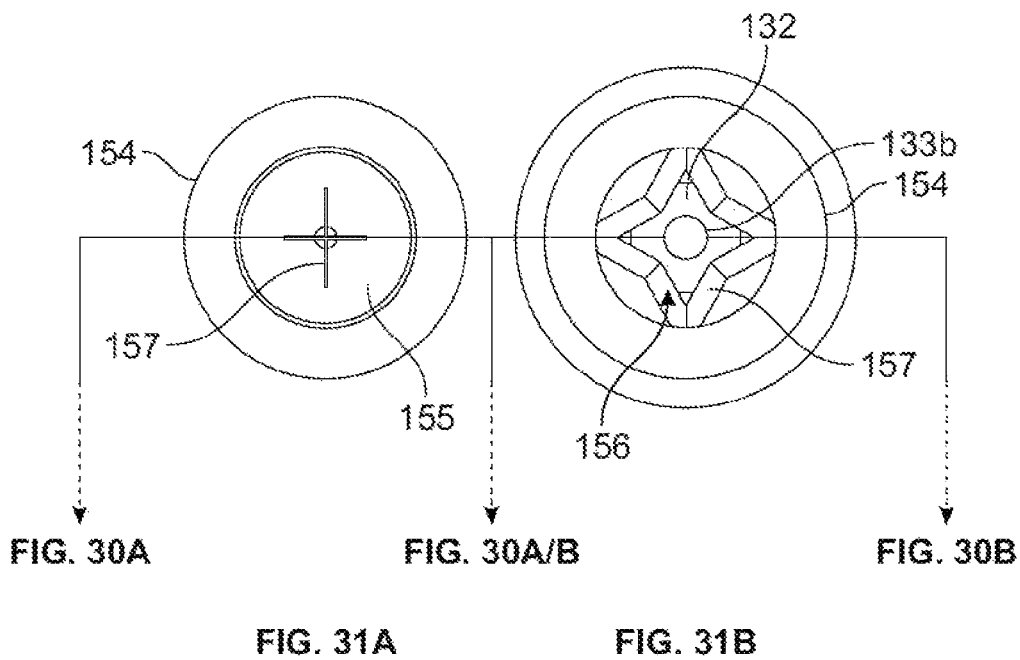
FIG. 31A is a bottom axial view of the needleless draw port of the device of FIG. 11, with the device in the infusion/non-collection mode.
FIG. 31B is a bottom axial view of the needleless draw port cooperating with the needleless draw nozzle of the device of FIG. 11, with the device in the infusion/collection mode.

Referring to FIGS. 30B and 31B, in the infusion/collection mode, the blood collection port 154 is actuated by a chamfered protrusion 133a defined at a distal end of the needleless draw nozzle 132 and sized and shaped to cooperate to open the blood collection port 154. More specifically, the top surface 158 of the elastomeric central portion 155 is pressed axially downward by the protrusion 133a, deforming the central portion 155 and allowing an opening 156 to form between the slits 157, thus allowing blood 18 to flow upwardly through the axial channel 133b in the nozzle 132 and on through the penetration needle 136 and into the collection tube 130.

Once the desired volume of blood 18 is collected into collection tube 15, the collection tube 15 is extracted from the tube receptacle 128, and the tube holder 120 is grasped in one hand and the transfer valve and collection body 140 in the other, the tube holder 120 is rotated counterclockwise relative to the body 140 and separated therefrom. This rotation and separation rotates the valve actuator 182 and the rotary valve 184 to the counterclockwise position shown in FIGS. 20 and 26-27, reengaging the latch boss 148 into the latch boss receiver 186, thereby again locking the device 110 in the infusion/non-collection mode, in which the needleless draw nozzle 132 is also rotated out of alignment with the needleless draw port 154, allowing the draw port 154 to again be sealed, preventing opening 156 from forming. In the infusion/non-collection mode, the blood collection channel 152 and infusion channel 162 are again in fluid communication via the rotational position 183a of the transfer channel 182, and the IV therapy fluid 14 is again provided to both channels 152 and 162 (FIG. 26), flushing the blood collection channel 152 of the blood 18 earlier drawn, and providing for reuse of the device 110 with a new or sterilized tube holder 120 and collection tube 15.

In regard to the restriction of blood flow 18 to reduce the blood collection flow rate to the point that the IV fluid flow is not reversed in the vein and drawn into the blood collection catheter, as with the device 100, for device 110 this restriction can be accomplished in various ways known in the art and at various locations along the blood collection channel 152, either active restriction device, passive restriction device, or a combination of active and passive restriction devices. In the above illustrative embodiment of the device 110, the restriction in flow rate is made passively via the choice of the gauge of the penetration needle 136 that penetrates the end of the collection tube, thus a needle is selected having a sufficiently narrow internal diameter to provide the required limit to blood flow rate. In the illustrative device 110 with the microlumen 210 extending 10 mm beyond the blood collection entry at catheter 20, a restriction limiting the flow rate to about 30 ml/minute provided the desired lack of contamination of the blood sample collected. This desired restriction was passively provided by using a penetration needle 136 having a gauge of about 24. In another embodiment, it is contemplated herein that the required blood collection flow restriction may be accomplished by using a tesla-type valve located anywhere along the blood collection channel 152, including located in the housing 142.

In another embodiment, it is contemplated herein that the required blood collection flow restriction may be accomplished by utilizing a check valve with a tuned reverse flow rate in lieu of a typical shut off, located anywhere along the blood collection channel 152.

In yet another embodiment, it is contemplated herein that the required blood collection flow restriction may be accomplished by utilizing a length of channel of reduced diameter to create the required restriction, located anywhere along the blood collection channel 152.

In still another embodiment, it is contemplated herein that the required blood collection flow restriction may be accomplished by having a reduction in clearance between the outside of the microlumen 210 and the inside of the catheter 20.

In still another embodiment, it is contemplated herein that the required blood collection flow restriction may be accomplished by use of a multi-lumen catheter (venous or arterial) in lieu of a typical peripheral intravenous catheter 20 and microlumen 210, but with a draw channel offset and of sufficiently small diameter and length to restrict the flow and prevent a diluted draw.

In still another embodiment, it is contemplated herein that the required blood collection flow restriction may be accomplished using an active device, which restricts the flow of the blood 18 to a collection device, located anywhere along the blood collection channel 152. Illustratively, the active device can include a pump, which draws the blood and presents the blood to the collection tube 15.

In still another embodiment, it is contemplated herein that the required blood collection flow restriction may be accomplished by having a diaphragm, needle, or other such valve actuated either by electronics or manually to create a restriction located anywhere along the blood collection channel 152.

Another embodiment of the invention herein relates to the novel feature of using a valve to segregate two or more infusion channels into a blood collection channel 152 and intravenous therapy infusion channel 162, as illustrated above. An illustrative embodiment of this feature is the use of a rotary valve as illustrated above.

In yet another embodiment, it is contemplated herein that an alternative valve type may be used. Illustratively, the valve may be a cock-stop type valve, a diaphragm type valve, an electrically actuated solenoid type valve, or a magnetic actuated valve.

In a further embodiment, described herein is a rotary blood-draw valve with locking features, as illustrated herein, to prevent access to the blood collection port by patients, for example, pediatric or agitated patients or patients suffering from various forms of dementia, or having other elevated risks relating to additional needle insertions.

In a still further embodiment, described herein is a sliding blood-draw valve with locking features, to prevent access to the blood collection port by patients, for example, pediatric or agitated patients or patients suffering from various forms of dementia, or having elevated risks relating to additional needle insertions.

In another embodiment, described herein is a collection tube holder with integrated alcohol swipe and means to clean the blood collection access port via sliding or rotating the tube holder into place prior to the draw and after the draw, as illustrated above.

It is understood that, while the illustrative embodiments of the devices 100 and 110 are directed to an angiocatheter (that is, an IV catheter), as contemplated herein, various features or combinations of features disclosed herein may be applicable to other catheters as well, such as peripherally inserted cardiac catheters, central line catheters, and the like. In the case of use with a cardiac catheter, it is understood that the required draw rate would differ because of the geometry of the vein and the blood flow rate in that region; however, the same device 110 and system can be used for controlling the blood collection rate, and a suitable protrusion length of the microlumen tip beyond the catheter tip could be easily determined and used. Additionally, it is understood that features of one of the devices 100 and 110 can be applied to the other device.

Depicted in FIGS. 32-52 is another illustrative embodiment of an infusion and blood collection device, system and/or methods 300 of the present disclosure. The system 300 generally comprises a retention component, a valve component, and an infusion component. The retention component connects to a collection tube holder 330 for receiving a standard vacuum collection tube 315. The valve component includes a valve housing 340 (including an upper portion 340a and a lower portion 340b) enclosing a movable member (for example, rotary valve 380). The valve component also includes an intravenous infusion (IV) inlet 343, an intravenous outlet 364, and a draw port 381. The infusion component connects to a catheter 320, for example, a short peripheral IV catheter (SPIC).

Materials from which the tube holder 330, valve housing 340, and rotary valve 380 can be formed include, for example, medical grade plastics and structural polymer material such as ABS, Polyurethane, Polycarbonate, PBT, PEI, PEEK, Polypropylene, PET, and the like. For example, the tube holder 330 and valve housing 340 can be formed from Polycarbonate and the rotary valve 380 can be formed from Polypropylene.

On one end of the valve housing 340, the IV inlet 343 includes a separate or integrally formed male connector (not shown) for fluid coupling with the female connector 311. On another end of the valve housing 340, a catheter head 363 connects to the valve housing 340 via a luer lock 365 for fluid coupling an IV infusion channel 358 and an IV infusion/blood collection channel 354 with the catheter 320. The luer lock 365 engages the outer surface (outer edge) of the housing 340 adjacent outlet 364.

Figure 48:
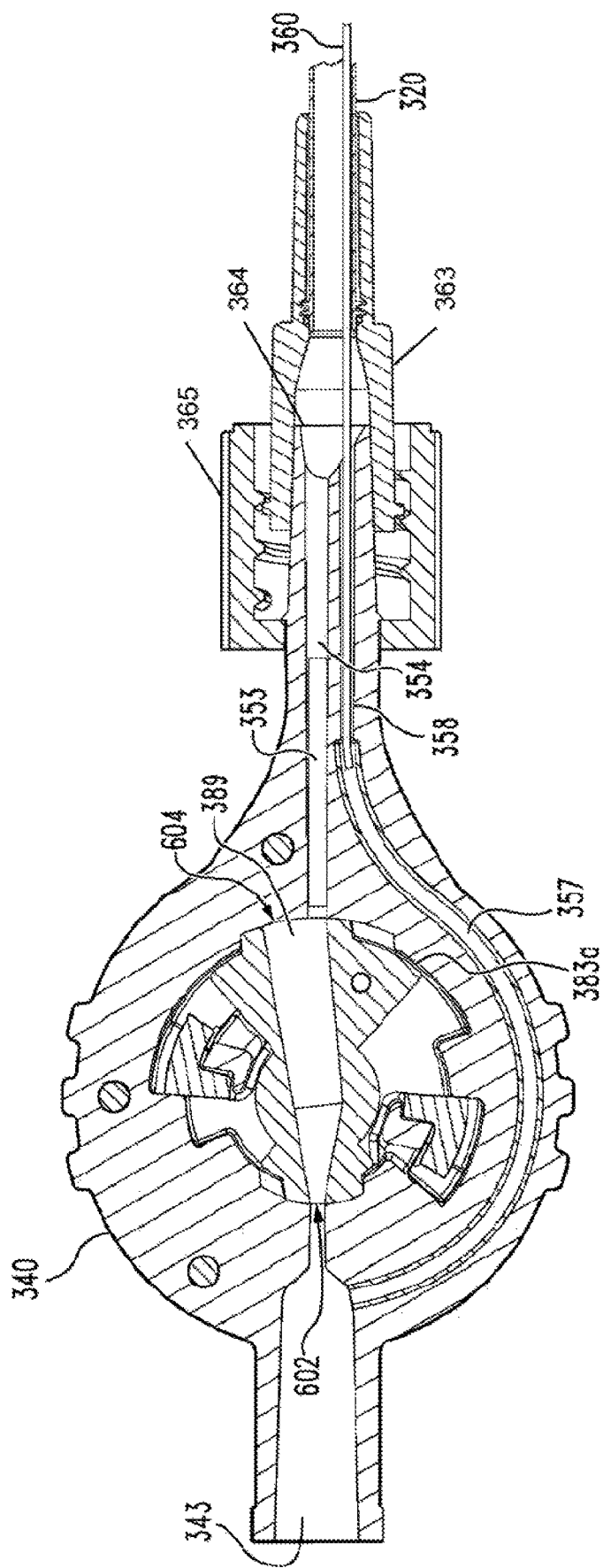
FIG. 48 is a cross-sectional view of the valve housing taken along sectional cutting plane line 48-48, shown in FIG. 35, and with the device in the infusion/non-collection mode.

The catheter head 363 may have an intravenous infusion microlumen 360 threaded therein or therethrough, the intravenous infusion microlumen 360 being fluidly coupled to an infusate tube 357 positioned within the IV infusion channel 358 in the valve housing 340. In some embodiments the infusate tube 357 is not required as sufficient coupling and sealing of components to sealingly form channel 358 is achieved without it. By coupling to the valve housing 340, the catheter head simultaneously couples to the hemotube 353 positioned within at least a portion of the IV infusion/ blood collection channel 354, wherein the outlet 364 of the channel 354 is fluidly coupled to the catheter 320 as shown in FIG. 48. In some embodiments the hemotube 353 is not required as sufficient coupling and sealing of components to sealingly form channel 354 is achieved without it. In some embodiments, the microlumen 360 may include a coated tip 361, for example, coated with PTFE for decreased friction when the microlumen 360 is inserted into catheter 320.

The rotary valve 380 includes a valve member 382 that defines a valve passage 389 having openings on the sides of the valve member 382 (see FIGS. 45-49). The valve member 382 further defines a draw port 381 (see FIG. 33) that is fluidly plugged by and retains the septum 376 and receivers 606a/b which received the tube holder 330 engagement features 336a and 336b therethrough that will be described further below.

The tube holder 330 includes a draw needle 334 and an elastomeric needle cover 335, the draw needle 334 positioned such that it pierces the needle cover 335 and the septum 376 of the infusion and blood collection system 300 as well as a vacuum collection tube 315 placed within the tube holder 330 when in use. When not in use, the tube holder can include a connectable cap 370 to prevent user injury caused by exposing the draw needle 334. The needle cover 335 illustrated in FIG. 33 is not shown in the remaining figures for illustrative efficiency.

Figure 33:
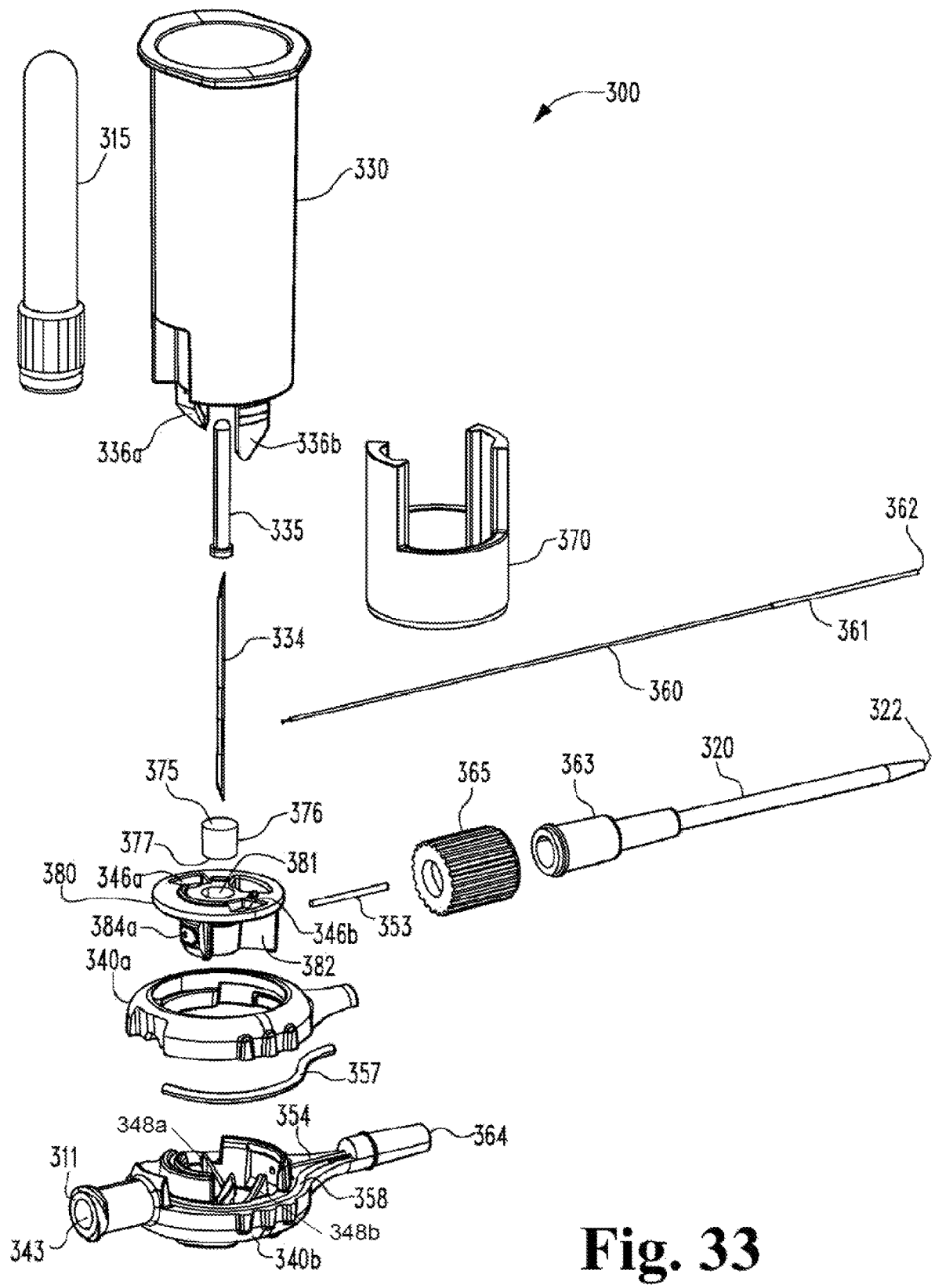
FIG. 33 is a perspective exploded view of the device of FIG. 32.

With reference to FIGS. 33 and 48, an IV infusion/blood collection channel 354 (which may be defined by portions of the hemotube 353, portions of the catheter 320 or portions of both) and an IV infusion channel 358 (which may be defined by portions of the infusate tube 357, portions of the microlumen 360 or portions of both) extend between the IV inlet 343 and the outlet 362 of the valve housing 340. Upon coupling of the catheter head 363 with the outlet 364 using the luer lock 365, the microlumen 360 is inserted coaxially within the interior of the catheter 320. For reasons more fully described below, the relative lengths of the catheter 320 and the microlumen 360 are such that a distal end 362 of the microlumen 360 protrudes from and extends distally beyond the distal end 322 of the catheter 320, thus extending axially farther along and within the patient's vein.

The microlumen 360 is in fluid communication with the infusion channel 358. The radial space between the outside surface of the microlumen 360 and the interior surface of the catheter 320 is in fluid communication with the blood collection channel 354 via outlet 364 (see FIGS. 33 and 48). A microlumen 360 having at least a minimum amount of rigidity while remaining flexible enough to remain safely within the catheter 320 and vein has been found to be advantageous in threading the microlumen 360 into the catheter 320. For example, a reinforced microlumen formed from uncoated (or coated) polyimide and a braided (or unbraided) layer, for example formed from stainless steel, such as product code 165-III available from Microlumen of Oldsmar, Florida, having an ID of 0.0165 inches has been found to possess acceptable properties.

Figure 34:
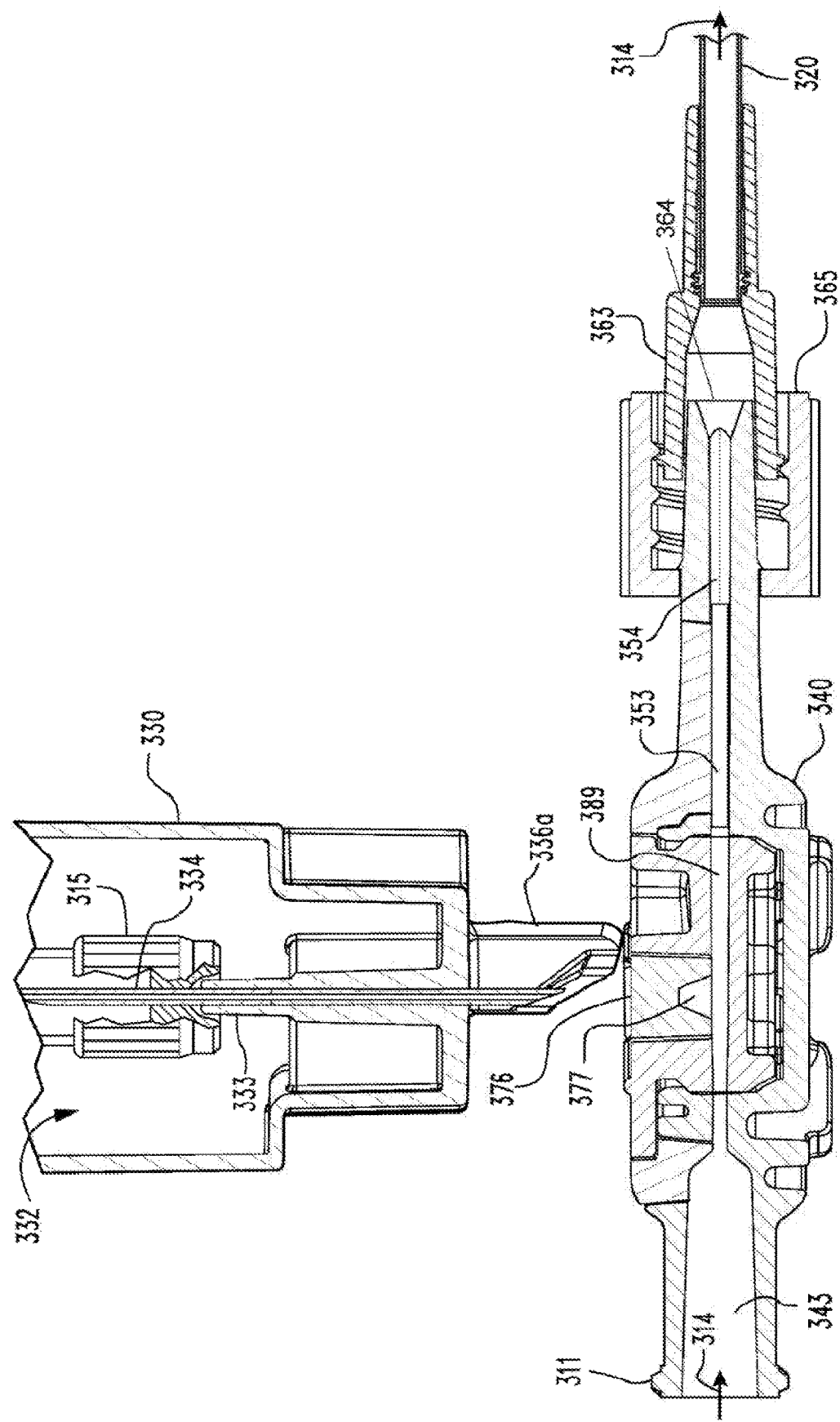
FIG. 34 is a cross-sectional view of the valve housing and separated tube holder taken along sectional cutting plane line 34-34, shown in FIG. 32, and with the device in the infusion/non-collection mode.
Figure 35:
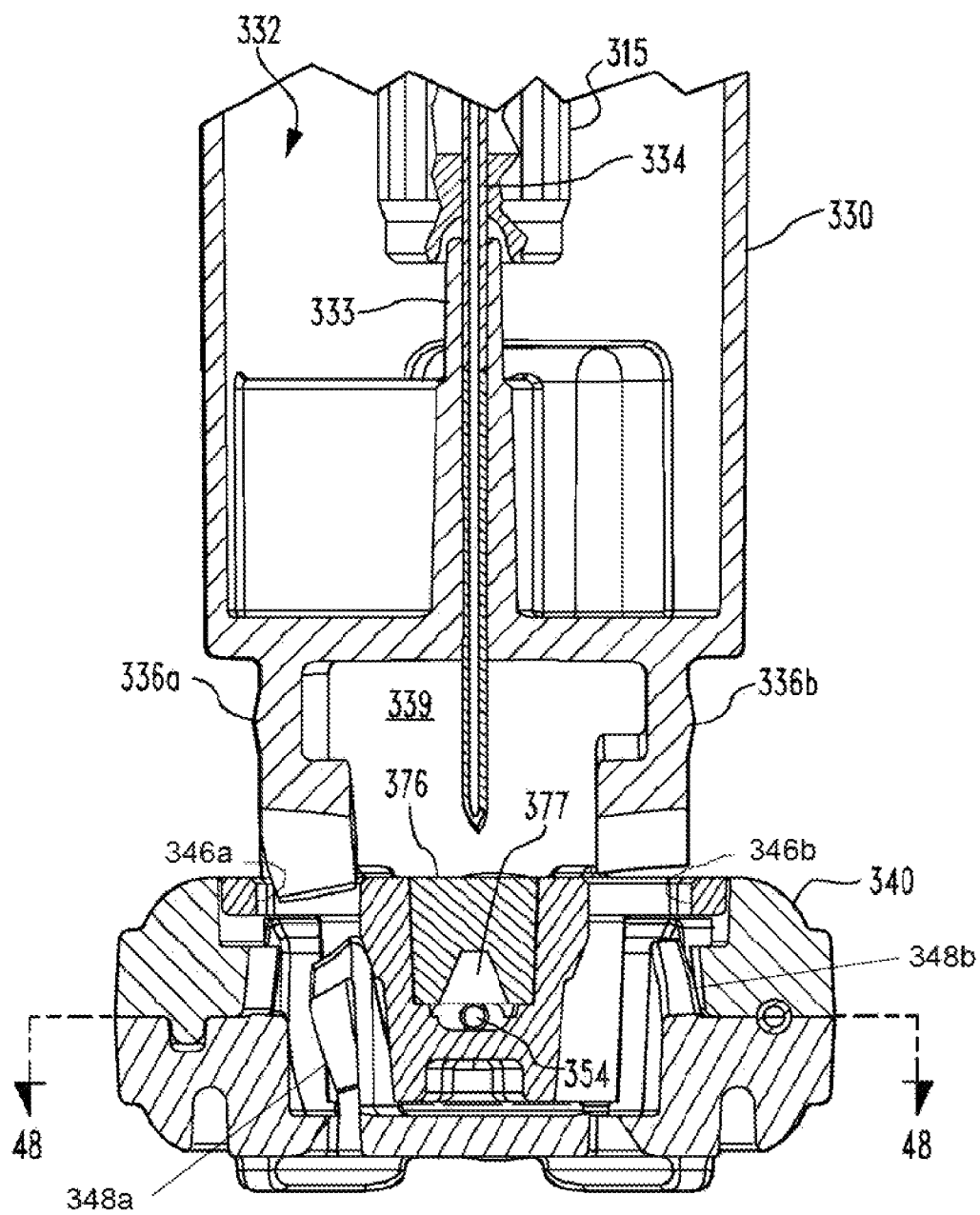
FIG. 35 is a cross-sectional view of the valve housing and separated tube holder taken along sectional cutting plane line 35-35, shown in FIG. 32, and with the device in the infusion/non-collection mode.
Figure 36:
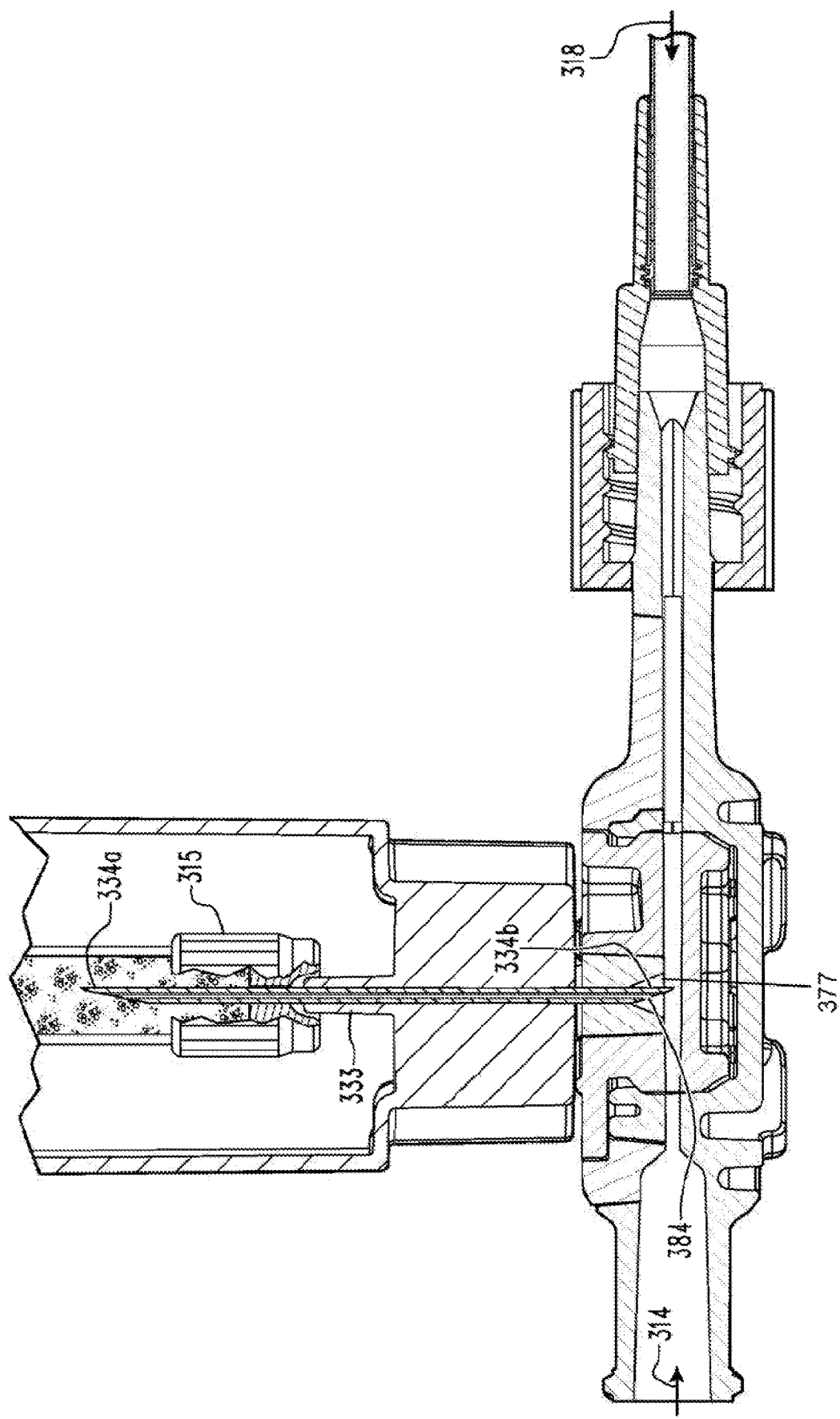
FIG. 36 is a cross-sectional view of the valve housing and coupled tube holder taken along sectional cutting plane line 34-34, shown in FIG. 32, and with the device in the infusion/collection mode.
Figure 37:
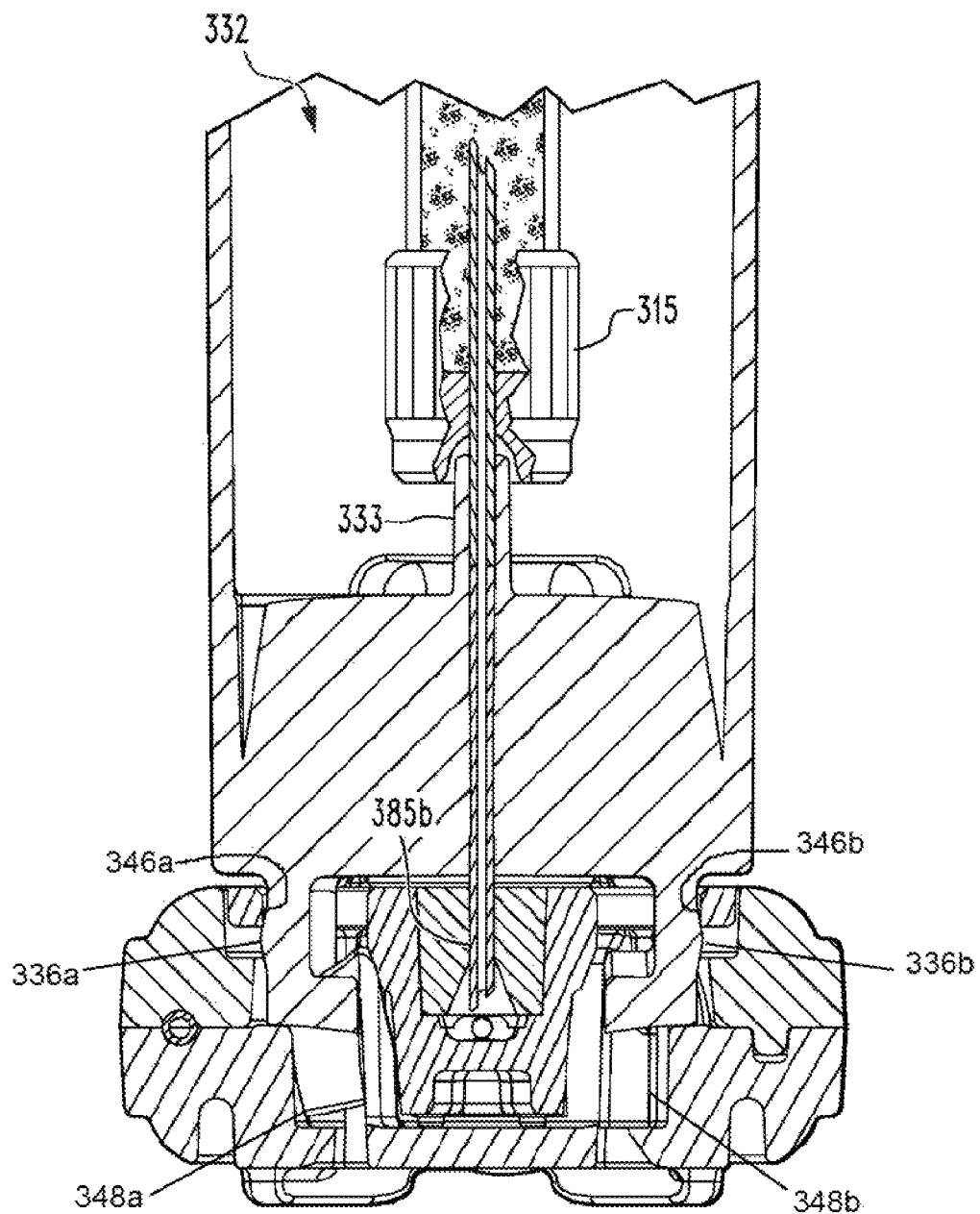
FIG. 37 is a cross-sectional view of the valve housing and coupled tube holder taken along sectional cutting plane line 35-35, shown in FIG. 32, and with the device in the infusion/collection mode.

Referring to FIG. 34, the tube holder 330 includes a central tube receptacle 332, a tube stop 333 at the base of the receptacle 332, tube holder engagement features 336a and 336b, and a draw needle 334. As depicted in FIGS. 33, 35, and 37, the tube holder engagement features 336a and 336b, for example projections extending downward from the tub holder 330 and having angled surfaces and locking engagement features defined thereon, are configured to fit within receivers 346a and 346b in the valve housing 340 and engage with ramps 348*a* and 348*b* defined by the valve housing 340 when coupling the tube holder 330 to the valve housing 340. During engagement of the tube holder 330 with the valve housing 340 the draw needle 334 axially extends into the septum top 375 and into the sample chamber 377 placing the needle channel 384 into the valve interior passageway 389 (see FIGS. 34-37 and 47-49). In the depicted embodiment, the entire tip of needle 334 extends into the sample chamber 377 with all of the angled surfaces of needle 334's tip being present in the sample chamber 377, as shown in FIGS. 36 and 37.

The tube holder interfaces 336*a* and 336*b* in conjunction with the draw needle 334 couple a blood collection tube 315 to the valve housing 340. The tube holder 330 further functions to rotate the rotary valve 380 between the non-collection position 383*a* (see FIG. 48) and the collection position 383*b* (see FIG. 49), which in the illustrated embodiment is about 15 degrees of rotation relative to valve housing 340. As the engagement features 336*a* and 336*b* slide through receivers 346*a* and 346*b* and with axially coupling of the tube holder 330 with the valve housing 340, needle 334 extends through the septum 376 located in draw port 381 of the rotary valve 380.

The rotation of rotary valve 380 is provided by continued downward movement of engagement features 336*a* and 336*b* through receivers 346*a* and 346*b* contacting with ramps 348*a* and 348*b* as the tube holder 340 is manually extended axially downward and guided in rotation relative to the valve housing 340. Continued axially downward movement contacts opposing ramped surfaces of ramp 348*a* and engagement feature 336*a* and ramp 348*b* and engagement feature 336*b*, respectively, guiding rotation of engagement features 336*a* and 336*b* and rotating rotary valve member 382 via receivers 346*a* and 346*b* defined in therewith relative to valve housing 340. The corresponding locking surfaces of engagement features 336*a* and 336*b* corresponding with locking surfaces of valve housing 340 limit downward movement toward and retains tube holder 330 in position relative to the valve housing 340, thereby also retaining the rotary valve 380 position relative to valve housing 340.

Relative to the tube holder 330, the draw needle 334 extends through the tube stop 333 and has a top end 334*a* extending above the tube stop 333 and upwardly into the tube receptacle 332, or directly through the needle cover 335 into the blood collection tube 315 if one is connected. The draw needle 334 also extends downwardly below the tube stop 333 and has a bottom end 334*b* extending below the tube stop 333 and downwardly within the central area 339 (FIG. 35) between the draw port interfaces 336*a* and 336*b*. Optionally, mechanical features can be provided with the tube holder 330, housing 340, and/or the rotary valve 380 so that engagement of mechanical protrusions with corresponding detents or other sensory feedback can be provided to indicate the range of limits of full rotation and/or axial translation to ensure proper use and operation.

The series of FIGS. 34-37 illustrate stages of blood sample collection: preparing the system 300 for a blood draw (FIGS. 34-35) and drawing blood into collection tube(s) 315 in the infusion/collection mode 383*b* of operation with the system 300 in the infusion/collection configuration (FIGS. 36-37).

Referring to FIGS. 34-35, prior to coupling tube holder 330 to the valve housing 340, the rotary valve 380 is positioned in a non-collection position 383*a* (see FIG. 48). In this position, the valve passage 389 of the rotary valve 380 fluidly couples the IV inlet 343 of the valve housing 340 to the blood collection channel 354 of the valve housing 340 allowing the device to supply IV fluid 314 to the catheter head 363 and catheter 320.

Referring to FIGS. 36, 37 and 45-49, when the rotary valve 380 is rotated to a collection position 383*b* (see FIG. 49), such as by inserting engagement features 336*a* and 336*b* and draw needle 334 into the valve housing 340 and septum 376, respectively, the valve passage 389 of rotary valve 380 moves out of alignment with the IV inlet 343 becoming fluidly isolated (fluidly isolated from within device 300) from the infusion channel portion 358 yet remaining in fluid communication (in fluid communication from within device 300) with the blood collection channel 354, thus providing a path for blood 318 entering the distal end 322 of the catheter 320 to pass through hemotube 353 and be supplied to the valve passage 389, the sample chamber 377 of the septum 376 and the needle channel 384. In this collection position 383*b*, the sample chamber 377 of the septum 376 (which is positioned within the draw port 381) is fluidly coupled to the collection tube 315 by needle passage 384.

Figure 49:
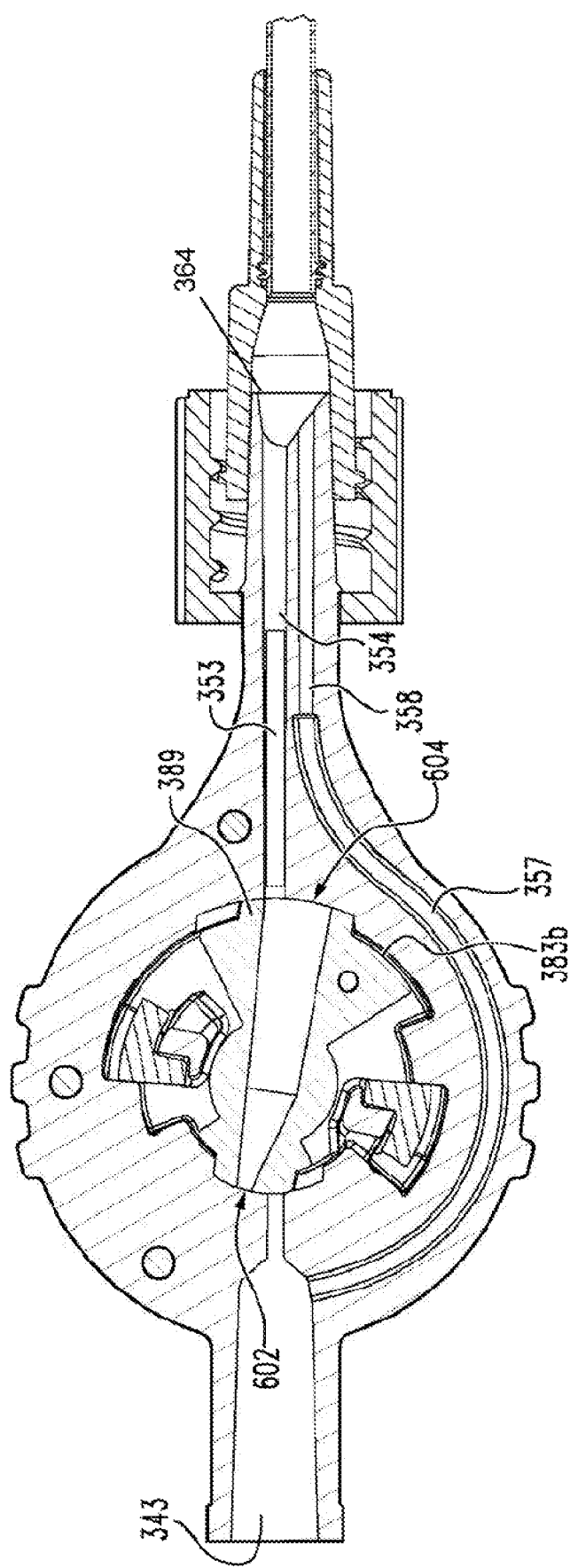
FIG. 49 is a cross-sectional view of the valve housing taken along sectional cutting plane line 48-48, shown in FIG. 35, and with the device in the infusion/collection mode.

When two locations are described as being "fluidly isolated," "fluidly coupled," "in fluid communication" or the like, as in the above paragraph, it is understood that a fluid pathway external to the device 300 can exist between the two locations. For example, while rotating rotary valve 380 to a collection position 383*b* as depicted in FIG. 49 fluidly isolates IV inlet 343 from the valve passage 389, this fluid isolation occurs within the device 300 and there is admittedly a fluid pathway from inlet 343 to the valve passage 389 via the infusion channel 358, the blood vessel and the blood collection channel 354. When such a fluid pathway external to the device/system exists, the meaning of terms like "fluidly isolated," fluidly coupled" and "in fluid communication with" in this context are intended to imply that the isolation, coupling or communication relates to the internal passageways and functions of the device/system 300 or 100.

Once blood has been collected, the collection tube 315 can be uncoupled from the tube holder 330, and if desired, subsequent collection tubes 315 can be coupled, filled, and uncoupled. With no collection tube 315 in place, the lack of a vacuum, the passive fluid flow restriction provided by the needle 334 and the additional sealing by the elastomeric cover 335 covering the upper end 334*a* of the needle 334, blood 318 will not flow through needle 334. The appropriate flow restriction can be provided by selecting the proper ID of the needle 334, by crimping the needle 334 to a specific desired cross-sectional area, or by other mechanically passive means to limit flow.

To return the system 300 to the infusion/non-collection configuration and the infusion/non-collection mode of operation 383*a* (see FIGS. 34-35), tube holder 330 is rotated counterclockwise and separated axially away from the valve housing 340. Rotating the tube holder 330 counterclockwise returns the rotary valve 380 to the non-collection valve position 383*a*, fluidly recoupling the blood collection channel 354 with the therapy fluid 314 from the IV inlet 343. Rotating the tube holder 330 counterclockwise also axially translates the interfaces 336*a* and 336*b* and needle 334 upwardly. Advantageously, the septum 376 is self-sealing and capable of reuse, so that when the needle 334 is repeatedly withdrawn the IV fluid 314 flows through the valve passage 389 without leaking through the septum 376.

Advantageously, the collection of blood 318 occurs simultaneous without interruption of infusion of IV therapy fluid 314 through infusion channel 358, exiting into the vein of the patient at the distal end 362 of the microlumen 360. The ability of the system 300 to provide this function is due in part to two features of the device: a protrusion of the tip of the microlumen 360 in the vein an optimum minimum distance beyond the tip of the catheter 320 (see FIG. 32), and a related restriction in the flow in the blood 318 being collected when the rotary valve 380 is rotated to the collection position 383*b*.

When determining the precise dimensions of the components in the infusion and blood collection device, system and/or methods 300 (or device/system/methods 100), a number of parameters can be taken into account to ensure the device/system will effectively operate in a variety of situations. These parameters include the type of patient (for example, humans (including adults, adolescents, children, and infant), canines, felines, etc.), where vein is located (arm, leg, etc.), the diameter of a typical vein being accessed, the standard venous blood superficial velocities in the vein being accessed, the densities and viscosities of the expected IV fluid, the standard blood densities and viscosities, the thickness of the microlumen wall, and the standard vacuum pressures in the blood collection device In one example embodiment the distal tip 362 of microlumen 360 extends at least 9 mm (0.35 inches) beyond the distal tip 322 of the catheter 320, the internal diameter of needle 334 is 0.30 mm (0.012 inches), and the length of needle 334 is 3.3 cm (1.3 inches), which result in a maximum blood collection flow rate of 5 ml/min and prevents the IV fluid 314 flowing out from the distal tip 362 of the microlumen 360 from being mixed with the blood 318 being drawn into the distal tip 322 of the catheter 320 for collection in the collection tube 315. A device/system/method with these features is effective when used with a typical vein in an adult forearm with standard forearm venous blood superficial velocities, typical forearm vein diameters, IV flow rates greater than 1 ml/min, minimal Microlumen wall thicknesses, standard blood densities and viscosities, typical IV fluid densities and viscosities, and standard vacuum pressures (mmHg) from current vacuum products, for example, Vacutainers® and Vacuettes.®

In another embodiment, the distal tip 362 of microlumen 360 extends at least 3 mm (0.12 inches) beyond the distal tip 322 of the catheter 320, and the internal diameter and length of needle 334 is sized to allow a maximum blood collection flow rate of less than 5 ml/min in order to prevent the IV fluids 314 from mixing with the blood 318 being collected through catheter 320.

Additional embodiments include microlumen lengths and needle dimensions sized to draw blood without IV fluid contamination from patients and veins of different sizes, such as the arms or legs of adult, pediatric, or neonatal patients. As an example, a manufacturer can sell the device/system in three sizes, one for adult patients, one for pediatric patients, and one for neonatal patients.

Figure 32:
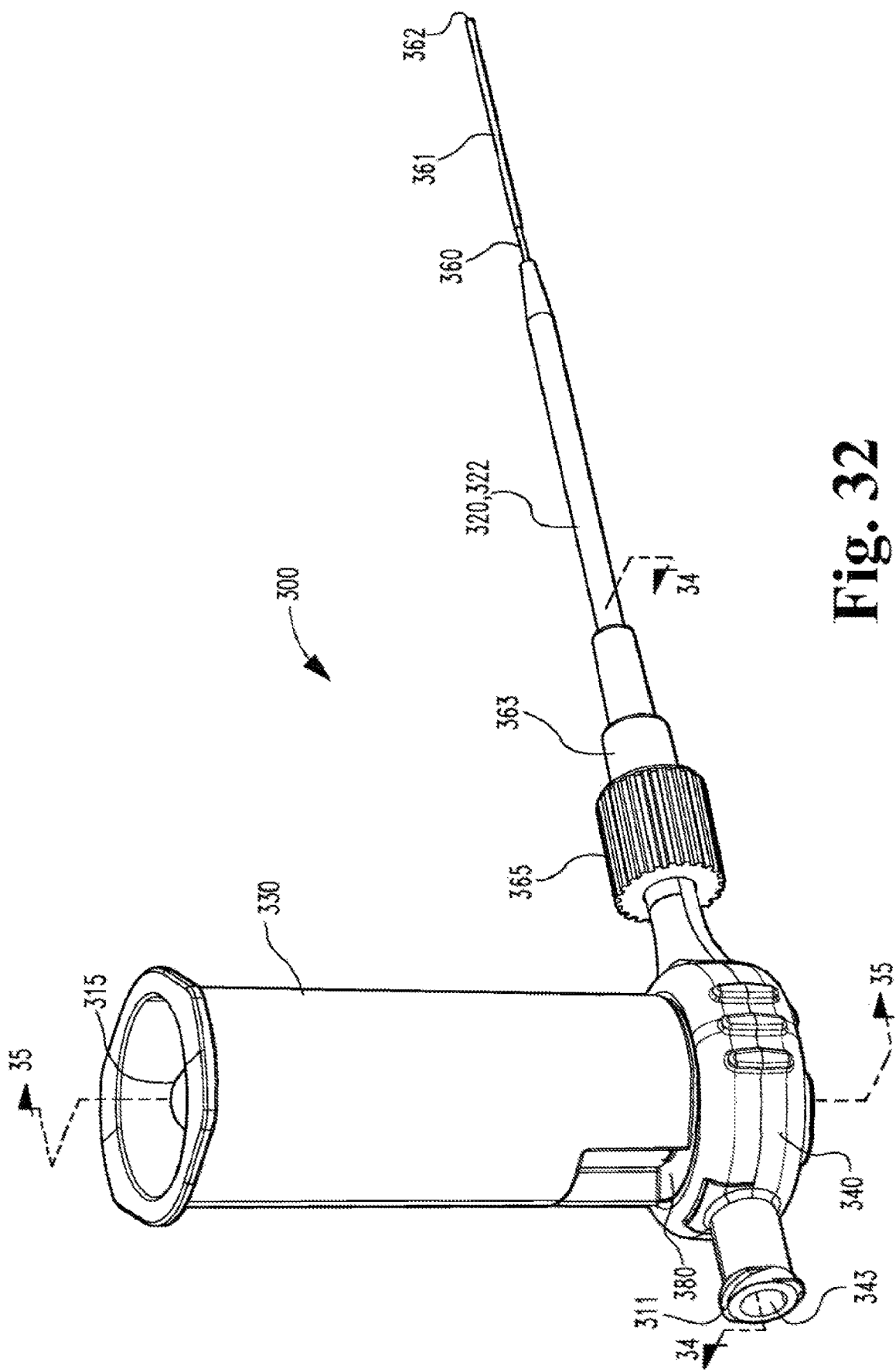
FIG. 32 is a perspective assembly view of a third illustrative embodiment of an infusion and blood collection device as used with an IV infusion line and a Peripheral Venous Catheter.

The overall design of embodiments like the ones depicted in FIGS. 1 and 32 allow easy adaptation of the device/system/method to operate effectively in different scenarios. As an example, by adjusting three features—the distance the distal tip 362 of microlumen 360 extends beyond the distal tip 322 of the catheter 320, the diameter of the lumen through needle 334, and the length of the lumen through needle 334 (which can be approximated by the length of needle 334)—the device/system/method can be modified for use with different patients and different situations allowing simultaneous infusion of IV fluid while drawing blood that is not mixed with IV fluid.

Depending on the size of the catheter 320 being used, the microlumen 360 can occupy between 5% and 95% of the inner diameter of the catheter 320. In other embodiments, the microlumen 360 occupies between 10% and 50% of the inner diameter of the catheter 320, and in a still further embodiments the microlumen 360 occupies between 15% and 30% of the inner diameter of the catheter 320.

The size of the microlumen 360 must be sufficiently large so that when the device transitions from infusing IV fluid through both the microlumen 360 and the catheter 320 to infusing IV fluid through only the microlumen 360 (the catheter 320 being used to draw blood), the passageway through the microlumen 360 cannot create backpressure in the IV fluid that exceeds the IV pump's setting for detecting an occlusion (for example, greater than 10 psi). If the pressure in the microlumen 360 is too high when only the microlumen 360 is infusing IV fluid, the IV pump will reach its preset obstruction pressure (in essence detecting that there is an occlusion) and will automatically shut down (essentially "assuming" there is an occlusion), thereby ceasing infusion of the IV fluid into the patient and inhibiting the flushing of the blood out of catheter 320 when the healthcare provider has stopped collecting blood from the patient.

The catheter 320 in the illustrative embodiment 300 is an 18-gauge catheter, although other embodiment can include larger gauge catheters (for example 16-, 14- and 12-gauge catheters) without significantly changing (by more than 20 percent (20%)) the dimensions of the other portions of the device 300. Smaller catheters (for example, 24- and 26-gauge catheters) may also be used with the device 300 for compatibility with smaller patients (such as pre-mature infants) although the other portions of the device 300 will likely require resizing.

In regard to the restriction of blood flow 318 to reduce the blood collection flow rate to the point that the IV fluid flow is not reversed in the vein and drawn into the catheter 320 and the blood collection tube 315, this restriction can be accomplished at various locations along the flow path of the blood 318 between the distal end 322 of catheter 320 and the blood collection tube 315, either by an active restriction device (for example, a configurable valve, worm gear, or pump), a passive restriction device, or a combination of active and passive restriction devices.

In the above illustrative embodiment of the system 300, the passive restriction in flow rate is made via the choice of the gauge of the draw needle 334 that penetrates the end of the collection tube 315. A needle is selected having a sufficiently narrow internal diameter to provide the required limit to the blood flow rate. If a larger internal diameter is used, the vacuum in the blood collection tube 315 will need to be decreased (stated differently as less negative pressure, a weaker vacuum, or higher absolute pressure), the length of the needle will need to be increased (the slowing of fluid being a function of the surface area inside the needle), or a combination of both will be needed. Advantages are realized by using the entire length of the needle to slow the flow of the blood being drawn to an appropriate rate. While some embodiments can restrict the flow rate by necking or crimping methods, which produces a small aperture along a short distance in the flow direction, care must be exercised since this type of flow restriction increases the likelihood of negative effects such as damaging the blood sample (for example, hemolysis by blood shearing or other physical forces).

In the illustrative device/system/method 300 with the distal end 362 of the microlumen 360 extending, for example, about 10 mm beyond the distal end 322 of catheter 320, a restriction limiting the flow rate to about 5 ml/minute or less provides the desired lack of contamination of the blood sample collected. This desired restriction is provided by using a draw needle 334 having a gauge of about 24.

The volume flow rate (Q) of the blood 318 is driven by the change in pressure (ΔP) for the blood 318 between the patient and the collection tube 315, and most notably in the illustrative embodiment of the system 300, at the point of highest passive restriction in the blood flow 318, the draw needle 334. In order to specify a needle gauge that will limit the volume flow rate (Q) to the desired magnitude, for example, about 30 ml/min or less, or about 15 ml/min or less, or 10 mil/min or less, the fluid dynamic principles for fluid flow with an applied force and no-slip boundary condition between a desired blood volume flow rate (Q) and a pressure gradient (ΔP) can be used. In an illustrative embodiment, for example, using 1.16 inch 18 gauge catheter and a 6 ml red collection tube 315, the typical flow rate of blood 318 is observed to be about 7 ml/min.

Figure 38:
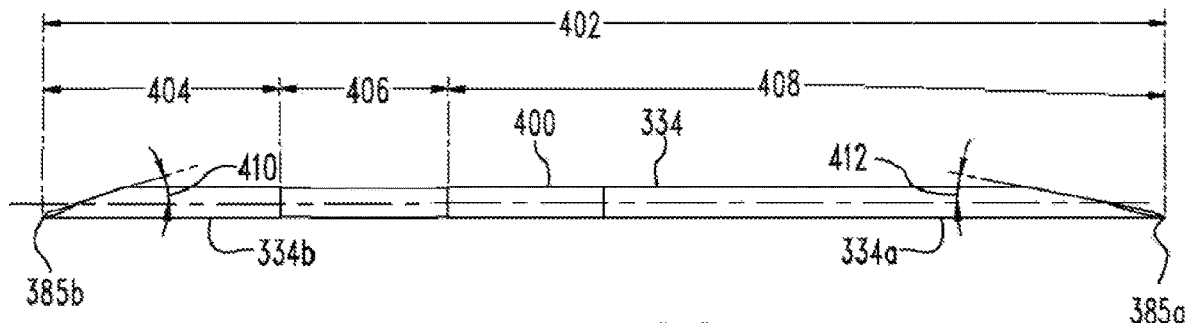
FIG. 38 is a side view of the draw needle of the infusion and blood collection device of FIG. 32.
Figure 39:
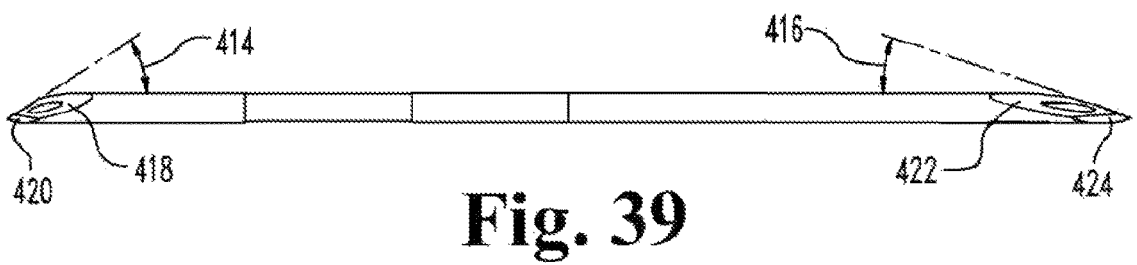
FIG. 39 is a perspective view of the draw needle of the infusion and blood collection device of FIG. 32.
Figure 40:
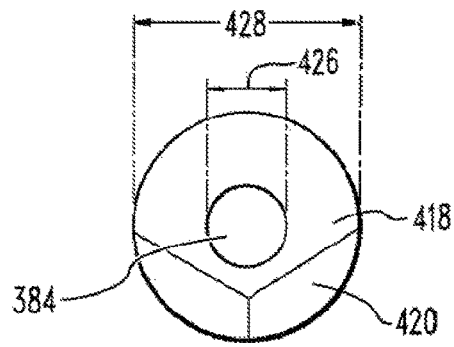
FIG. 40 is an end view of the draw needle of the infusion and blood collection device of FIG. 32.
Figure 41:
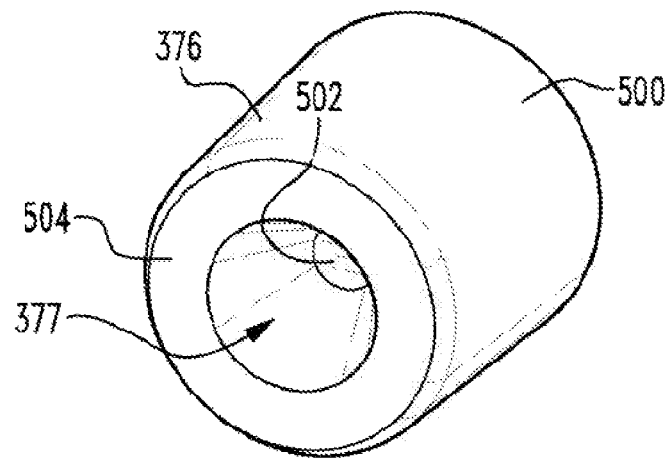
FIG. 41 is a perspective view of the septum of the infusion and blood collection device of FIG. 32.
Figure 42:
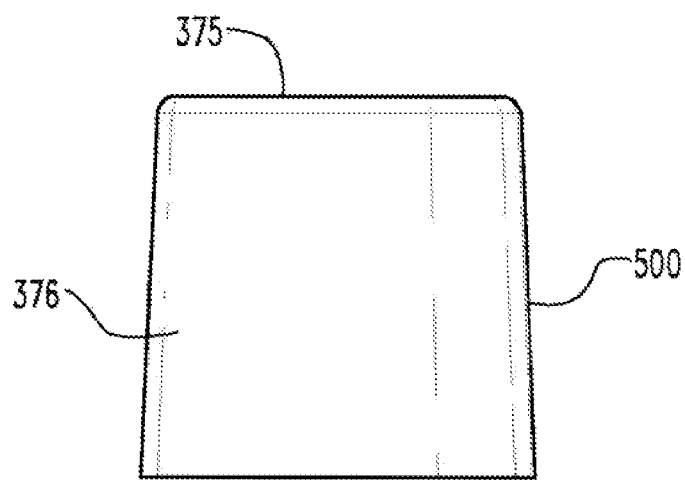
FIG. 42 is a side view of the septum of the infusion and blood collection device of FIG. 32.
Figure 43:
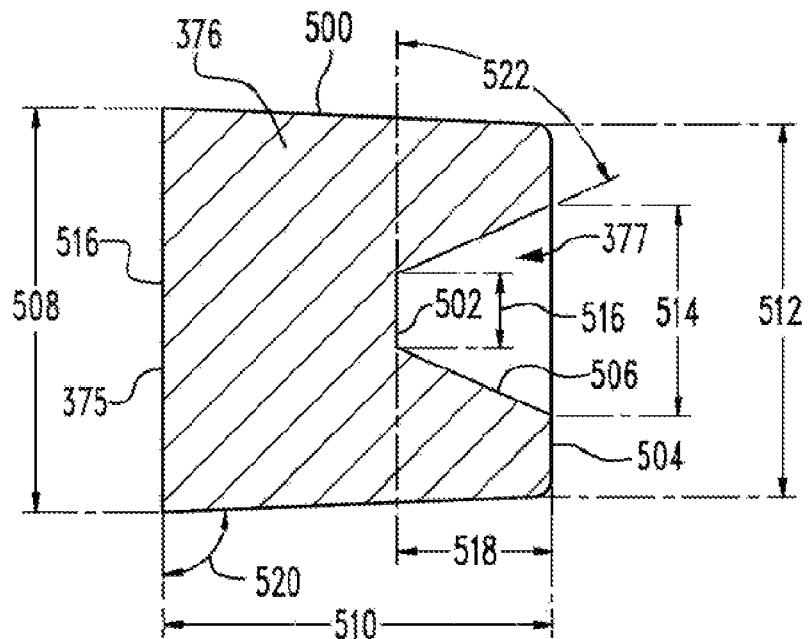
FIG. 43 is a cross-sectional view of the septum of the infusion and blood collection device of FIG. 32.
Figure 44:
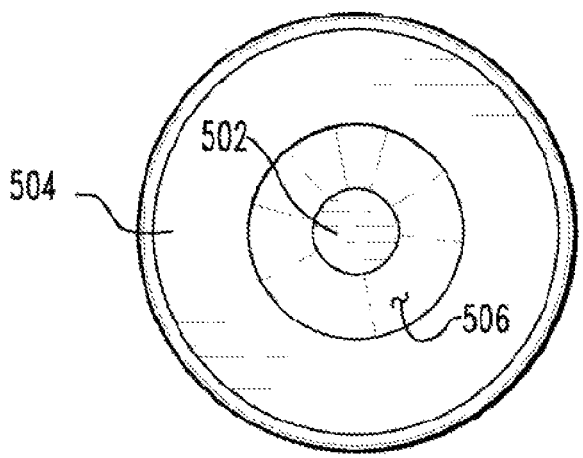
FIG. 44 is an end view of the septum of the infusion and blood collection device of FIG. 32.

Depicted in FIGS. 38-40 is an example of a draw needle 334 for positioning inside the tube holder 330 of the system 300 according to one embodiment of the present disclosure. The illustrative draw needle 334 can have a body 400 cut from a length of stainless-steel hypodermic round tubing stock and can include tip ends 385a and 385b. In the illustrated embodiment, tip 385a functions to puncture the cover sleeve 335 and a collection tube 315 while tip 385b functions to puncture the septum 376 of the system 300. The draw needle 334 can have a total length 402 of about 1.3 inches including, for example: a first portion 404 about 0.28 inches in length which extends into the central area 339 of the tube holder 330, a second portion 406 about 0.20 inches in length which couples the needle 334 to the tube holder 330 (for example, using an adhesive), and a third portion about 0.85 inches in length, the tip of which extends into the central tube receptacle 332. Each end 385a and 385b includes a beveled portion and a lancet portion. Tip end 385a is configured to penetrate the seal of a vacuum container 315 and includes a beveled portion 422 having a primary bevel angle 412 of about 11 degrees relative to the body 400 and a secondary bevel portion 424 having a secondary bevel angle 416 of about 19 degrees relative to the longitudinal axis of body 400. Tip end 385b is configured to penetrate septum 376 and includes a beveled portion 418 having a primary bevel angle 410 of about 18 degrees relative to the longitudinal (long) axis of body 400 and a secondary beveled portion 420 having a secondary bevel angle 414 of about 32 degrees relative to the longitudinal axis of body 400. To achieve optimal flow rate as noted above, the needle 334 can include an inner diameter 426 of about 0.012 inches (0.3 mm) and an outer diameter 428 of about 0.036 inches.

As described herein, the draw needle 334 punctures the septum 376 upon connection of the tube holder 330 to the rotary valve 380 in collection mode 383b, and the septum 376 self-seals the puncture upon the decoupling of the tube holder 330 and the rotary valve 380. To achieve the self-sealing function, the septum 376 can be constructed using an elastomeric material. The septum 376 has a generally frustoconical shape overall, including a cylindrical body 500, a planar entrance surface 375 for the draw needle 334 to enter, a planar exit surface 502 for the draw needle 334 to exit septum 376 and enter the sample chamber 377 (see FIGS. 36-37), and a planar surface 504 which is positioned facing the IV infusion/blood collection channel 354 when septum 376 is mounted to rotary valve 380. The puncture surface 375 is planar, which provides for easier cleaning by simple wiping once a collection has been performed and the tube holder 330 has been removed.

The transition surface 506 and puncture exit surface 502 collectively define the upper boundaries of the inner sample chamber 377, or dome. Advantageously, once a collection is performed by the draw needle 334 inside the sample chamber 377 and the draw needle 334 is removed from the sample chamber 377, the septum 376 promotes flushing of any residual fluid (for example, blood) remaining inside the sample chamber 377 into the IV infusion/collection channel 354 once IV fluid 314 flows back through the channel 354 when the rotary valve 380 rotates to the non-collection position 383a. In other words, the shape of the bottom of septum 376 can be configured so that IV fluid 314 rinses any residual fluid remaining in sample chamber 377 (such as fluid adhering to the walls of sample chamber 377) after the collection from the second end of the body, the end defining the sample chamber 377, and into the IV infusion/blood collection pathway 354 after the rotary valve 380 transitions from the collection position 383b to the non-collection position 383a. To promote flushing of the sample chamber 377, the sample chamber 377 may extend into less than half of the full length of the septum 376 in some embodiments. Providing the septum 376 with the sample chamber 377 for the needle 334 to be inserted is advantageous because the concave sample chamber 377 allows for the IV infusion/collection channel 354 to be narrower (that is, a smaller cross sectional diameter), and a smaller cross sectional area can lead to easier flushing. While a curved surface of the sample chamber 377 will also accept a needle 334 and promote flushing, the frustoconical shape described herein provides the combination of space for the needle 334 and flushing capabilities.

In alternative embodiments, the septum 376 and rotary valve 380 are formed together as one continuous single-piece article. In these embodiments, the sample chamber 377 is similarly the raised portion of the valve passage 389 formed by the rotary valve 380.

To promote the collection and flushing operations described above, at least one embodiments of the sample chamber 377 has the following approximate dimensions: a diameter 508 of 5.08 mm on the top surface 375; a height 510 of 4.8 mm; a diameter 512 of 4.76 mm on the bottom surface 504; a diameter 514 of 2.54 mm at the opening of the sample chamber 377; a diameter 516 of 1.0 mm at the puncture exit surface 504 in the sample chamber 377; a depth 518 of 1.91 mm of the sample chamber 377; a surface angle 520 of 92 degrees on the body surface 500 between the top 375 and bottom 504 surfaces with respect to the normal of the top surface 375; and a surface angle 522 of 67.5 degrees on the sample chamber transition surface 506 with respect to the normal of the puncture surface 502. For example, in one embodiment the surface angle 522 is less than about 70 degrees, the ratio of diameter 514 to diameter 516 is greater than about 2.5, and the ratio of depth 518 to diameter 514 is less than about 1.0, or less than about 0.75.

The sample chamber 377 is advantageously shaped and sized to accommodate the entire edge of the draw needle (for example beveled portion 418 of draw needle 334) such that a collection may be unobstructed by any surface of the septum 376. The sample chamber 377 is also advantageously shaped and sized having a slanted (non-perpendicular) transition surface 506 with respect to the normal of the puncture surface 502 which provides resistance and thereby prevents an inversion of the sample chamber 377 when the draw needle 334 punctures the surface for one or more collections. In alternative embodiments of the sample chamber 377, the chamber 377 may be shaped as a rounded dome rather than having a frustoconical shape. However, a rounded dome may, in some circumstances, invert as a draw needle 334 is inserted thereby obstructing the needle 334 clearance and hindering the collection.

Additionally, providing a concave lower surface for the draw needle 334 (for example, surfaces 502, 504 and 506) to collect from allows the IV infusion/collection channel 354, and ultimately the valve housing 340, to be smaller than embodiments that do not have a concave lower surface, making the sample chamber smaller and quicker to be flushed of residual body fluid by the IV fluid.

In some embodiments the sample chamber 377 defines a central axis (such as an axis extending perpendicularly from exit surface 502) that is perpendicular to the overall direction the fluid flows through valve passageway 389, which is generally parallel to the lumen in hemotube 353.

Figure 45:
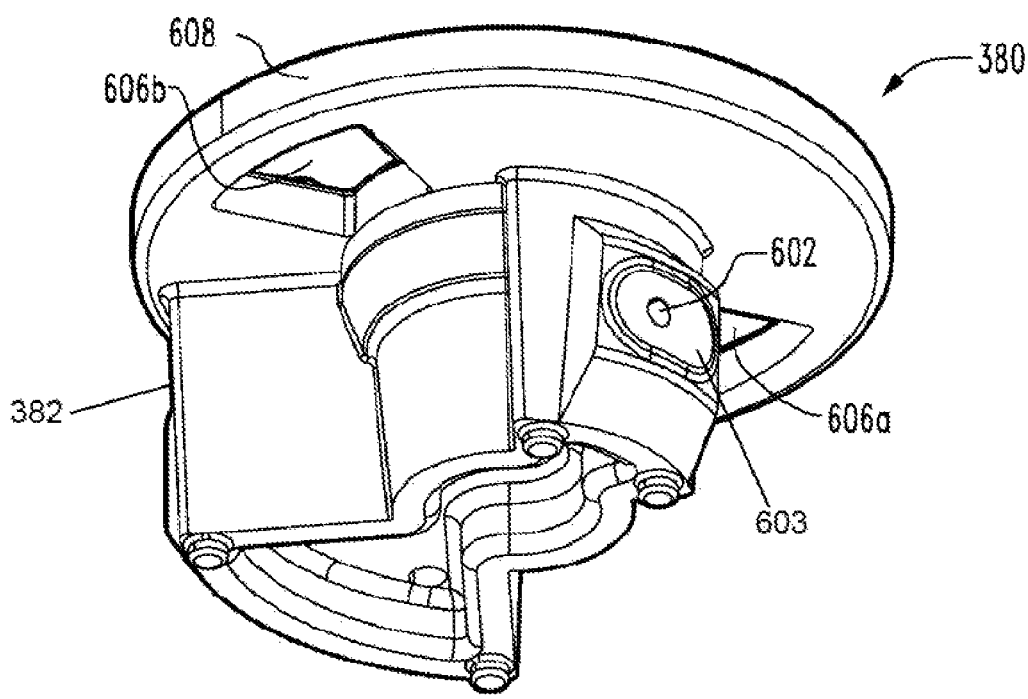
FIG. 45 is a bottom-front perspective view of the diverter valve of the infusion and blood collection device of FIG. 32.

Referring now to FIGS. 45-49, these figures illustrate a rotary valve 380 according to one embodiment of the present disclosure. In use, the rotary valve 380 is inserted into the valve housing 340 with the outer rim 608 and the upper valve portion 340a (see FIG. 33) forming a flush surface. An opening 602 in the rotary valve 380 defines an entryway into the valve passage 389 which, when the device is in the IV infusion/non-collection mode 383a, connects the IV inlet 343 to the IV infusion/collection channel 354 defined by the valve housing 340. More specifically, with reference to FIG. 48, IV fluid 314 in the IV infusion/non-collection mode 383a enters the port opening 602 and flows straight through the rotary valve 380 before exiting through the slit 604, into blood collection channel 354, and toward the catheter 320. Once the tube holder 330 and associated vacuum collection tube 315 is inserted into the rotary valve 380, specifically by pressing the ramped tube holder 330 engagement features 336a and 336b into the rotary valve receivers 606a and 606b, which causes both the tube holder 330 and the rotary valve 380 to rotate, the rotary valve 380 rotating from the non-collection valve position 383a in which the valve passage 389 is fluidly coupled to both the IV inlet 343 and the blood collection channel 354 (see FIG. 48), to a collection valve position 383b in which the valve passage 389 is fluidly isolated from the IV inlet 343 but remains fluidly coupled to the blood collection channel 354 (see FIG. 49). As shown in FIG. 45, a seal 603 can circumscribe the port opening 602 to prevent leakage of fluids into the space between valve member 382 and valve housing 340. For example, the seal 603 can be defined on a surface of the valve member 382, for example, by a medical grade silicone surface layer or other seal, gasket, or ring.

Figure 46:
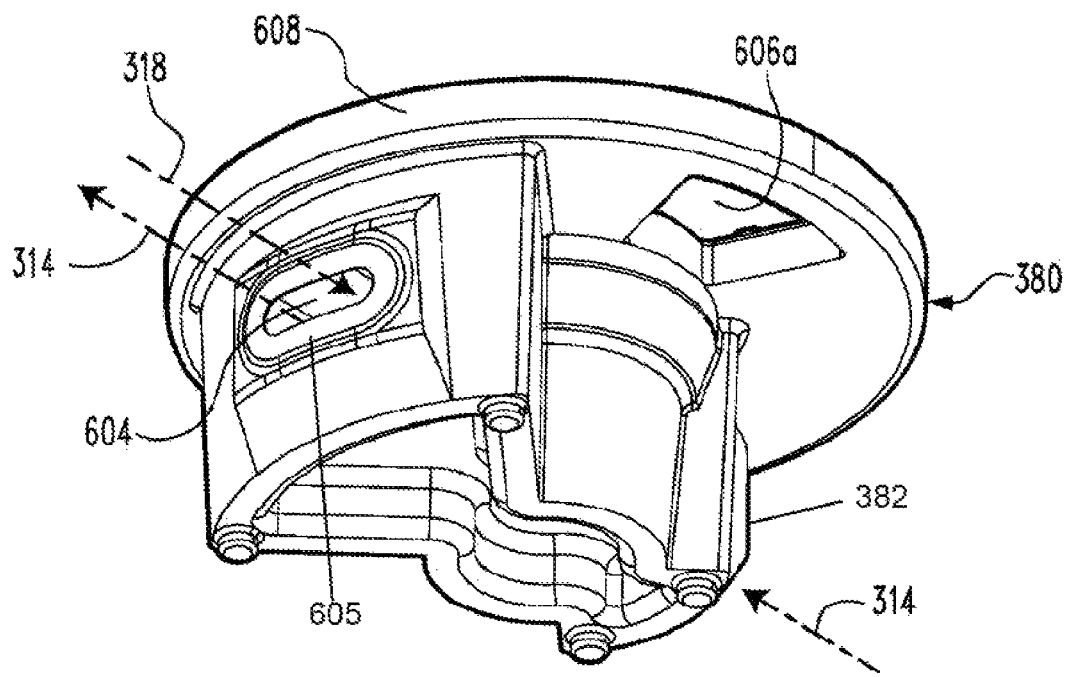
FIG. 46 is a bottom-rear perspective view of the diverter valve of the infusion and blood collection device of FIG. 32.
Figure 47:
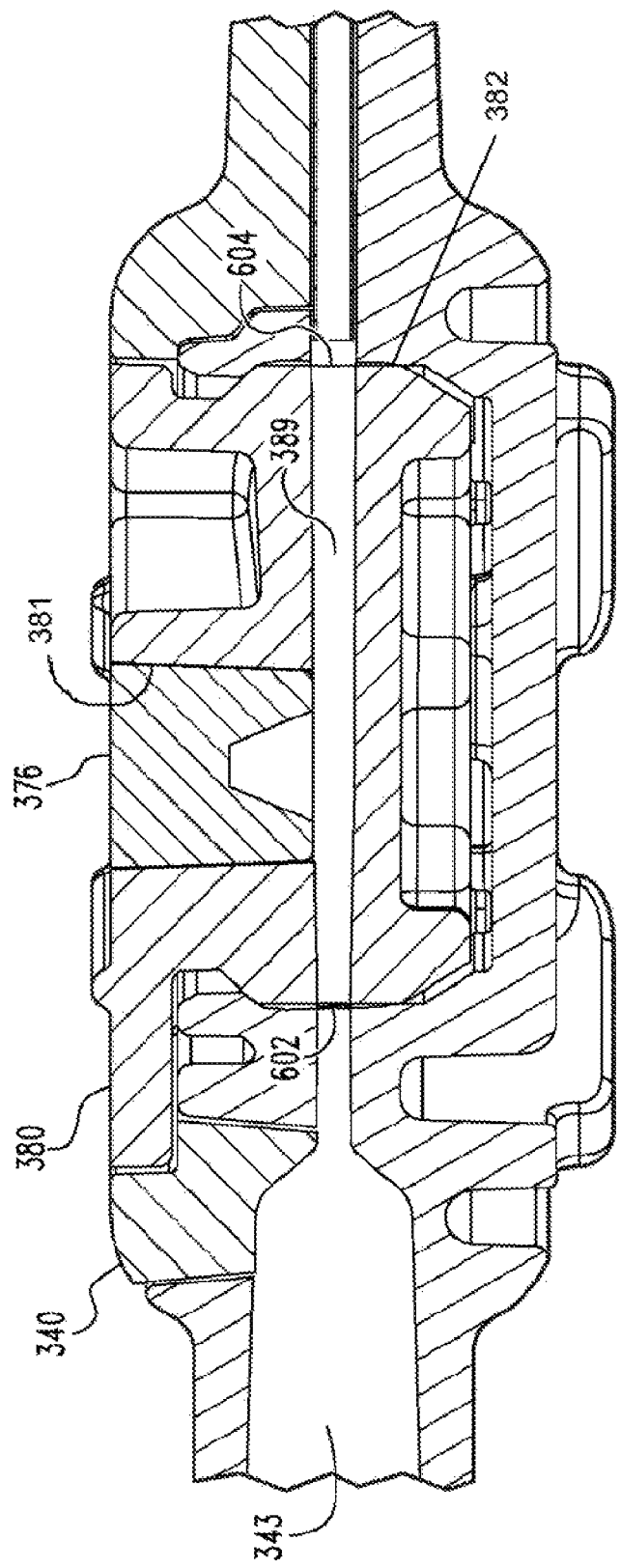
FIG. 47 is a cross-sectional view of the valve housing taken along sectional cutting plane line 34-34, shown in FIG. 32.

In the collection valve position 383b and with a vacuum collection tube mounted in tube holder 330, blood 318 flows into the rotary valve 380 via the port slit 604 and ultimately into the collection tube 315 (see FIGS. 36-37). The valve passage 389 forms a portion of the infusion/non-collection passageway as well as the blood collection passageway in valve positions 383a and 383b, respectively. Advantageously, the slit 604 is elongated such that when the rotary valve rotates about 15 degrees from the infusion/non-collection valve position 383a (FIG. 48) to the infusion/collection valve position 383b (FIG. 49), a fluid connection is maintained between valve passageway 389 and the infusion/blood collection channel 354 while the valve passageway 389 disconnects from the IV inlet 343. As shown in FIG. 46, a seal 605 can circumscribe the port slit 604 to prevent leakage of fluids into the space between the valve member 382 and valve housing 340. For example, the seal 603 can be defined on a surface of the valve member 382, for example, by a medical grade silicone surface layer or other seal, gasket, or ring.

Figure 50:
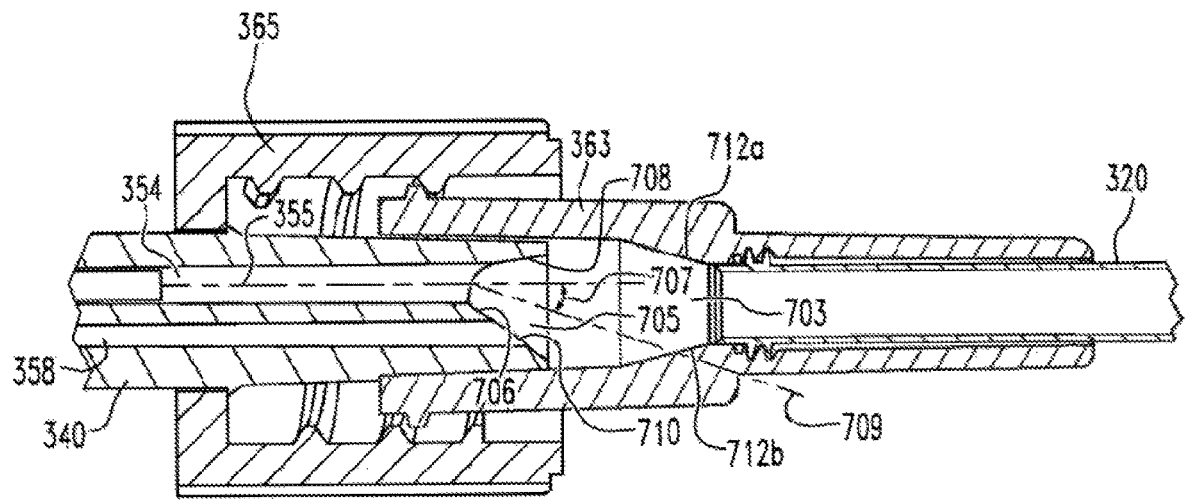
FIG. 50 is a cross-sectional view of the valve housing, luer lock, catheter, and catheter head taken along sectional cutting plane line 34-34, shown in FIG. 32.
Figure 51:
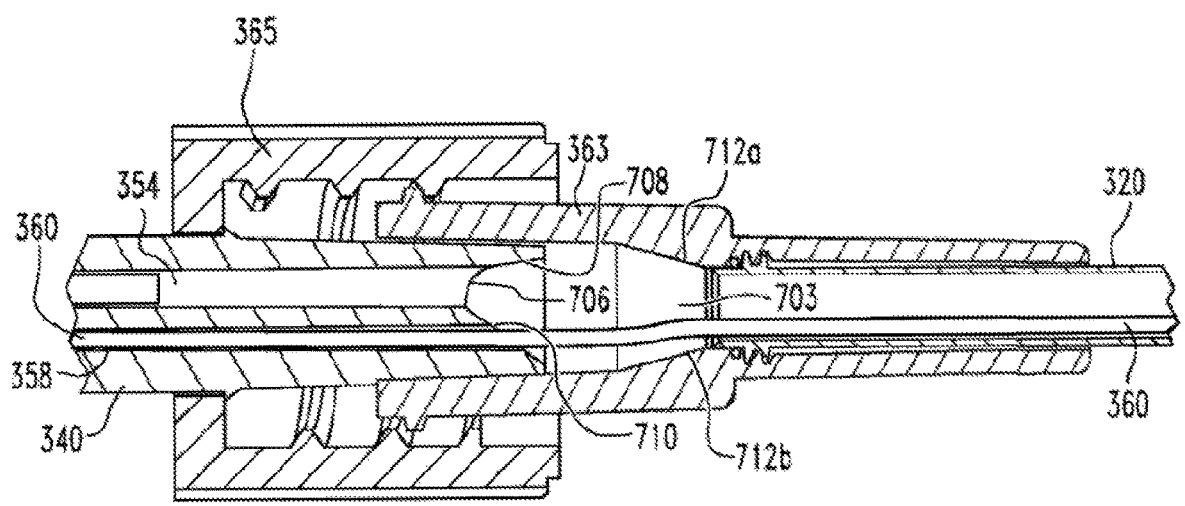
FIG. 51 is a cross-sectional view of the valve housing shown in FIG. 50 including a microlumen, taken along sectional cutting plane line 34-34, shown in FIG. 32.

FIGS. 48 and 51 depict microlumen 360 positioned within the IV infusion channel 358. The microlumen 360 is not depicted in FIGS. 49, 50 and 52 for illustrative purposes. In one embodiment, the microlumen 360 and the infusate tube 357 are joined to the valve housing 340 by initially placing approximately 1-3 millimeters of the tip of microlumen 360 within the infusate tube 357. (With reference to the orientation depicted in FIG. 33, the left end of the microlumen 360 is initially placed within the right end of the infusate tube 357.) Adhesive is applied to the outer surfaces of the joined microlumen 360 and infusate tube 357, and the joined microlumen 360 and infusate tube 357 is inserted into IV infusion channel 358. After hardening, the adhesive holds microlumen 360 and infusate tube 357 together, holds them within IV infusion channel 358, and helps seal any open spaces between microlumen 360 and infusate tube 357 where fluid could otherwise flow.

Figure 52:
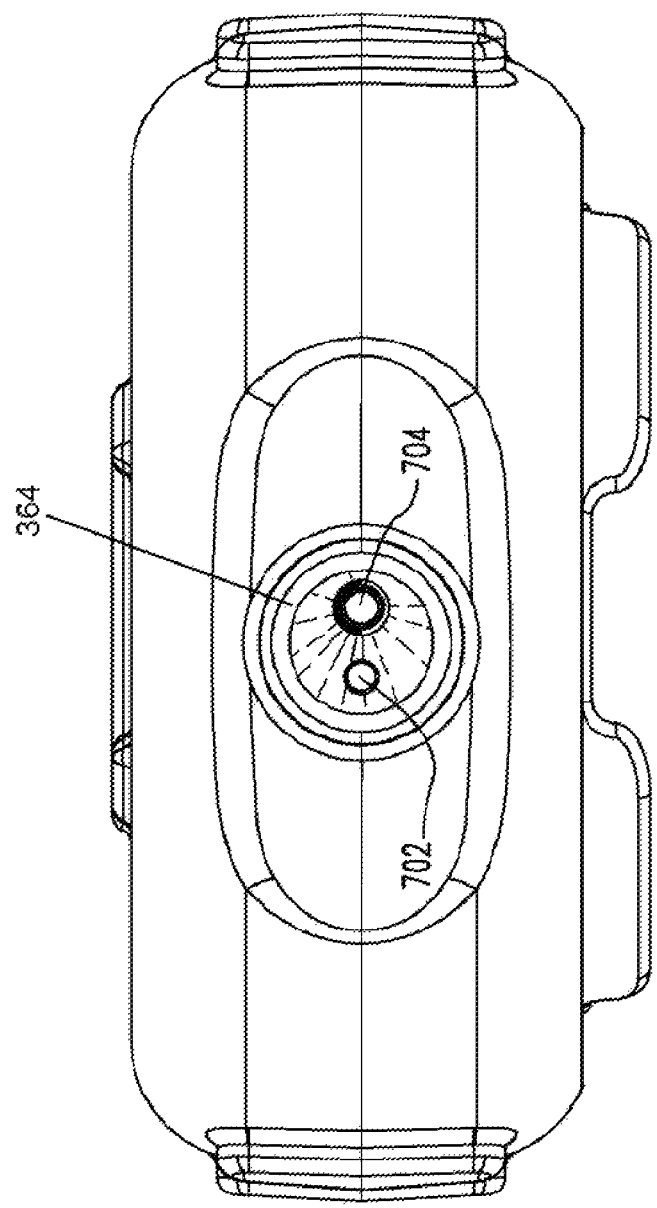
FIG. 52 is an end view of the valve housing of the infusion and blood collection device of FIG. 32.

Depicted in FIGS. 50-51 are cross sectional views of the connection between the valve housing 340 (which includes the infusion/blood collection channel 354 and the IV infusion channel 358), the luer lock 365, the catheter head 363, and the catheter 320. Depicted in FIG. 52 is an end view of the valve housing 340 where the valve housing 340 connects via the catheter head 363 to the catheter 320, but with the catheter head 363, the catheter 320, and the microlumen 360 removed from view. The end view of FIG. 52 illustrates the IV outlet 364, including the first opening 702 to the IV infusion channel 358, which typically houses the microlumen 360, and the second opening 704 to the infusion/blood collection channel 354.

More specifically, the valve housing 340 includes an IV outlet 364 forming a receptacle extending outwardly and having a distal end defining a distal surface 706, wherein the distal surface 706 is a generally concave surface which can include both curved and non-curved portions. The illustrated embodiment includes a first portion 708 and a second portion 710 combining to resemble an asymmetrical funnel shape, for example, the 'spout' portion of which is centered on and formed by infusion/blood collection channel 354, and IV infusion channel 358 opens through a wall thereof. The first portion 708 defines a curved cross-sectional surface wherein the infusion/blood collection channel 354 extends through the valve housing 340 and terminates at the surface of the first portion 708. The second portion 710 defines a concave, convex, or planar cross-sectional surface wherein the infusion channel (housing the microlumen 360) extends through the valve housing 340 and terminates at the surface of the second portion 710.

When operating in the infusion/non-collection mode 383a, IV fluid will flow to the patient through two pathways: through the IV infusion channel 358 to the microlumen 360, and through the hemotube 353 to the catheter 320. After being switched to the infusion/collection mode 383b and with suction applied to the infusion/blood collection channel 354, IV fluid will continue to flow to the patient through the IV infusion channel 358 and the microlumen 360 while the hemotube 353 and the catheter 320 will transport bodily fluid (for example, blood) from the patient. When switching back to the infusion/non-collection mode 383a, IV fluid will continue to flow to the patient through the IV infusion channel 358 and the microlumen 360, and IV fluid will begin flowing through the infusion/blood collection channel 354, the hemotube 353 and the catheter 320 moving bodily fluid from the infusion/blood collection channel 354, sample chamber 377, the hemotube 353, and the catheter 320 into the patient. As can be appreciated by this description of the system 300 self-flushing, there is no need for the health care professional tending to the patient to flush the system 300 after drawing bodily fluid.

The shape and height of the recessed dome of sample chamber 377 influences the effectiveness of the flushing fluid (for example, IV fluid) removing the residual fluid (for example, blood) remaining inside the sample chamber. Higher domes tend to be less effective at removing the residual fluid, especially at low flow rates. However, domes that are too short or small will not provide enough clearance for the draw needle 334 to access the sample chamber.

Because of the shape of the sample chamber 377 of septum 376, IV fluid will move into all corners of the sample chamber 377 and self-flush all of the residual bodily fluid. Although the precise mechanism is not yet understood, it is believed that the sample chamber 377 of septum 376 creates eddies (and/or turbulence) in the fluid flowing through valve passage 389 as it reaches the sample chamber 377 causing the fluid to circulate near the surface 506 of the sample chamber 377 with increased velocity causing enough friction with the surface to quickly flush all of the bodily fluid into valve passage 389 and back into the patient.

Since the fluid appears to lose its ability to efficiently remove fluid from the passageway (for example, the fluid may lose a significant amount of its turbulent flow) as it moves from the sample chamber 377 and approaches the distal end 705 of the valve housing 340, the distal end 705 of the valve housing 340 is carefully shaped to efficiently remove (for example, flush) all of the bodily fluid remaining in the chamber between the end of the infusion/blood collection channel 354 and the beginning of the catheter 320 into the patient. In the embodiment illustrated in FIGS. 48-52, the distal end 705 of the IV outlet 364 of the valve housing 340 defines an asymmetric shape as shown in the figures as surface 706. The asymmetric shape of surface 706 resembles a conical frustum that is generally centered on the opening to the infusion/blood collection channel 354 with the first portion 708 (which may be referred to as the upper portion due to its orientation in FIG. 50) and the second portion 710 (which may be referred to as the lower portion due to its orientation in FIG. 50), which are defined separately since their shapes may be different. In some embodiments the asymmetric shape resembles the surface of an oblique cone. This asymmetric shape encourages IV fluid 314 flowing through the connecting area 703 to completely and rapidly flush all residual body fluid in the connecting area 703 out through the catheter 320. While the precise mechanism is not known, the asymmetric funnel shape of the concave surface 706 appears to create eddies (and/or turbulence) in locations that induce sufficient movement of fluid near the surface of the concave surface 706 to rapidly flush the body fluid away from surface 706 and back into the patient.

In the embodiment illustrated in FIGS. 48-50, the vertex of surface 706 (the location where the curved surface of concave surface 706 would converge if not for the void created by infusion/blood collection channel 354) is recessed behind the opening of the infusion/blood collection channel 354. In other words, the vertex can be located inside the infusion/blood collection channel 354. In some embodiments, the vertex is offset to one side of the central axis 355 of the infusion/blood collection channel 354 (in FIG. 50, the vertex is offset "above" the central axis) and toward the outer edge of the valve housing 340 adjacent outlet 364, in other words, toward the outer edge of the portion of valve housing 340 that connects to the luer lock 365. In these embodiments, the maximum depth of the concave surface is offset to one side of the central axis 355.

The central axis 709 of the concave surface 706 originates at the vertex in the infusion/blood collection channel 354 and is tilted at an angle 707 in relation to the central axis 355 of the channel 354 (or in relation to the longitudinal axis of the valve housing 340. In some embodiments, angle 707 is 10 to 30 degrees and the angle between the axis 709 and the surface of concave surface 706 is 15 to 40 degrees, in other words the total included angle of the cone is approximately 30 to 80 degrees. In further embodiments, angle 707 is 15 to 25 degrees and the angle between the axis 709 and the surface of concave surface 706 is 20 to 25 degrees, in other words the total included angle of the cone is approximately 40 to 50 degrees. In still further embodiments, angle 707 is approximately 20 degrees and the angle between the axis 709 and the surface of concave surface 706 is approximately 23 degrees, in other words the total included angle of the cone is approximately 45 degrees.

Although at least one shape of concave surface 706 has been described as approximating a cone with a vertex, which can imply the sides of the cone converge at a single point, shapes in other embodiments generally resemble a cone but the surfaces do not converge at a single point and instead converge to define a line that can be straight (one dimensional) or curved in two or three dimensions. Moreover, while the concave surface 706 is generally depicted in cross-section as a straight line, which has advantages when manufacturing the device, in other embodiments the concave surface 706 is curved in cross-section. In still further embodiments, concave surface 706 is a conical section, which can have manufacturing advantages due, at least in part, to its relatively simple shape.

The IV infusion channel 358 intersects the concave end surface 706 at a location different from the location where infusion/blood collection channel 354 intersects end surface 706. In some embodiments, the position where the IV infusion channel 358 intersects the concave end surface 706 and the vertex are on opposing sides of the central axis 355 of the infusion/blood collection channel 354. Since the microlumen 360 extends through IV infusion channel 358 and into catheter 320, no fluid entering or exiting infusion/blood collection channel 354 mixes with the fluid in microlumen 360.

As discussed above, embodiments of the claimed system 300 are capable of quickly and efficiently flushing residual blood, which may remain in the catheter 320, the infusion/blood collection channel 354, or the connecting area 703 between the catheter 320 and the valve housing 340 from a blood draw and back into the patient via the catheter 320 once the system 300 is switched from the IV infusion/collection mode 383b back into the IV infusion/non-collection mode 383a. In an illustrative embodiment, a minimum rate of 10 ml/hr of IV infusion after switching from the IV infusion/collection mode sufficiently and timely flushes the system 300 to prevent residue blood from remaining in the device, including areas within the connecting area 703 partially obstructed by the microlumen 360.

Embodiments of the present disclosure include an infusion and blood collection device, system or method that includes an IV infusion line, an IV catheter, or both an IV infusion line and an IV catheter, while other embodiments include an infusion and blood collection device or system independently from an IV infusion line and an IV catheter.

Reference systems that may be used herein can refer generally to various directions (for example, upper, lower, forward and rearward), which are merely offered to assist the reader in understanding the various embodiments of the disclosure and are not to be interpreted as limiting. Other reference systems may be used to describe various embodiments, such as referring to the direction of projectile movement as it exits the firearm as being up, down, rearward or any other direction.

While examples, one or more representative embodiments and specific forms of the disclosure have been illustrated and described in detail in the drawings and foregoing description, the same is to be considered as illustrative and not restrictive or limiting. The description of particular features in one embodiment does not imply that those particular features are necessarily limited to that one embodiment. Some or all of the features of one embodiment can be used in combination with some or all of the features of other embodiments as would be understood by one of ordinary skill in the art, whether or not explicitly described as such. One or more exemplary embodiments have been shown and described, and all changes and modifications that come within the spirit of the disclosure are desired to be protected.

What is claimed is:

1. An intravenous device for administering fluid to an animal body and for drawing a bodily fluid from the animal body and through an elongate tube, comprising:
a first fluid channel configured to receive intravenous (IV) fluid at an IV fluid inlet port and to selectively transport the IV fluid to the animal body and draw the bodily fluid from the animal body;
a bodily fluid draw port; and
an elastomeric seal for sealing the bodily fluid draw port, the elastomeric defining a concave surface on a first end, the concave surface forming an interior surface portion of the first fluid channel; and
wherein the IV fluid flows by the bodily fluid draw port to administer the IV fluid to the animal body in a first intravenous device configuration, and the bodily fluid flows into the first fluid channel and into the elongate tube in a second intravenous device configuration; and
wherein the elastomeric is configured to:
receive the elongate tube extending through the elastomeric and into the first fluid channel through the concave surface,
form a seal around the elongate tube extending through the elastomeric seal, and
inhibit fluid from exiting the first fluid channel through the elastomeric sealing after the elongate tube is removed from the elastomeric seal.

2. The intravenous device of claim 1, wherein the concave surface of the elastomeric seal defines a sample chamber in which a distal end of the elongate tube is located when received by the elastomeric seal.

3. The intravenous device of claim 2, wherein the concave surface of the elastomeric seal is configured to promote flushing by the IV fluid of any residual bodily fluid remaining inside the sample chamber upon transitioning from the second intravenous device configuration to the first intravenous device configuration.

4. The intravenous device of claim 1, wherein the concave surface of the elastomeric seal defines a ratio of a greatest depth to a largest diameter of less than about 1.0.

5. The intravenous device of claim 1, wherein the concave surface of the elastomeric seal defines a ratio of a greatest depth to a largest diameter of less than about 0.75.

6. The intravenous device of claim 1, wherein the concave surface of the elastomeric seal defines a sidewall surface angle of less than about 70 degrees relative to a plane defined across the first end of the elastomeric seal.

7. The intravenous device of claim 1, wherein the concave surface of the elastomeric seal defines a frustoconical shape.

8. The intravenous device of claim 7, wherein a ratio of a diameter of a base of the frustoconical shape to a diameter of the frustoconical shape at the first end of the elastomeric seal is greater than about 2.5.

9. The intravenous device of claim 1, further comprising:
a second fluid channel formed fluidly parallel to the first fluid channel,
wherein the second fluid channel is configured to carry the IV fluid to the animal body in both the first intravenous device configuration and the second intravenous device configuration.

10. The intravenous device of claim 9, further comprising:
a valve housing; and
a valve; and
wherein the valve housing defines the bodily fluid draw port and at least a portion of the second fluid channel, and the valve and the valve housing define at least a portion of the first fluid channel.

11. The intravenous device of claim 10, further comprising:
an outlet member defining a concave distal end surface, the first fluid channel extending through the outlet member and terminating at the concave distal end surface, and wherein the concave distal end surface is shaped to create a fluid flow pattern that removes residual bodily fluid remaining at the concave distal end surface after the intravenous device transitions from drawing the bodily fluid from the animal body through the first fluid channel to administering the IV fluid to the animal body through the first fluid channel.

12. The intravenous device of claim 11, wherein the concave surface of the elastomeric seal defines a sample chamber in which a distal end of the elongate tube is located when received by the elastomeric seal.

13. The intravenous device of claim 11, wherein the concave surface of the elastomeric seal is configured to promote flushing by the IV fluid of the residual bodily fluid remaining inside a sample chamber upon transitioning from the second intravenous device configuration to the first intravenous device configuration.

14. The intravenous device of claim 11, wherein the concave distal end surface of the outlet member defines an asymmetric funnel shaped surface.

15. The intravenous device of claim 11, wherein the valve housing defines the outlet member and the outlet member is configured to connect to a catheter.

16. The intravenous device of claim 11, wherein a maximum depth of the concave distal end surface of the outlet member is out of alignment with a center of the outlet member to create a fluid flow pattern that removes the residual bodily fluid remaining at the concave distal end surface after the intravenous device transitions from drawing the bodily fluid from the animal body through the first fluid channel to administering the IV fluid to the animal body through the first fluid channel.

17. The intravenous device of claim 11, wherein a center of the first fluid channel is in alignment with a point of a maximum depth of the concave distal end surface.

18. The intravenous device of claim 11, wherein the outlet member defines an outer edge, and a center of the first fluid channel is offset toward the outlet member outer edge from a point of a maximum depth of the concave distal end surface.

19. The intravenous device of claim 11, comprising:
a medical tube fluidly coupled with the second fluid channel; and
a catheter coupled to the outlet member; and
wherein the medical tube extends outwardly from the outlet member and into a passageway within the catheter to carry the IV fluid to the animal body.

20. An intravenous device for administering fluid to an animal body and for drawing a bodily fluid from the animal body and through an elongate tube, comprising:
a first fluid channel configured to receive intravenous (IV) fluid at an IV fluid inlet port and to selectively transport the IV fluid to the animal body and draw the bodily fluid from the animal body;
a bodily fluid draw port; and
a sealing means for sealing the bodily fluid draw port, the sealing means defining a concave surface on a first end, the concave surface forming an interior surface portion of the first fluid channel; and
a valve housing;
a valve; and
wherein at least one of the valve and the valve housing define at least a portion of the first fluid channel;
wherein the IV fluid flows by the bodily fluid draw port to administer the IV fluid to the animal body in a first intravenous device configuration, and the bodily fluid flows into the first fluid channel and into the elongate tube in a second intravenous device configuration; and
wherein the sealing means is configured to:
receive the elongate tube extending through the sealing means and into the first fluid channel through the concave surface,
form a seal around the elongate tube extending through the sealing means, and
inhibit fluid from exiting the first fluid channel through the sealing means after the elongate tube is removed from the sealing means.

* * * * *